(12) United States Patent
Bednarek et al.

(10) Patent No.: US 10,676,517 B2
(45) Date of Patent: Jun. 9, 2020

(54) GLUCAGON AND GLP-1 CO-AGONISTS FOR THE TREATMENT OF OBESITY

(71) Applicant: MEDIMMUNE LIMITED, Cambridge (GB)

(72) Inventors: Maria Aleksandra Bednarek, Cambridge (GB); Lutz Ulrich Jermutus, Cambridge (GB); Philip Ambery, Cambridge (GB); Marcella Petrone, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 16/083,064

(22) PCT Filed: Mar. 10, 2017

(86) PCT No.: PCT/EP2017/055679
§ 371 (c)(1),
(2) Date: Sep. 7, 2018

(87) PCT Pub. No.: WO2017/153575
PCT Pub. Date: Sep. 14, 2017

(65) Prior Publication Data
US 2019/0185537 A1  Jun. 20, 2019

Related U.S. Application Data

(60) Provisional application No. 62/306,121, filed on Mar. 10, 2016.

(51) Int. Cl.
*A61K 38/26* (2006.01)
*C07K 14/605* (2006.01)
*A61P 1/16* (2006.01)
*A61P 3/04* (2006.01)
*A61K 9/00* (2006.01)
*A61K 38/00* (2006.01)

(52) U.S. Cl.
CPC .......... *C07K 14/605* (2013.01); *A61K 9/0019* (2013.01); *A61K 38/26* (2013.01); *A61P 1/16* (2018.01); *A61P 3/04* (2018.01); *A61K 38/00* (2013.01)

(58) Field of Classification Search
CPC .............................. C07K 14/605; A61K 9/0019
See application file for complete search history.

(56) References Cited

U.S. PATENT DOCUMENTS

2015/0307579 A1* 10/2015 Agoram ............... C07K 14/605
514/5.3

FOREIGN PATENT DOCUMENTS

| WO | WO 2011/006497 A1 | 1/2011 |
| WO | WO 2011/094337 A1 | 8/2011 |
| WO | WO 2012/050923 A2 | 4/2012 |
| WO | WO 2012/138941 A1 | 10/2012 |
| WO | WO 2014/091316 A2 | 6/2014 |

OTHER PUBLICATIONS

Lewis et al., Dig. Dis. Sci. 55: 560-578, (2010).*

* cited by examiner

*Primary Examiner* — Gyan Chandra

(57) ABSTRACT

Provided herein are methods of preventing and treating obesity and diabetes in patients comprising administering GLP-1/glucagon agonists peptides.

15 Claims, 31 Drawing Sheets
Specification includes a Sequence Listing.

FIG. 13

Part A:
Cohorts 1 through 3
Key endpoints:
Safety/tolerability and PK

Cohort 3: (6 MEDI0382 + 3 placebo)

| Initial dose<br>4 days | Titration dose 1<br>4 days | Titration dose 2<br>7 days |
|---|---|---|

Cohort 2: (6 MEDI0382 + 3 placebo)

| Initial dose<br>4 days | Titration dose 1<br>7 days |
|---|---|

Cohort 1: (6 MEDI0382 + 3 placebo)

| Stable dose<br>7 days |
|---|

Part B:
Cohort 4
Key endpoints:
Body weight, glycemic control, safety/tolerability 24 MEDI0382 + 24 placebo

| Initial dose<br>4 days | Titration dose 1<br>4 days | Titration Dose 2<br>4 days | Titration dose 2<br>28 days at home | Titration dose 2<br>1 day (inpatient) |
|---|---|---|---|---|

41 days dosing period per subject

FIG. 15
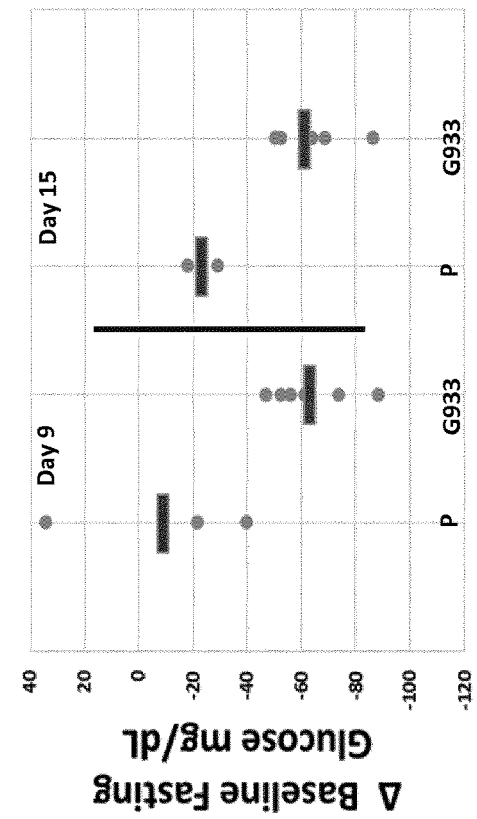
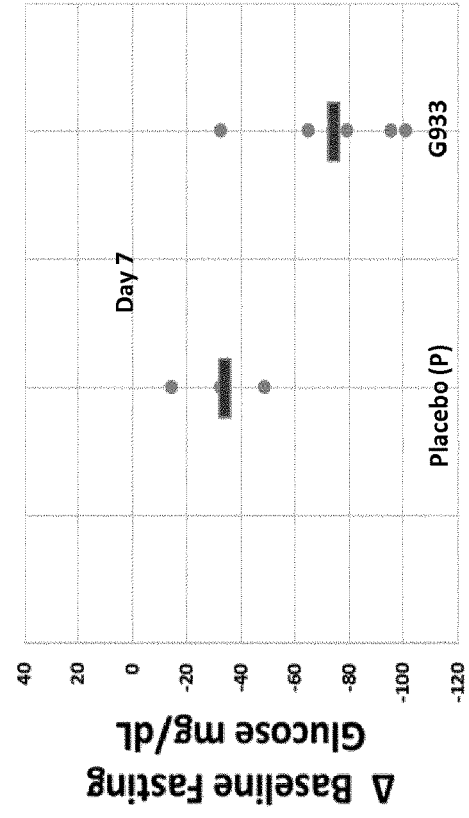

FIG. 16
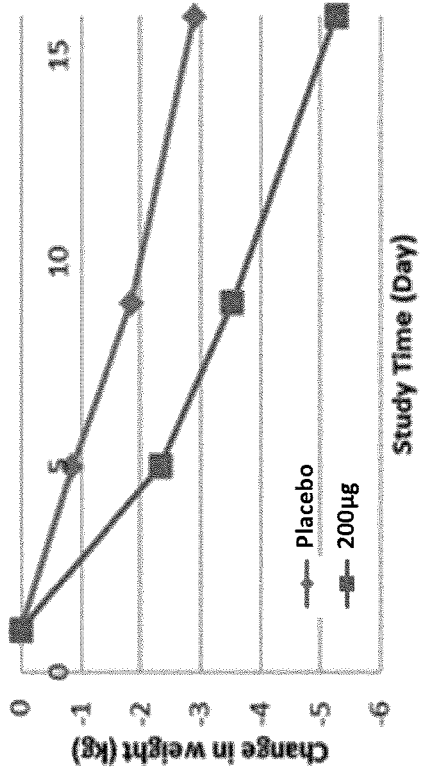
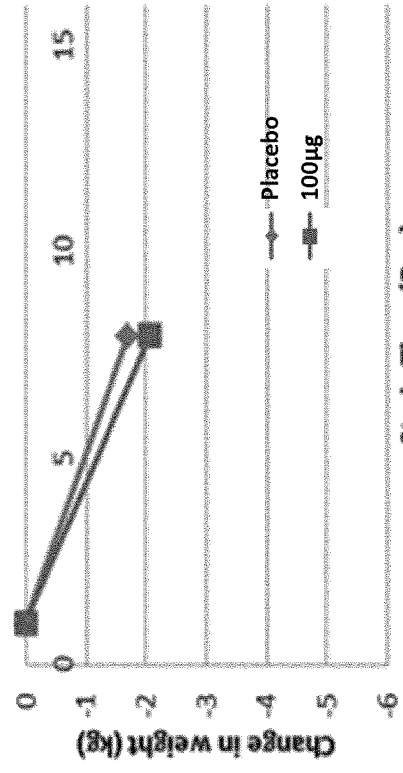
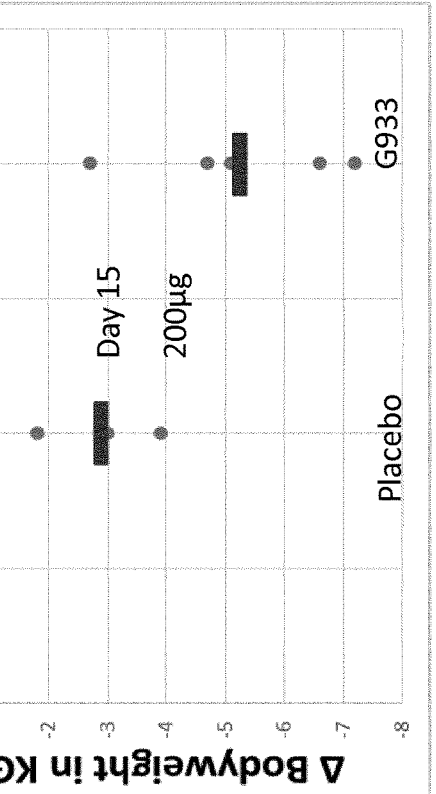
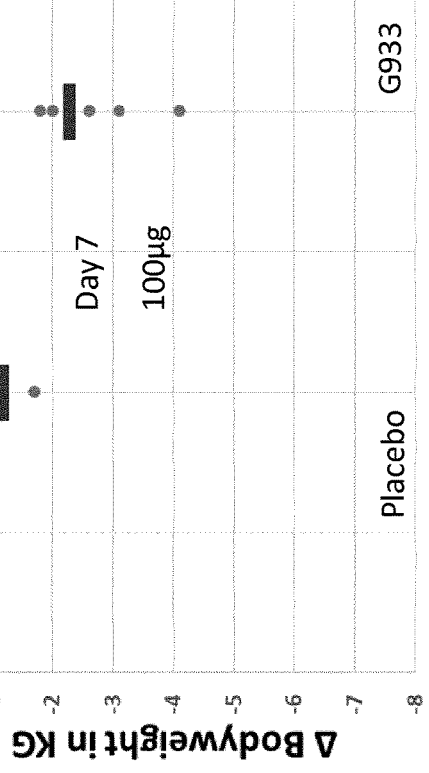

FIG. 22
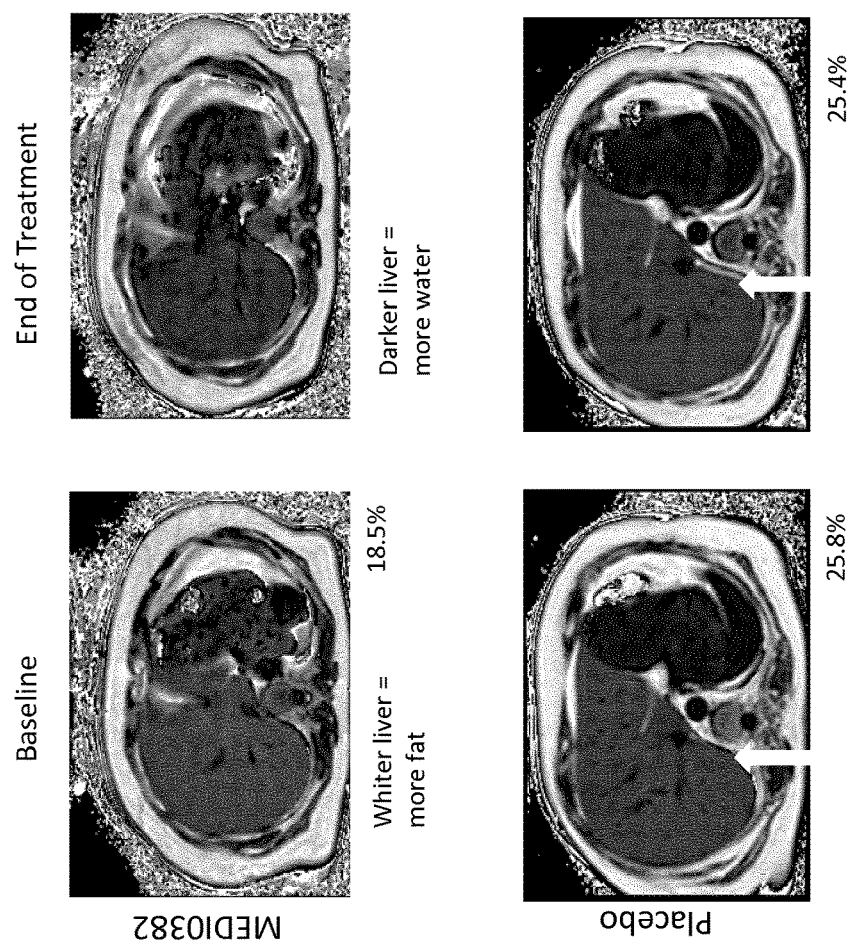
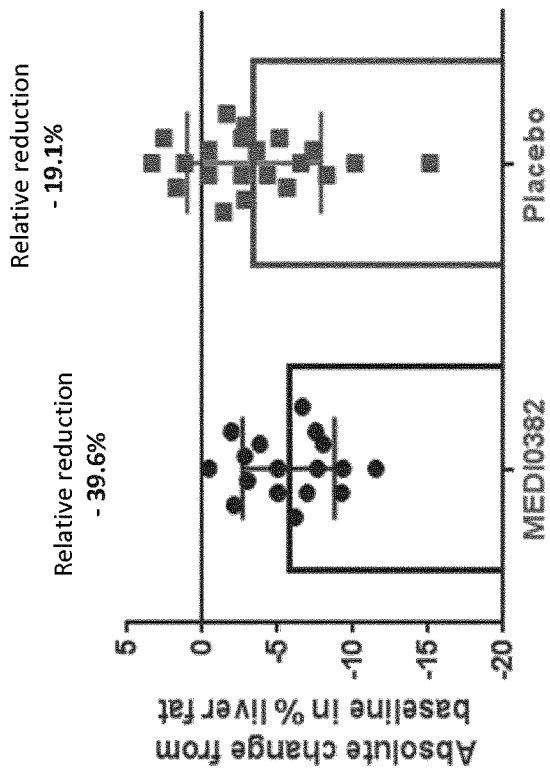

FIG. 24

*Cohort 5 -    12 active + 4 placebo*

| 100µg 5 days 3 inpatient | 150µg 5 days outpatient | 200µg 5 days outpatient | 300µg 7 days 3+1 inpatient |
|---|---|---|---|

*Cohort 6 -    12 active + 4 placebo*

| 100µg 5 days 3 inpatient | 200µg 5 days outpatient | 300µg 7 days 3+1 inpatient |
|---|---|---|

FIG. 28
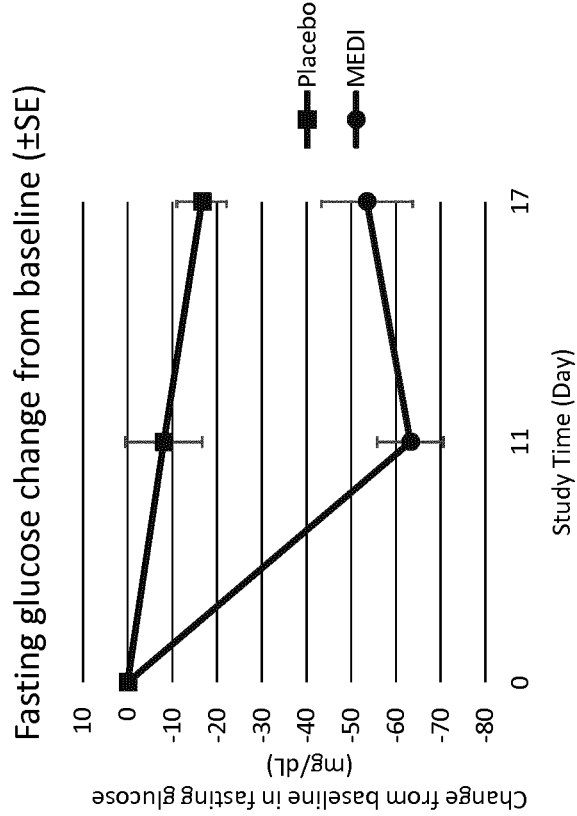
Cohort 6
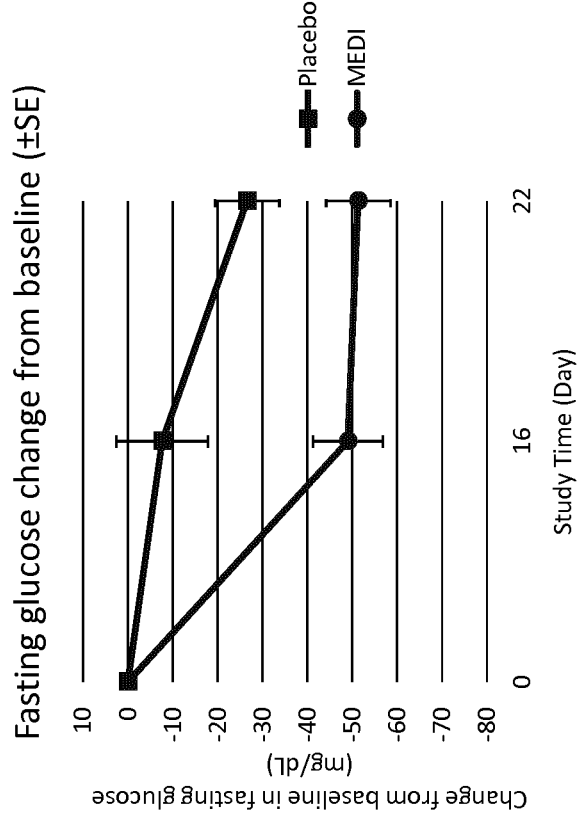
Cohort 5

FIG. 29
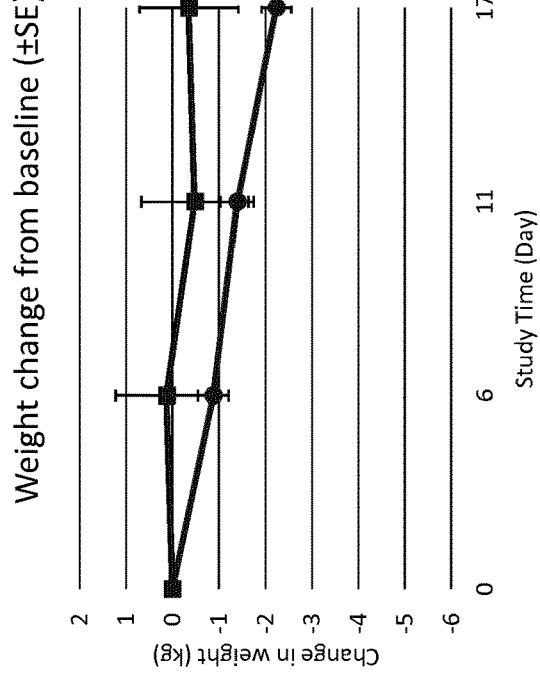
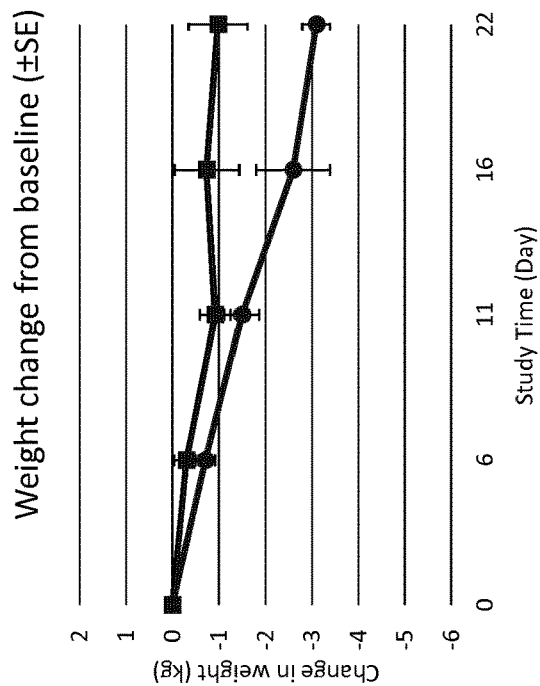

FIG. 30
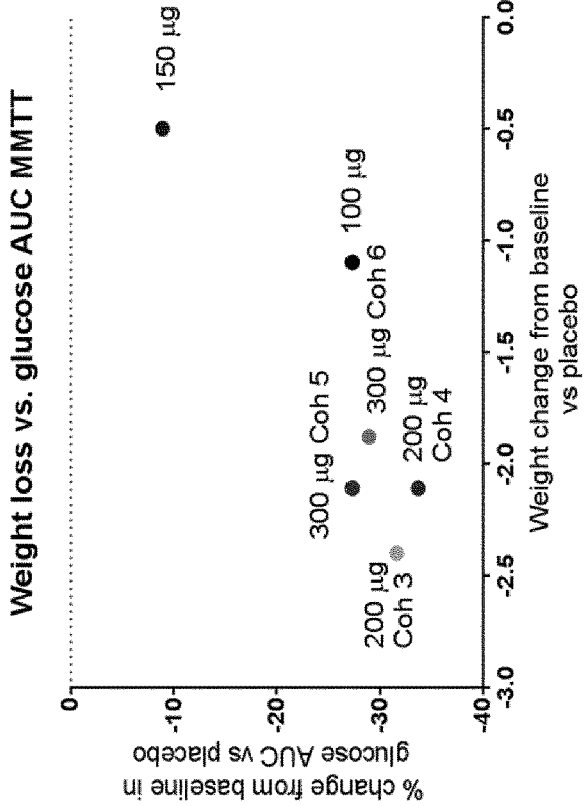
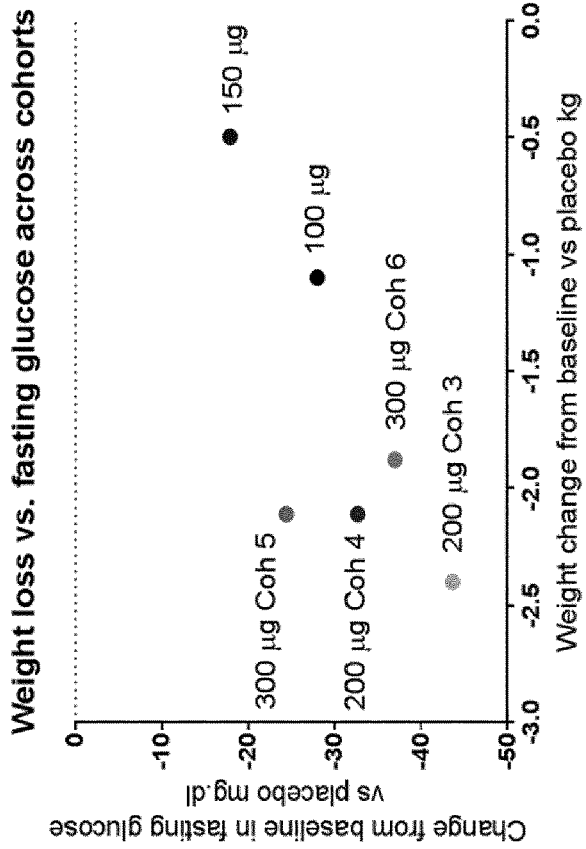

SEQUENCE LISTING

```
<160> NUMBER OF SEQ ID NOS: 26

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
```

```
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (2)..(2)
<223> OTHER INFORMATION: Xaa is Gly or Ser
<220> FEATURE:
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (15)..(15)
<223> OTHER INFORMATION: Xaa is Asp or Glu
<220> FEATURE:
<221> NAME/KEY: MISC_FEATURE
<222> LOCATION: (16)..(16)
<223> OTHER INFORMATION: Xaa is Ser or Gly
<220> FEATURE:
<221> NAME/KEY: MISC_FEATURE
<222> LOCATION: (17)..(17)
<223> OTHER INFORMATION: Xaa is Glu, Arg, Gln, or Lys
<220> FEATURE:
<221> NAME/KEY: MISC_FEATURE
<222> LOCATION: (18)..(18)
<223> OTHER INFORMATION: Xaa is Arg, Ser, or Ala
<220> FEATURE:
<221> NAME/KEY: MISC_FEATURE
<222> LOCATION: (20)..(20)
<223> OTHER INFORMATION: Xaa is Arg, Lys, or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (23)..(23)
<223> OTHER INFORMATION: Xaa is Val or Ile
<220> FEATURE:
<221> NAME/KEY: MISC_FEATURE
<222> LOCATION: (24)..(24)
<223> OTHER INFORMATION: Xaa is Ala or Gln
<220> FEATURE:
<221> NAME/KEY: MISC_FEATURE
<222> LOCATION: (27)..(27)
<223> OTHER INFORMATION: Xaa is Glu or Val
<220> FEATURE:
<221> NAME/KEY: MISC_FEATURE
<222> LOCATION: (28)..(28)
<223> OTHER INFORMATION: Xaa is Ala or Lys
<220> FEATURE:
<221> NAME/KEY: MISC_FEATURE
<222> LOCATION: (30)..(30)
<223> OTHER INFORMATION: Xaa is Gly or Arg

<400> SEQUENCE: 4

His Xaa Gln Gly Thr Phe Thr Ser Asp Xaa Ser Xaa Xaa Leu Xaa Xaa
1               5                   10                  15

Xaa Xaa Ala Xaa Xaa Phe Xaa Xaa Trp Leu Xaa Xaa Gly Xaa
            20                  25                  30

<210> SEQ ID NO 5
<211> LENGTH: 30
<212> TYPE: PRT
<213> ORGANISM: Artificial Sequence
```

```
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (17)..(17)
<223> OTHER INFORMATION: Xaa is Glu, Arg, Gln, or Lys
<220> FEATURE:
<221> NAME/KEY: MISC_FEATURE
<222> LOCATION: (18)..(18)
<223> OTHER INFORMATION: Xaa is Arg, Ser, or Ala
<220> FEATURE:
<221> NAME/KEY: MISC_FEATURE
<222> LOCATION: (27)..(27)
<223> OTHER INFORMATION: Xaa is Glu or Val

<400> SEQUENCE: 5

His Ser Gln Gly Thr Phe Thr Ser Asp Xaa Ser Xaa Xaa Leu Asp Ser
1               5                   10                  15

Xaa Xaa Ala Arg Asp Phe Val Ala Trp Leu Xaa Ala Gly Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (27)..(27)
<223> OTHER INFORMATION: Xaa is Glu or Val

<400> SEQUENCE: 6

His Ser Gln Gly Thr Phe Thr Ser Asp Xaa Ser Xaa Xaa Leu Asp Ser
1               5                   10                  15

Glu Arg Ala Arg Asp Phe Val Ala Trp Leu Xaa Ala Gly Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Xaa is Tyr or Lys
<220> FEATURE:
```

```
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (27)..(27)
<223> OTHER INFORMATION: Xaa is Glu or Val

<400> SEQUENCE: 7

His Ser Gln Gly Thr Phe Thr Ser Asp Xaa Ser Xaa Xaa Leu Asp Ser
1               5                   10                  15

Arg Ser Ala Arg Asp Phe Val Ala Trp Leu Xaa Ala Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 8

His Ser Gln Gly Thr Phe Thr Ser Asp Tyr Ser Lys Lys Leu Asp Ser
1               5                   10                  15

Glu Arg Ala Arg Asp Phe Val Ala Trp Leu Val Ala Gly Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 9

His Ser Gln Gly Thr Phe Thr Ser Asp Tyr Ser Lys Lys Leu Asp Ser
1               5                   10                  15

Arg Ser Ala Arg Asp Phe Val Ala Trp Leu Val Ala Gly Gly
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (12)..(12)
<223> OTHER INFORMATION: Xaa is Lys, Glu, or Arg

<400> SEQUENCE: 10

His Ser Gln Gly Thr Phe Thr Ser Asp Lys Ser Xaa Tyr Leu Asp Ser
1               5                   10                  15

Glu Arg Ala Arg Asp Phe Val Ala Trp Leu Glu Ala Gly Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: chimeric GLP-1/glucagon peptide
```

```
<220> FEATURE:
<221> NAME/KEY: MISC_FEATURE
<222> LOCATION: (12)..(12)
<223> OTHER INFORMATION: Xaa is Lys, Glu, Arg, or Ser

<400> SEQUENCE: 11

His Ser Gln Gly Thr Phe Thr Ser Asp Lys Ser Xaa Tyr Leu Asp Ser
1               5                   10                  15

Arg Ser Ala Arg Asp Phe Val Ala Trp Leu Glu Ala Gly Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 12

His Ser Gln Gly Thr Phe Thr Ser Asp Lys Ser Glu Tyr Leu Asp Ser
1               5                   10                  15

Glu Arg Ala Arg Asp Phe Val Ala Trp Leu Glu Ala Gly Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 13

His Ser Gln Gly Thr Phe Thr Ser Asp Lys Ser Glu Tyr Leu Asp Ser
1               5                   10                  15

Arg Ser Ala Arg Asp Phe Val Ala Trp Leu Glu Ala Gly Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 14

His Ser Gln Gly Thr Phe Thr Ser Asp Lys Ser Arg Tyr Leu Asp Ser
1               5                   10                  15

Glu Arg Ala Arg Asp Phe Val Ala Trp Leu Glu Ala Gly Gly
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 15

His Ser Gln Gly Thr Phe Thr Ser Asp Lys Ser Arg Tyr Leu Asp Ser
1               5                   10                  15

Arg Ser Ala Arg Asp Phe Val Ala Trp Leu Glu Ala Gly Gly
            20                  25                  30

<210> SEQ ID NO 16
```

-continued

```
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (13)..(13)
<223> OTHER INFORMATION: Lysine with a palmitoyl group conjugated to the
      epsilon nitrogen, through a gamma glutamic acid linker

<400> SEQUENCE: 16

His Ser Gln Gly Thr Phe Thr Ser Asp Tyr Ser Lys Lys Leu Asp Ser
1               5                   10                  15

Glu Arg Ala Arg Asp Phe Val Ala Trp Leu Val Ala Gly Gly
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 17

His Ser Gln Gly Thr Phe Thr Ser Asp Lys Ser Glu Tyr Leu Asp Ser
1               5                   10                  15

Glu Arg Ala Arg Asp Phe Val Ala Trp Leu Glu Ala Gly Gly
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 18

His Ser Gln Gly Thr Phe Thr Ser Asp Lys Ser Arg Tyr Leu Asp Ser
1               5                   10                  15

Arg Ser Ala Arg Asp Phe Val Ala Trp Leu Glu Ala Gly Gly
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 19

His Ser Gln Gly Thr Phe Thr Ser Asp Lys Ser Glu Tyr Leu Asp Ser
1               5                   10                  15
```

Glu Arg Ala Arg Asp Phe Val Ala Trp Leu Glu Ala Gly Gly
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 20

His Ser Gln Gly Thr Phe Thr Ser Asp Lys Ser Ser Tyr Leu Asp Ser
1               5                   10                  15

Arg Ser Ala Arg Asp Phe Val Ala Trp Leu Glu Ala Gly Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 21

His Ser Gln Gly Thr Phe Thr Ser Asp Lys Ser Ser Tyr Leu Asp Ser
1               5                   10                  15

Arg Arg Ala Arg Asp Phe Val Ala Trp Leu Glu Ala Gly Gly
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 22

His Ser Gln Gly Thr Phe Thr Ser Asp Lys Ser Lys Tyr Leu Glu Gly
1               5                   10                  15

Gln Ala Ala Lys Glu Phe Ile Ala Trp Leu Glu Lys Gly Arg
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (17)..(17)
<223> OTHER INFORMATION: Lysine with a palmitoyl group conjugated to the
      epsilon nitrogen, through a gamma glutamic acid linker

```
<400> SEQUENCE: 23

His Gly Gln Gly Thr Phe Thr Ser Asp Tyr Ser Lys Tyr Leu Asp Ser
1               5                   10                  15

Lys Arg Ala Gln Asp Phe Val Gln Trp Leu Val Ala Gly Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: G931
<220> FEATURE:
<221> NAME/KEY: MISC_FEATURE
<222> LOCATION: (13)..(13)
<223> OTHER INFORMATION: Lysine with a palmitoyl group conjugated to the
      epsilon nitrogen, through a gamma glutamic acid linker

<400> SEQUENCE: 24

His Ser Gln Gly Thr Phe Thr Ser Asp Tyr Ser Lys Lys Leu Asp Ser
1               5                   10                  15

Glu Arg Ala Arg Asp Phe Val Ala Trp Leu Val Ala Gly Gly
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: G934
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 25

His Ser Gln Gly Thr Phe Thr Ser Asp Lys Ser Lys Tyr Leu Glu Gly
1               5                   10                  15

Gln Ala Ala Lys Glu Phe Ile Ala Trp Leu Glu Lys Gly Arg
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: G973
<220> FEATURE:
<221> NAME/KEY: MISC_FEATURE
<222> LOCATION: (10)..(10)
<223> OTHER INFORMATION: Lysine with a palmitoyl group conjugated to the
      epsilon nitrogen, through a gamma glutamic acid linker

<400> SEQUENCE: 26

His Ser Gln Gly Thr Phe Thr Ser Asp Lys Ser Ser Tyr Leu Asp Ser
1               5                   10                  15

Arg Ser Ala Arg Asp Phe Val Ala Trp Leu Glu Ala Gly Gly
            20                  25                  30
```

GLUCAGON AND GLP-1 CO-AGONISTS FOR THE TREATMENT OF OBESITY

CROSS-REFERENCE TO RELATED APPLICATIONS

This application is a U.S. National Stage application of International Application No. PCT/EP2017/055679, filed on Mar. 10, 2017, said International Application No. PCT/EP2017/055679 claims benefit under 35 U.S.C. § 119(e) of the U.S. Provisional Application No. 62/306,121, filed Mar. 10, 2016. Each of the above listed applications is incorporated by reference herein in its entirety for all purposes.

REFERENCE TO SEQUENCE LISTING SUBMITTED ELECTRONICALLY

The content of the electronically submitted sequence listing in ASCII text file (Name: Sequencelisting_ST25.txt; Size: 14,333 bytes; and Date of Creation: Mar. 6, 2017) filed with the application is incorporated herein by reference in its entirety.

BACKGROUND

Obesity is a major and growing health problem worldwide. It is associated with many life-threatening diseases such as cardiovascular disease, renal disease, hypertension, stroke, infertility, respiratory dysfunction, and type 2 diabetes.

Glucagon and glucagon-like peptide-1 (GLP-1) derive from pre-proglucagon, a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of proglucagon (53 to 81 of preproglucagon), while GLP-1 is produced as a 37-amino acid peptide that corresponds to amino acids 72 through 108 of proglucagon (92 to 128 of preproglucagon). GLP-1(7-36) amide or GLP-1(7-37) acid are biologically active forms of GLP-1, that demonstrate essentially equivalent activity at the GLP-1 receptor.

Glucagon is produced by the pancreas and interacts with the glucagon receptor ("glucR"). Glucagon acts in the liver to raise blood glucose via gluconeogenesis and glycogenolysis. When blood glucose begins to fall, glucagon signals the liver to break down glycogen and release glucose, causing blood glucose levels to rise toward a normal level.

GLP-1 has different biological activities compared to glucagon. It is secreted from gut L cells and binds to the GLP-1 receptor. Its activities include stimulation of insulin synthesis and secretion, inhibition of glucagon secretion, and inhibition of food intake.

Both glucagon and GLP-1, acting as agonists at their respective receptors, have been shown to be effective in weight loss. Certain GLP-1 analogs are being sold or are in development for treatment of obesity including, e.g., Liraglutide (VICTOZA® from Novo Nordisk) and Exenatide (Byetta® from Eli Lilly/Amylin). Glucagon/GLP-1 agonist peptides have also been disclosed in WO 2014/091316.

While some therapies are available for the control of blood glucose, none currently achieve substantial weight loss, which remains a significant unmet need for patients. Fifty percent of patients progress from oral monotherapy for glucose control (usually with metformin) to initiation of insulin within 10 years, often taking multiple oral combination therapies before initiating insulin. The use of insulin exacerbates weight gain, which can be as great as 6 kg in the first year after starting insulin therapy. This weight gain can lead to increased insulin resistance, which is associated with hypertension, dyslipidemia, and an increased risk of major adverse cardiovascular events. With respect to reducing insulin resistance, significant weight loss (>5%) is the optimal intervention to reduce insulin resistance, although this can only be achieved reliably at present through intensive dietary and lifestyle interventions and/or bariatric surgery. There remains a need for methods of administering GLP-1/Glucagon agonist peptides to humans using dosage regimens that are therapeutically effective in treating diabetes and obesity but avoid adverse effects.

BRIEF SUMMARY

Provided herein are methods of preventing and treating obesity and diabetes and related conditions in patients comprising administering GLP-1/glucagon agonist peptides.

In one instance, a method of reducing body weight comprises administering to a human subject in need thereof 50-600 µg or 100-600 µg of a peptide comprising the amino acid sequence of $HX_2QGTFTSDX_{10}SX_{12}X_{13}LX_{15}X_{16}X_{17}X_{18}AX_{20}X_{21}FX_{23}X_{24}WLX_{27}X_{28}GX_{30}$; wherein $X_2$ is G or S, $X_{10}$ is Y or K, $X_{12}$ is K, E, R, or S, $X_{13}$ is K or Y, $X_{15}$ is D or E, $X_{16}$ is S or G, $X_{17}$ is E, R, Q, or K, $X_{18}$ is R, S, or A, $X_{20}$ is R, K, or Q, $X_{21}$ is D or E, $X_{23}$ is V or I, $X_{24}$ is A or Q, $X_{27}$ is E or V, $X_{28}$ is A or K, and $X_{30}$ is G or R (SEQ ID NO:4).

In one instance, a method of reducing body fat comprises administering to a human subject in need thereof 50-600 µg or 100-600 µg of a peptide comprising the amino acid sequence of SEQ ID NO:4.

In one instance, a method of treating obesity comprises administering to a human subject in need thereof 50-600 µg or 100-600 µg of a peptide comprising the amino acid sequence of SEQ ID NO:4.

In one instance, a method of treating or preventing a disease or condition caused or characterized by excess body weight comprises administering to a human subject in need thereof 50-600 µg or 100-600 µg of a peptide comprising the amino acid sequence of SEQ ID NO:4.

In one instance, a method of managing weight comprises administering to a human subject in need thereof 50-600 µg or 100-600 µg of a peptide comprising the amino acid sequence of SEQ ID NO:4.

In one instance, a method of treating Nonalcoholic Steatohepatitis (NASH) comprises administering to a human subject in need thereof 50-600 µg or 100-600 µg of a peptide comprising the amino acid sequence of SEQ ID NO:4.

In one instance, a method of increasing lipid oxidation comprises administering to a human subject in need thereof 50-600 µg or 100-600 µg of a peptide comprising the amino acid sequence of SEQ ID NO:4.

In one instance, a method of reducing food intake comprises administering to a human subject in need thereof 50-600 µg or 100-600 µg of a peptide comprising the amino acid sequence of SEQ ID NO:4.

In one instance, a method of lowering plasma glucose comprises administering to a human subject in need thereof 50-600 µg or 100-600 µg of a peptide comprising the amino acid sequence of SEQ ID NO:4.

In one instance, a method of improving glycemic control comprises administering to a human subject in need thereof 50-600 μg or 100-600 μg of a peptide comprising the amino acid sequence of SEQ ID NO:4.

In one instance, a method of achieving glycemic control comprises administering to a human subject in need thereof 50-600 μg or 100-600 μg of a peptide comprising the amino acid sequence of SEQ ID NO:4.

In one instance, a method of decreasing weight and controlling glucose comprises administering to a human subject in need thereof 50-600 μg or 100-600 μg of a peptide comprising the amino acid sequence of SEQ ID NO:4.

In one instance, the subject has diabetes. In one instance, the diabetes is type 2 diabetes mellitus.

In one instance, a method of treating type 2 diabetes mellitus comprises administering to a human a peptide comprising the amino acid sequence of SEQ ID NO:4.

In one instance, a method of improving glycemic control in a human subject with type 2 diabetes mellitus comprises administering to the subject 50-600 μg or 100-600 μg of a peptide comprising the amino acid sequence of SEQ ID NO:4.

In one instance, the administering reduces body weight. In one instance, the administering treats obesity. In one instance, the administration reduces body fat.

In one instance, $X_2$ is G, $X_{10}$ is K, $X_{12}$ is E, R, or S, $X_{13}$ is K, $X_{17}$ is E or K, $X_{18}$ is S, $X_{20}$ is R, $X_{27}$ is E, or $X_{28}$ is A.

In one instance, $X_2$ is G, $X_{10}$ is K, $X_{12}$ is E, R, or S, $X_{13}$ is K, $X_{17}$ is E or K, $X_{18}$ is S, $X_{20}$ is R, $X_{27}$ is E, and $X_{28}$ is A.

In one instance, the peptide comprises, consists essentially of, or consists of the amino acid sequence of SEQ ID NO:19.

In one instance, the administration comprises administering an initial dose for 3 to 10 days and a second higher dose thereafter.

In one instance, the initial dose is administered for 3 to 7 days. In one instance, the initial dose is 100 μg of the peptide. In one instance, the second dose is administered for at least four days. In one instance, the initial dose is administered for four consecutive days and the second dose is administered for at least four consecutive days. In one instance, the second dose is 150-200 μg of the peptide. In one instance, the second dose is 150 μg of the peptide or 200 μg of the peptide.

In one instance, the administration further comprises administering a third dose after the second dose, wherein the third dose is higher than the second dose. In one instance, the initial dose is administered for 3 to 10 days and the second dose is administered for 3 to 10 days. In one instance, the initial dose is administered for 3 to 7 days and the second dose is administered for 3 to 7 days. In one instance, the initial dose is administered for four consecutive days, the second dose is administered for four consecutive days, and the third dose is administered for at least four consecutive days. In one instance, the initial dose is administered for four consecutive days, the second dose is administered for seven consecutive days, and the third dose is administered for at least four consecutive days. In one instance, the third dose is 200-400 μg of the peptide. In one instance, the third dose is 200 μg of the peptide, 300 μg of the peptide, or 400 μg of the peptide.

In one instance, an initial dose of 100 μg is administered for four days, a second dose of 150 μg is administered for four days, and a third dose of 200 μg is subsequently administered daily. In one instance, an initial dose of 100 μg is administered for five days, a second dose of 150 μg is administered for five days, and a third dose of 200 μg is administered for five days, and a fourth dose of 300 μg is subsequently administered daily. In one instance, an initial dose of 100 μg is administered for five days, a second dose of 200 μg is administered for five days, and a third dose of 300 μg is subsequently administered daily.

In one instance, 50 μg of the peptide is administered. In one instance, 100 μg of the peptide is administered. In one instance, 150 μg of the peptide is administered. In one instance, 200 μg of the peptide is administered. In one instance, 250 μg of the peptide is administered. In one instance, 300 μg of the peptide is administered. In one instance, 400 μg of the peptide is administered.

In one instance, the peptide is administered daily. In one instance, the peptide is administered once daily.

In one instance, the peptide is administered for at least one week, for at least two weeks, for at least three weeks, or for at least four weeks.

In one instance, the peptide is administered by injection. In one instance, the administration is subcutaneous.

In one instance, the administration results in at least 20% reduction in glucose area under the concentration-time curve after a mixed-meal test.

In one instance, glucose is reduced. In one instance, the glucose is fasting plasma glucose. In one instance, the glucose is postprandial glucose from a mixed-meal test.

In one instance, the administration results in weight loss of at least 1.0 kg, at least 1.3 kg, or about 1.3 to about 2.0 kg. In one instance, the subject's weight is reduced by at least 3.5 kg or at least 5 kg. In one instance, the subject's weight is reduced by at least 2%, at least 4%, at least 5%, or at least 10%. In one instance, the subject's weight is reduced by about 2% to about 20%, about 2% to about 25%, or about 2% to about 30%.

In one instance, the fat is liver fat. In one instance, liver fat in the subject is reduced by at least 20%. In one instance, liver fat in the subject is reduced by about 20% to about 40%. In one instance, the administration results in about a one third reduction in liver fat. In one instance, liver volume is reduced in the subject.

In one instance, the administration reduces hemoglobin A1c (HbA1c) levels. In one instance, the HbA1c level in the subject is reduced by at least 0.6%. In one instance, the HbA1c level in the subject is reduced by at least 0.9%. In one instance, the HbA1c level in the subject is reduced by about 0.5% to about 1.5%, about 0.5% to about 2%, or about 0.5% to about 3%. In one instance, the HbA1c level in the subject is reduced to 6.3% or lower.

In one instance, the administration reduces fructosamine levels.

In one instance, the subject's appetite is reduced.

In one instance, the subject's energy expenditure is increased.

In one instance, disease progression is stopped. In one instance, disease progression is reversed.

In one instance, the peptide is manufactured synthetically by solid-phase synthesis. In one instance, the solid-phase synthesis uses fluorenylmethyloxycarbonyl chloride chemistry.

In one instance, the carboxyl group of $X_{30}$ in the peptide is unmodified G or R. In one instance, the carbonyl group of $X_{30}$ in the peptide is amidated.

In one instance, the peptide comprises a palmitoyl moiety on the N(epsilon) group of a lysine residue. In one instance, the palmitoyl group is linked to the lysine via a linker. In one instance, the linker is gamma glutamate. In one instance, the peptide comprises a stearoyl or sterate moiety on the N(epsilon) group of a lysine residue. In one instance, the lysine residue is $X_{10}$.

In one instance, the peptide binds to a human glucagon receptor with an EC50 in the cAMP assay 1 of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In one instance, the peptide binds to a human GLP-1 receptor with an EC50 in the cAMP assay 1 of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In one instance, the peptide is an agonist of GLP-1 activity, an agonist of glucagon activity, or an agonist of both GLP-1 and glucagon activity.

In one instance, the peptide binds to both a glucagon receptor and a GLP-1 receptor, wherein the peptide exhibits at least about 2-fold, 5-fold, or 10-fold greater activity relative to the natural ligand at the GLP-1 receptor than at the glucagon receptor.

In one instance, the peptide further comprises a heterologous moiety. In one instance, the heterologous moiety is a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, a lipid, or a combination of two or more of the recited moieties.

In one instance, the subject has a body mass index (BMI) of 27 to 40 kg/m$^2$. In one instance, the subject has a BMI of 30-39.9 kg/m$^2$. In one instance, the subject has a BMI of at least 40 kg/m$^2$.

In one instance, the subject is overweight. In one instance, the subject is obese. In one instance, the subject is (i) overweight and (ii) has hypertension, Type 2 diabetes mellitus, dyslipidemia, a history of cardiovascular disease or a combination of thereof. In one instance, the subject is (i) overweight and (ii) has dysglycaemia, hypertension, dyslipidemia, obstructive sleep apnea, or a combination of thereof.

In one instance, the subject is receiving insulin therapy. In one instance, the amount of insulin administered is reduced. In one instance, the insulin therapy is stopped.

In one instance, the subject is receiving insulin, metformin, sulphonylurea, a sodium-glucose cotransporter-2 (sglt-2) inhibitor, a Dipeptidyl peptidase-4 (DPP-IV) inhibitor, glutazone, an alpha glucosidase inhibitor, or a combination thereof.

In one instance, the half-life of the peptide is about 10 to about 12 hours.

In one instance, the administration is an adjunct to diet and exercise.

In one instance, the peptide comprises SEQ ID NO:19, and the peptide is administered at an initial dose of 100 μg for four days, at a second dose of 150 ug for four days, and subsequently at a dose of 200 μg daily.

In one instance, the peptide comprises SEQ ID NO:19, and the peptide is administered at an initial dose of 100 μg for five days, at a second dose of 200 ug for five days, and subsequently at a dose of 300 μg daily.

In one instance, the peptide comprises SEQ ID NO:19, and the peptide is administered at an initial dose of 100 μg for five days, at a second dose of 150 ug for five days, at a second dose of 200 ug for five days, and subsequently at a dose of 300 μg daily.

In one instance, the subject has type 2 diabetes mellitus. In one instance, the subject is obese. In one instance, the subject is (i) overweight and (ii) has hypertension, Type 2 diabetes mellitus, dyslipidemia, a history of cardiovascular disease or a combination of thereof. In one instance, the subject is (i) overweight and (ii) has dysglycaemia, hypertension, dyslipidemia, obstructive sleep apnea, or a combination of thereof.

BRIEF DESCRIPTION OF THE DRAWINGS/FIGURES

FIG. 1 shows the mean percent of change in body weight from day zero in DIO mice following administration of glucagon/GLP-1 co-agonist peptide G730 at three different doses, compared to vehicle treatment, and treatment with Liraglutide. Starting body weight in the different groups were vehicle: 47.4±3.7 g, G730 10 nmol/kg: 44.5±2.2 g, G730 20 nmol/kg: 45.9±3.6 g and G730 50 nmol/kg: 46.1±2.4 g, respectively.

FIG. 2 shows the mean percent of change in body weight from day zero in DIO mice following administration of glucagon/GLP-1 co-agonist peptide G797 at three different doses, compared to vehicle treatment, and treatment with Liraglutide. Starting body weight in the different groups were vehicle: 47.4±3.7 g, G797 5 nmol/kg: 47.5±1.2 g, G797 20 nmol/kg: 47.4±2.2 g and G797 50 nmol/kg: 47.2±1.8 g, respectively.

Figure 1:
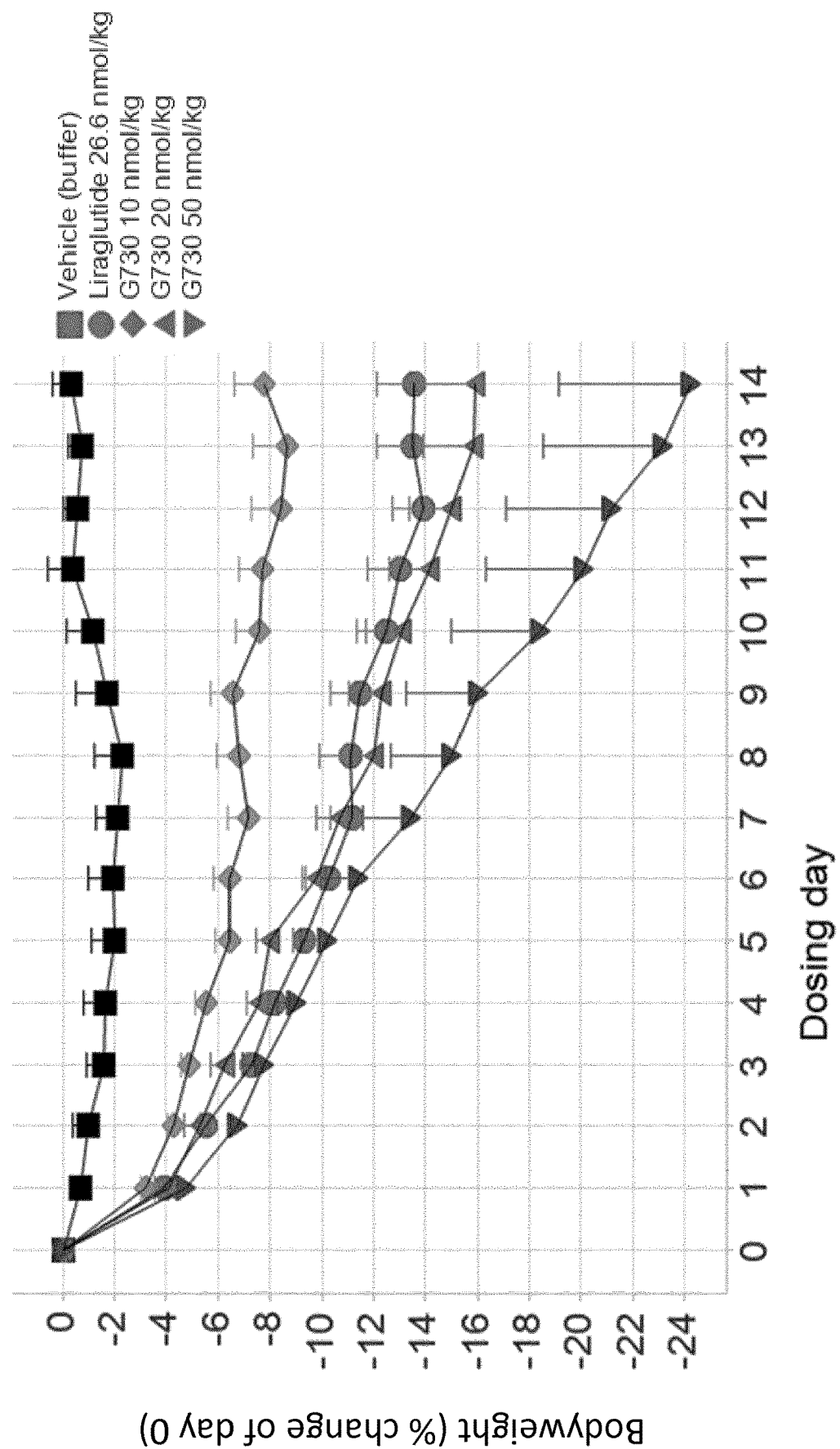
Figure 2:
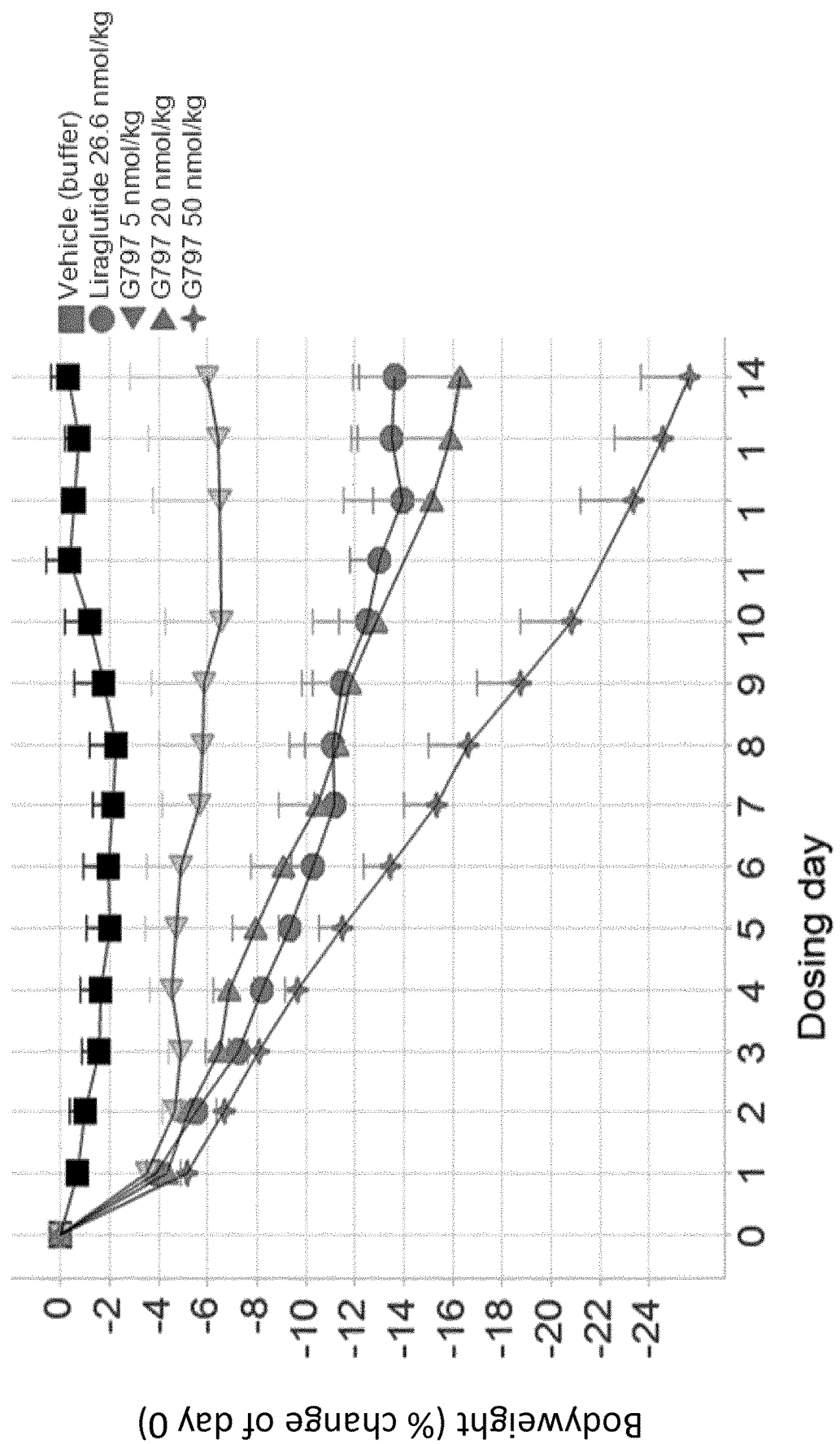
Figure 3:
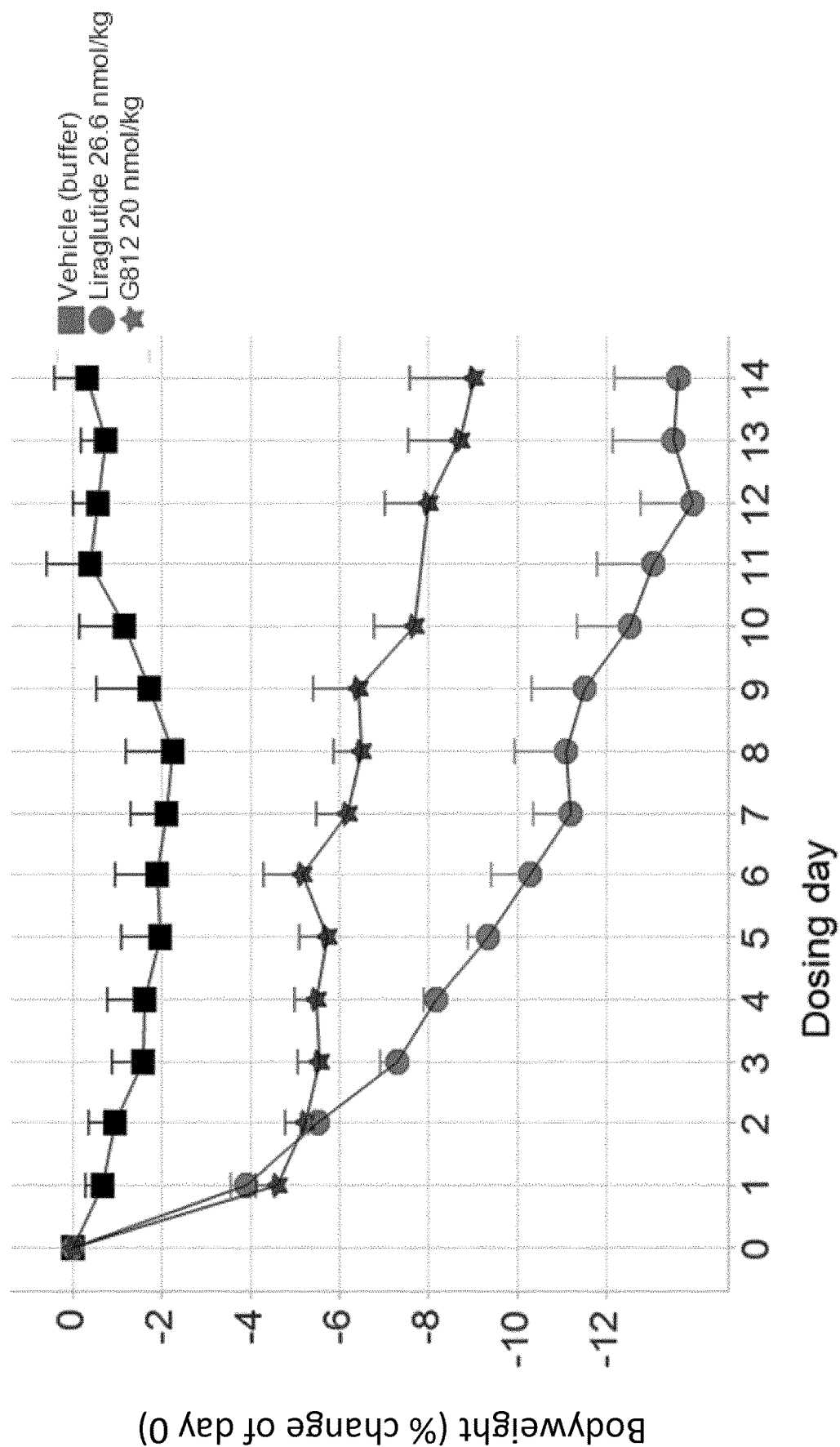
FIG. 3 shows the mean percent of change in body weight from day zero in DIO mice following administration of glucagon/GLP-1 co-agonist peptide G812 at a dose of 20 nmol/kg, compared to vehicle treatment, and treatment with Liraglutide. Starting body weight in the different groups were vehicle: 47.4±3.7 g and G812 20 nmol/kg: 49.2±3.4 g, respectively.
Figure 4:
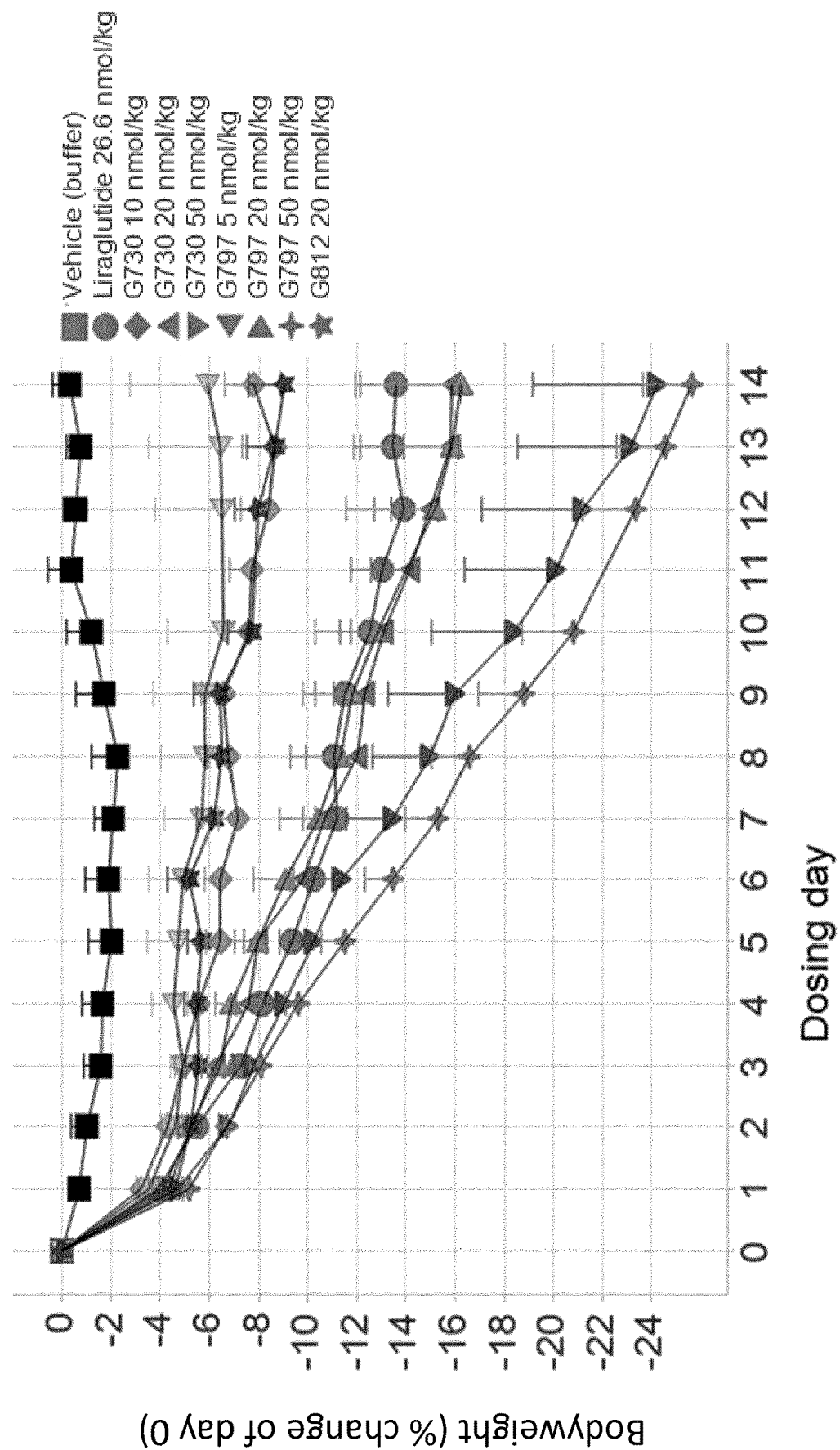
FIG. 4 is a graph comparing the change in body weight results for the three glucagon/GLP-1 co-agonist peptides presented in FIGS. 1, 2, and 3.
Figure 5:
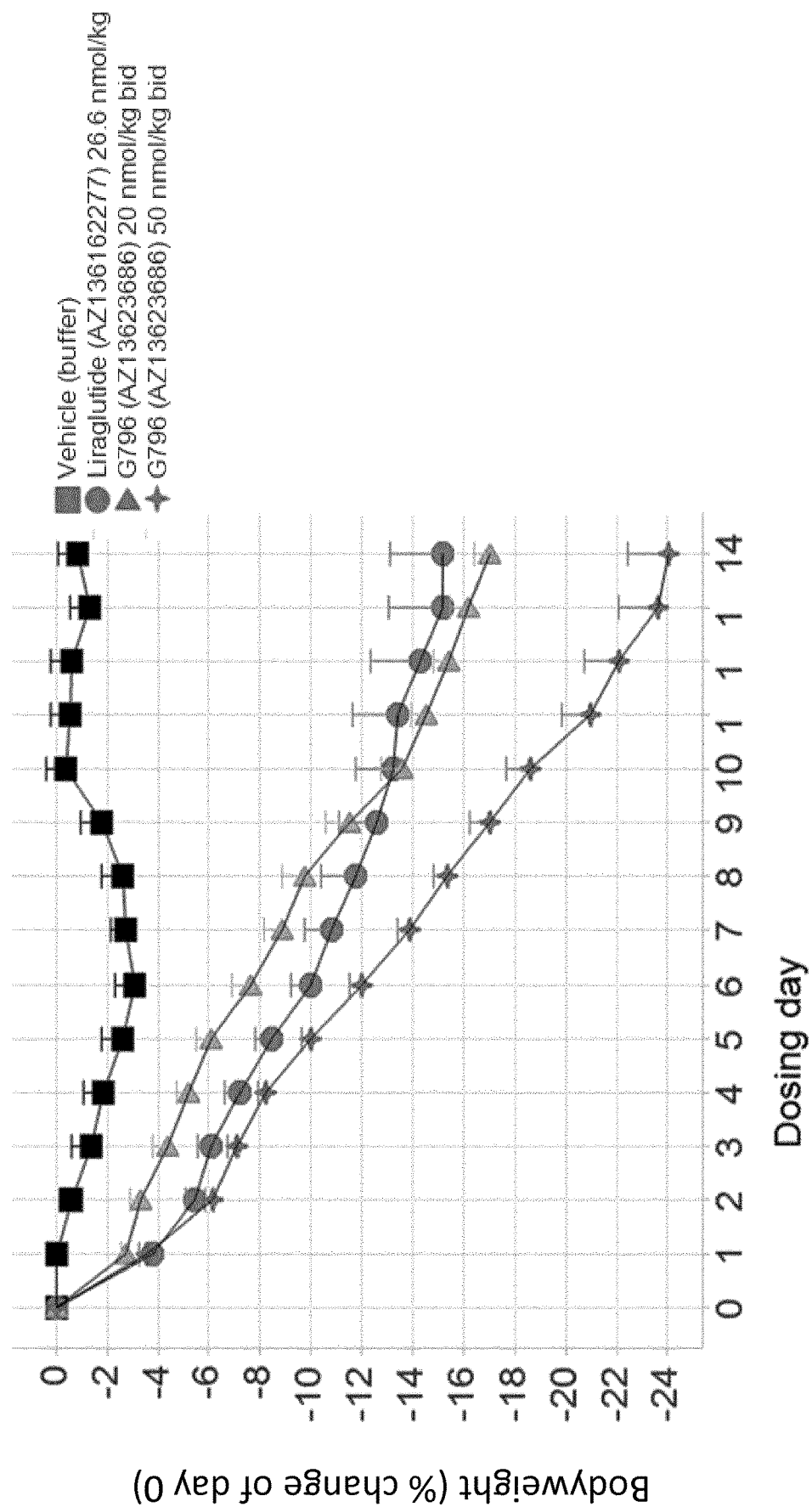
FIG. 5 shows the mean percent of change in body weight from day zero in DIO mice following administration of glucagon/GLP-1 co-agonist peptide G796 at two different doses, compared to vehicle treatment, and treatment with Liraglutide.
Figure 6:
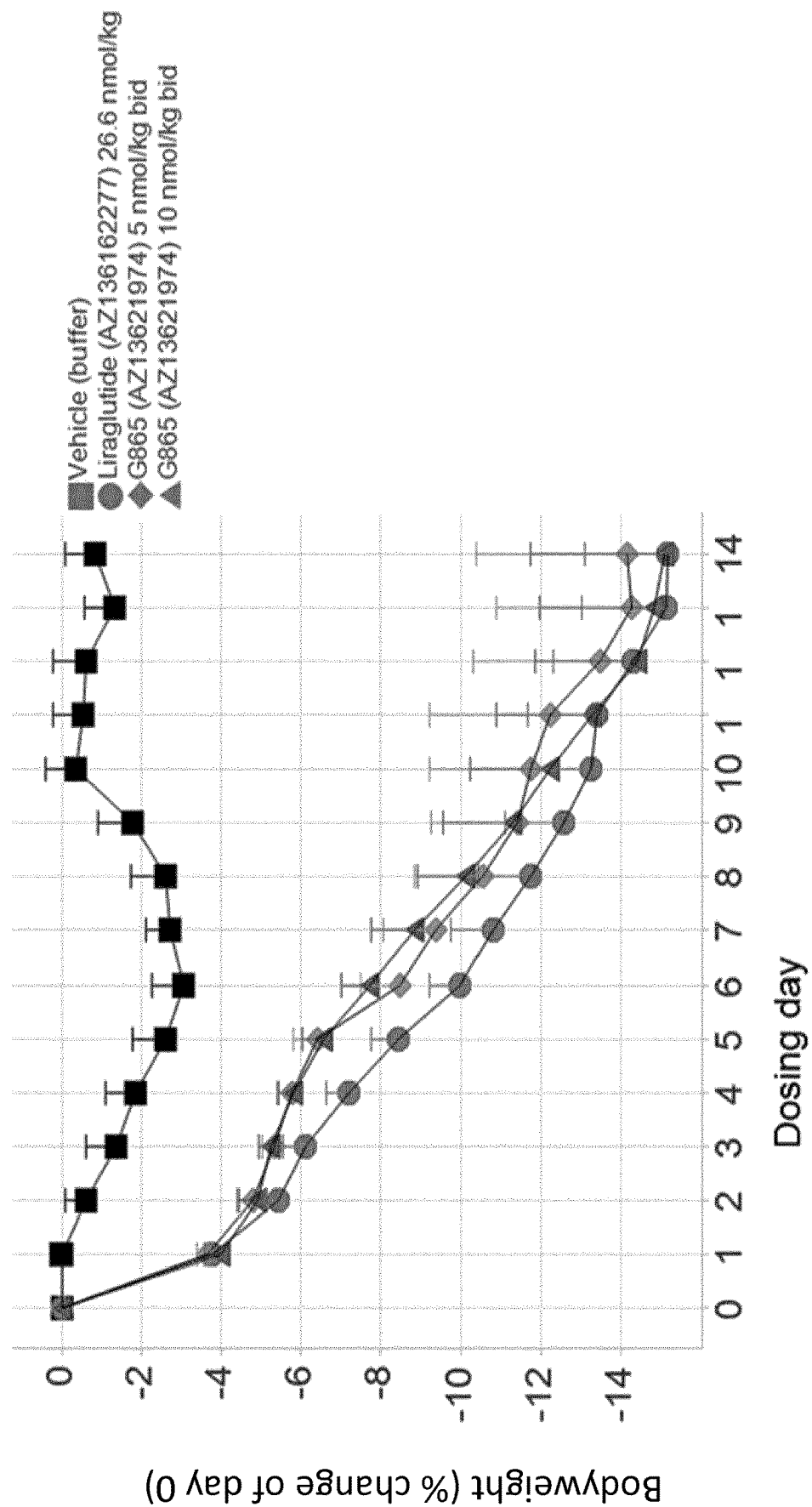
FIG. 6 shows the mean percent of change in body weight from day zero in DIO mice following administration of glucagon/GLP-1 co-agonist peptide G865 at two different doses, compared to vehicle treatment, and treatment with Liraglutide.
Figure 7:
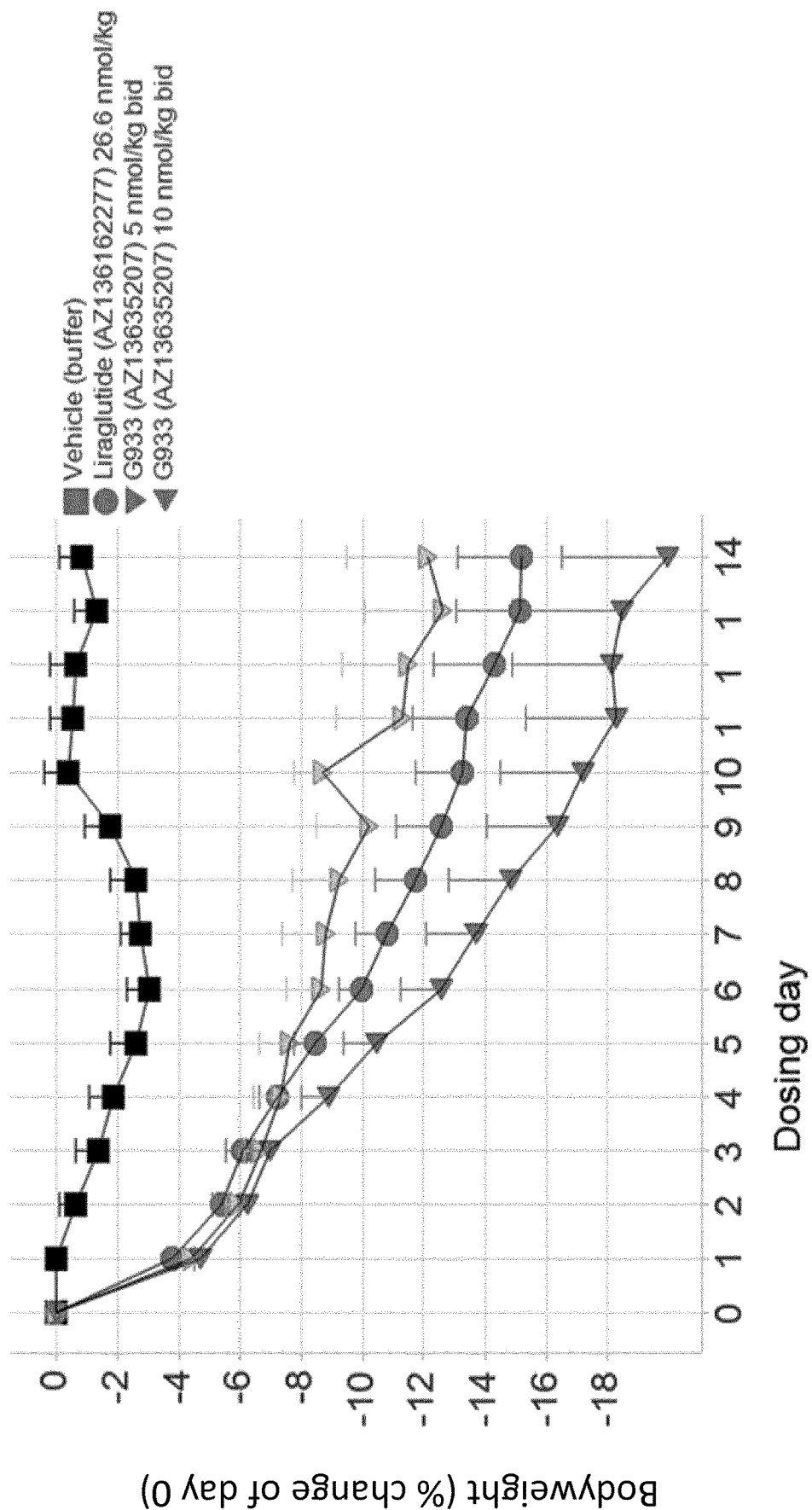
FIG. 7 shows the mean percent of change in body weight from day zero in DIO mice following administration of glucagon/GLP-1 co-agonist peptide G933 at two different doses, compared to vehicle treatment, and treatment with Liraglutide.
Figure 8:
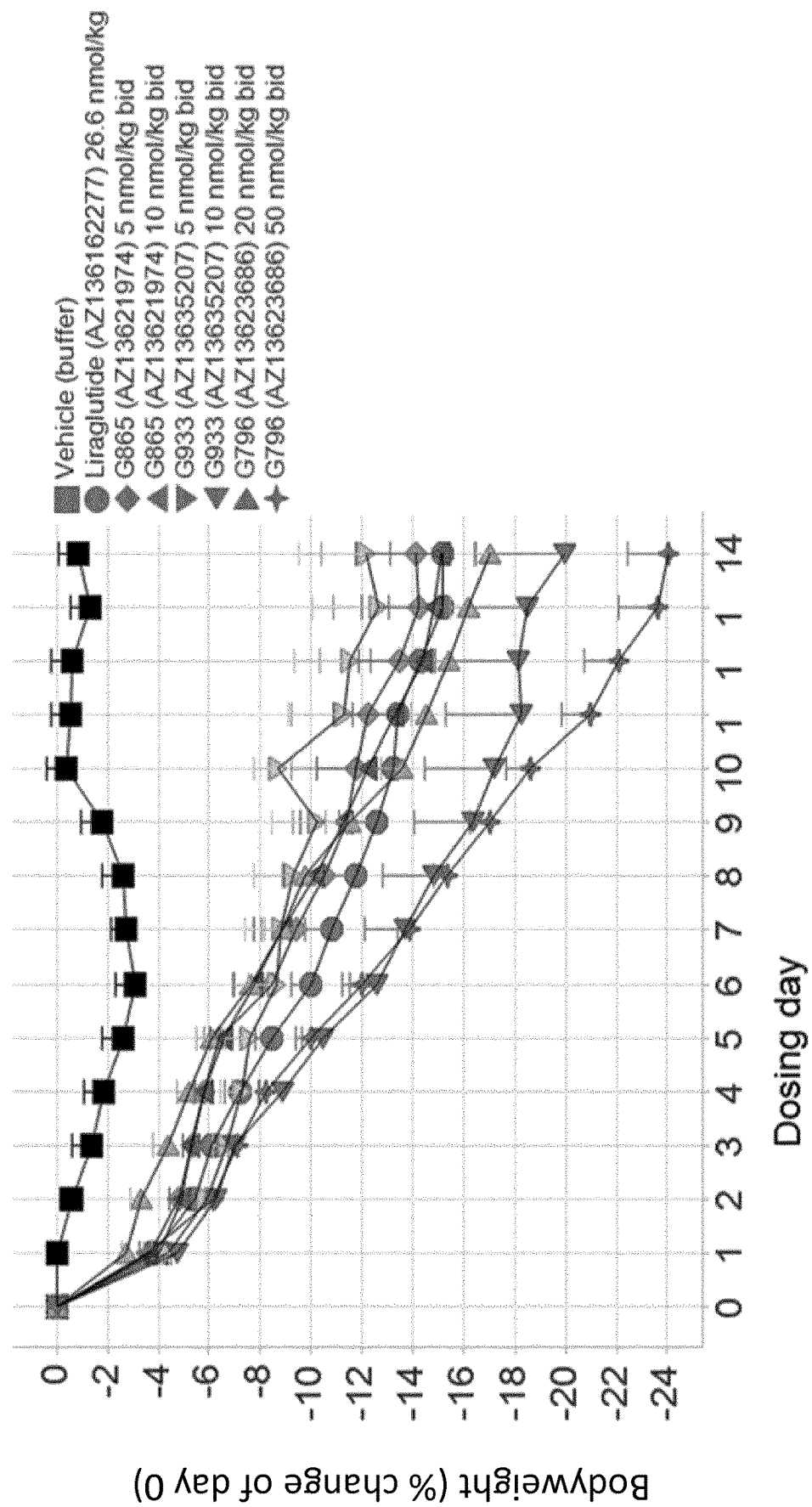
FIG. 8 is a graph comparing the change in body weight results for the three glucagon/GLP-1 co-agonist peptides presented in FIGS. 5, 6, and 7.
Figure 9:
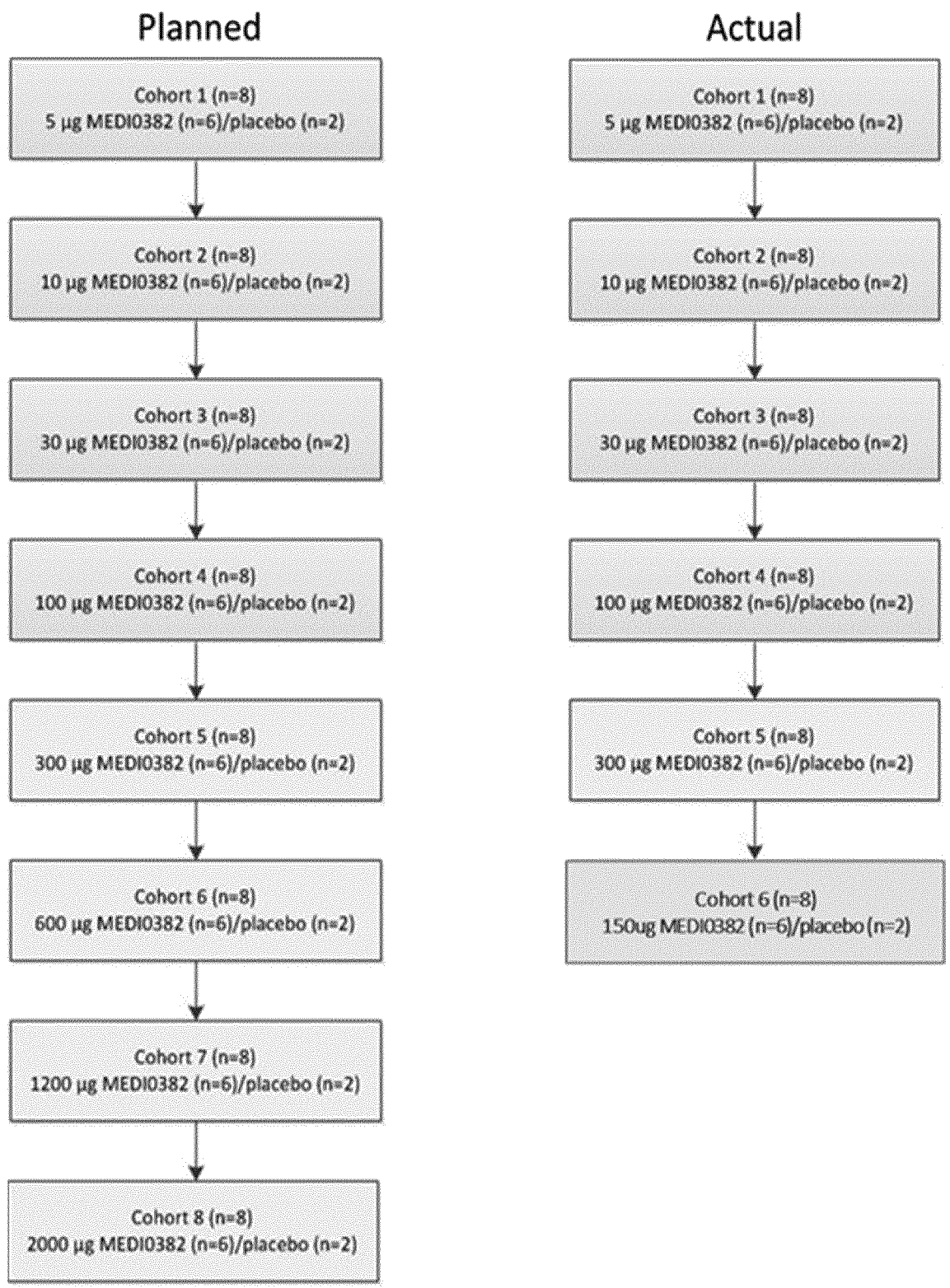

FIG. 9 provides flow diagrams of the planned and actual G933 single ascending dose study.

Figure 10:
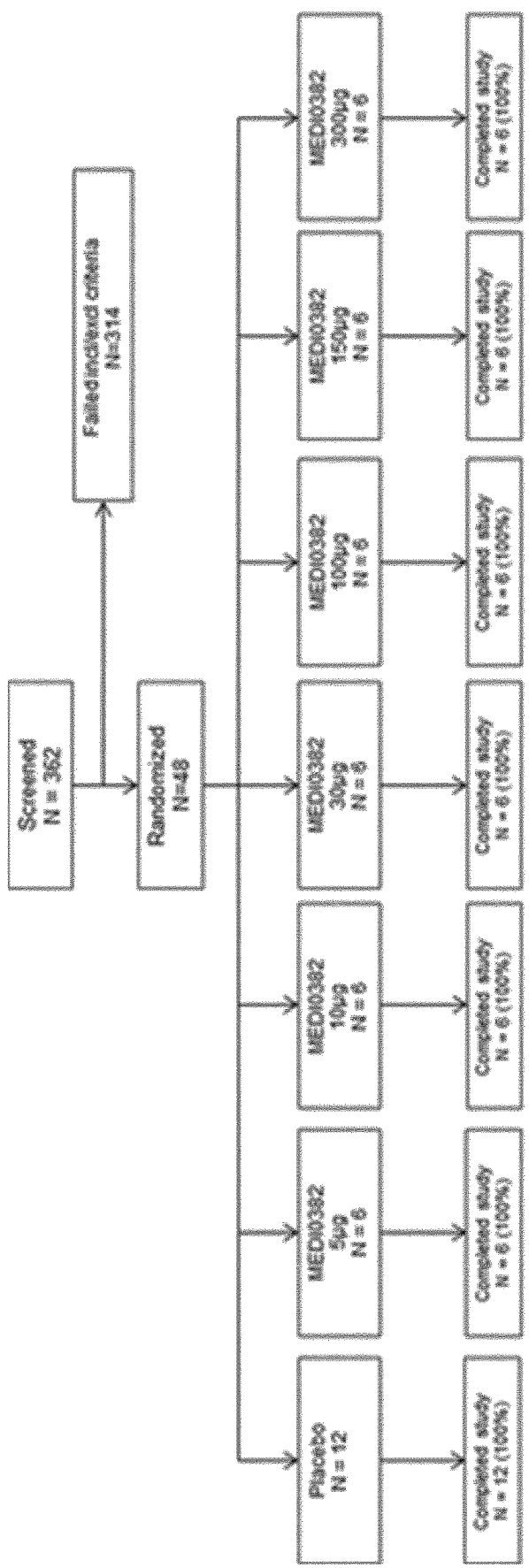

FIG. 10 provides the subject disposition of the G933 single ascending dose study.

Figure 11:
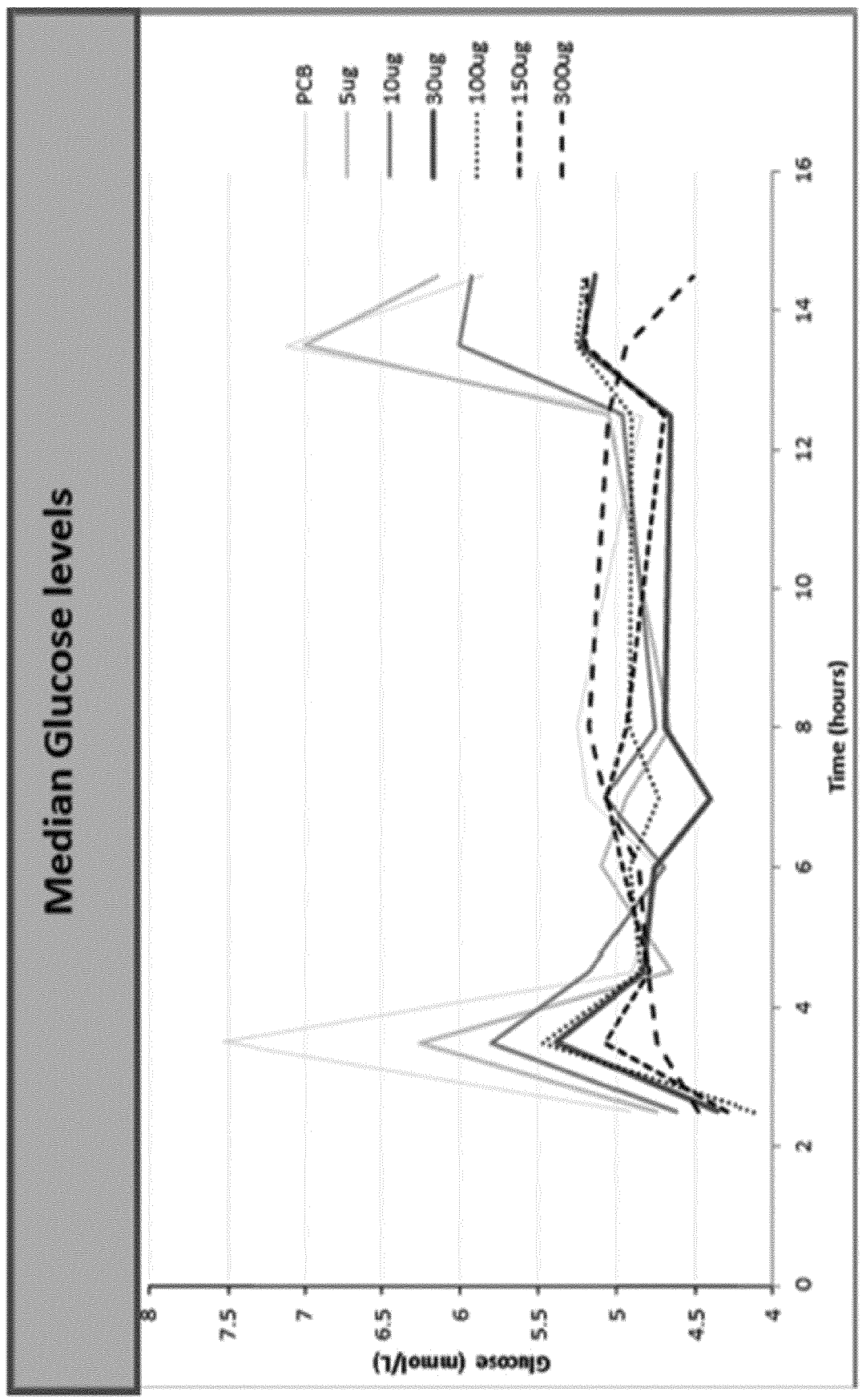

FIG. 11 shows the median glucose levels of subjects in the G933 single ascending dose study.

Figure 12:
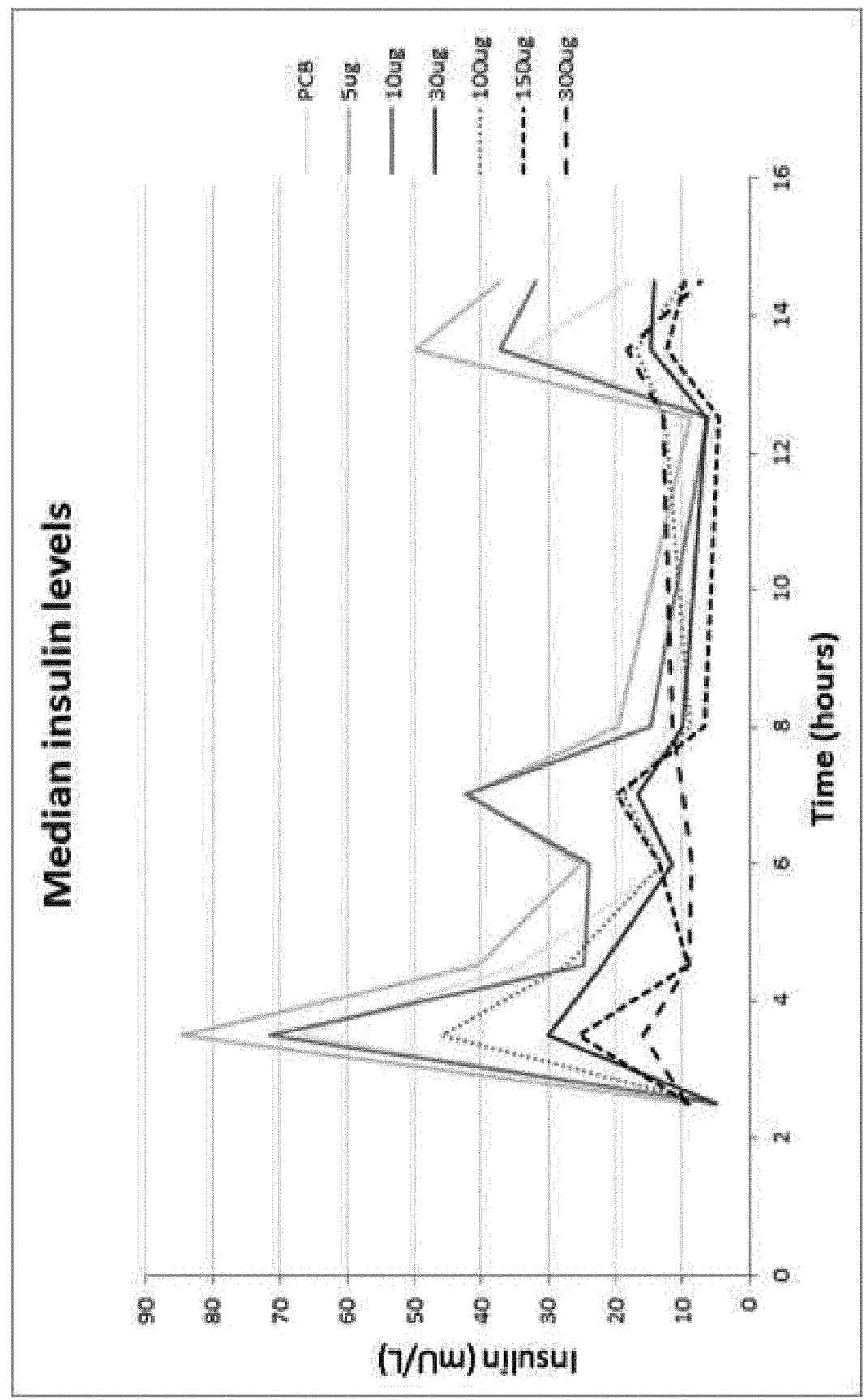

FIG. 12 shows the median insulin levels of subjects in the G933 single ascending dose study.

FIG. 13 provides a flow diagram of Cohorts 1-4 in the G933 multiple ascending dose study. MEDI0382 refers to a 30 amino acid linear peptide with the sequence of SEQ ID NO:19.

Figure 14:
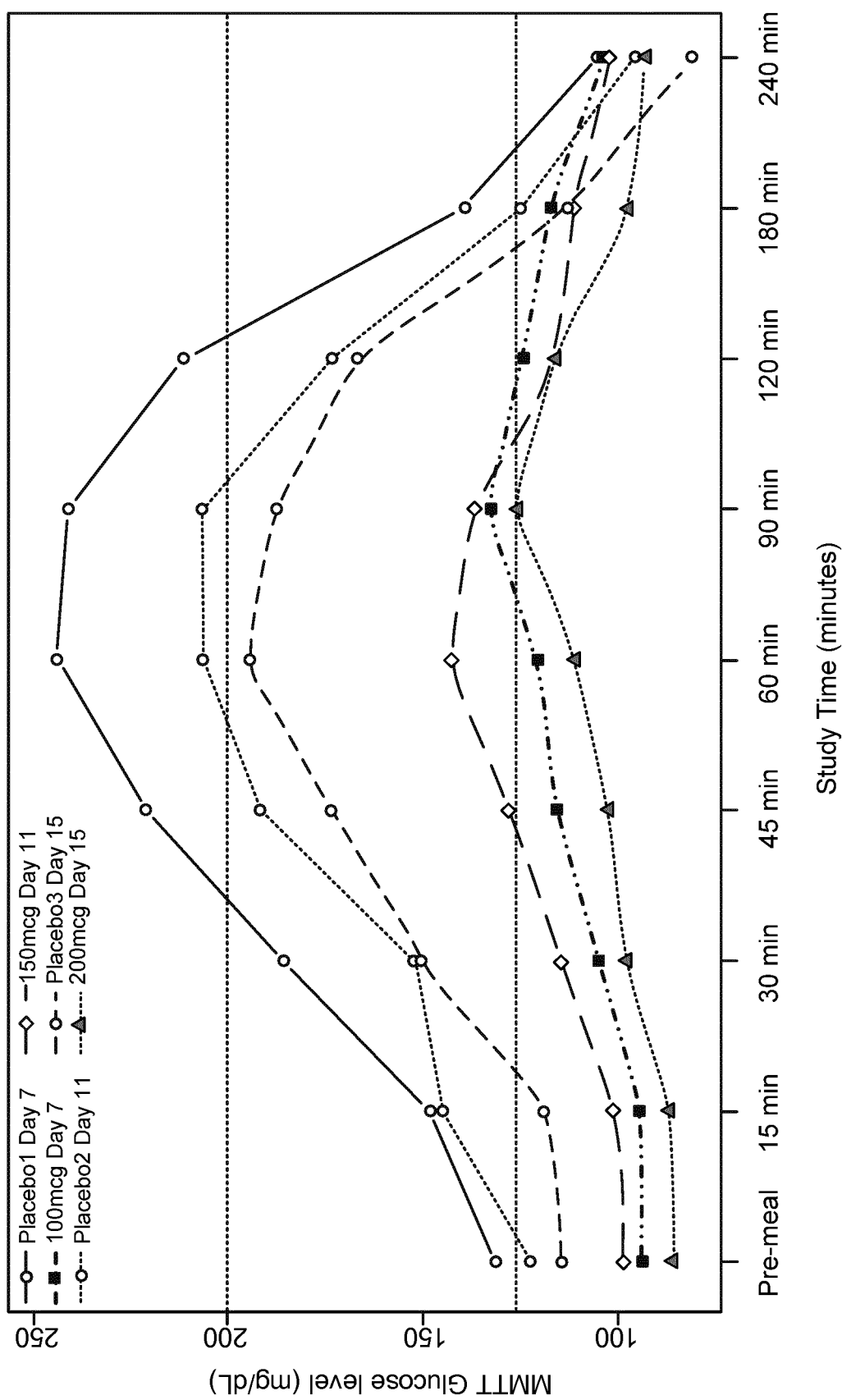

FIG. 14 shows the mean mixed-meal test glucose levels in subjects treated with placebo or 100 μg G933 on Day 7 (Cohort 1), with placebo or 150 μg G933 on Day 11 (Cohort 2), and with placebo or 200 μg G933 on Day 15 (Cohort 3).

FIG. 15 shows the change in baseline fasting glucose levels in subjects treated with placebo or G933 on Day 7 (Cohort 1), with placebo or G933 on Day 9 (Cohort 3), and with placebo or G933 on Day 15 (Cohort 3).

FIG. 16 shows the change in weight from baseline weight over the course of the study in both Cohorts 1 and 3 and on Days 7 and 15 in Cohorts 1 and 3, respectively.

Figure 17:
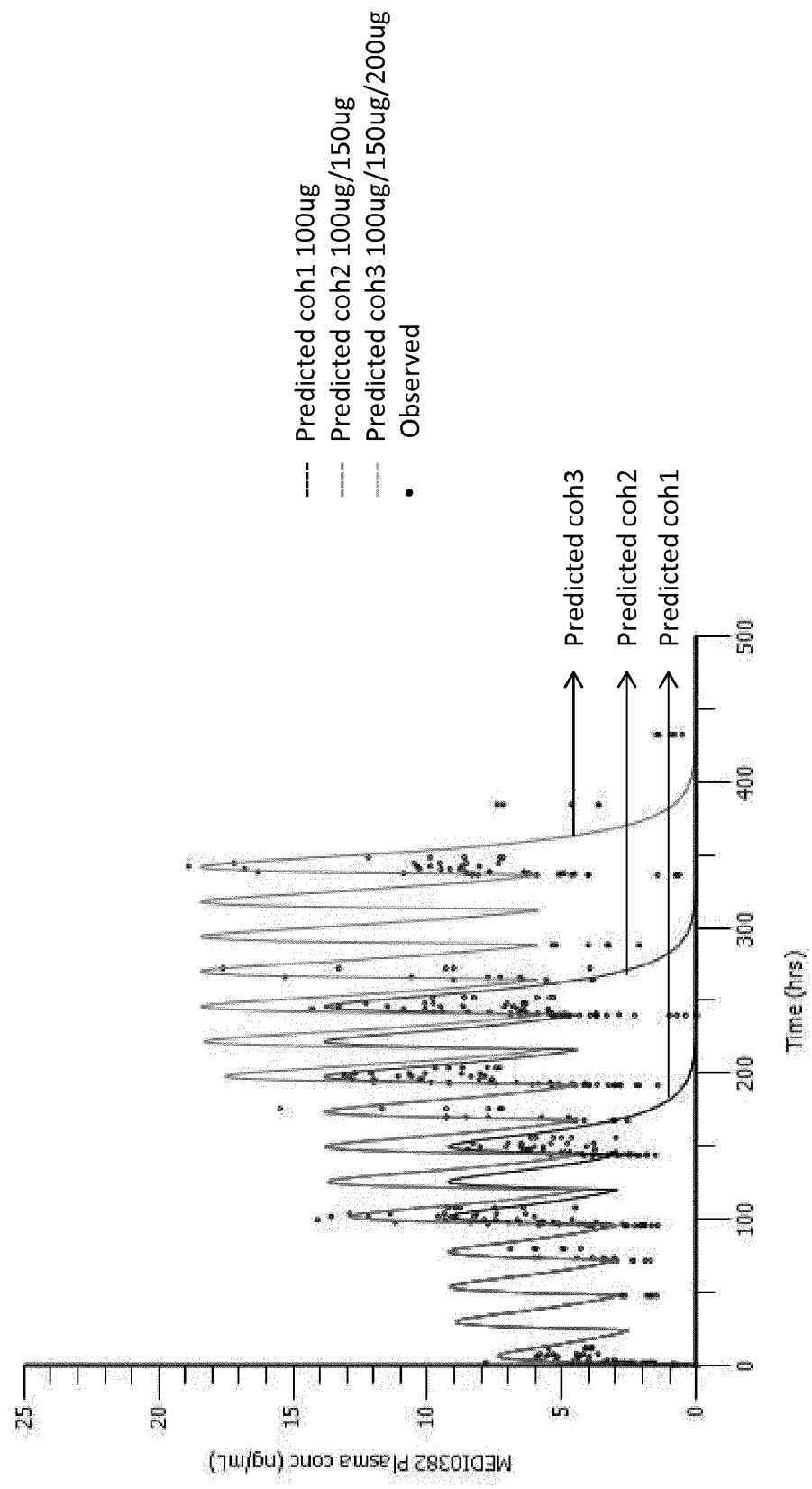

FIG. 17 shows the plasma concentration of MEDI0382 after repeat dosing.

Figure 18:
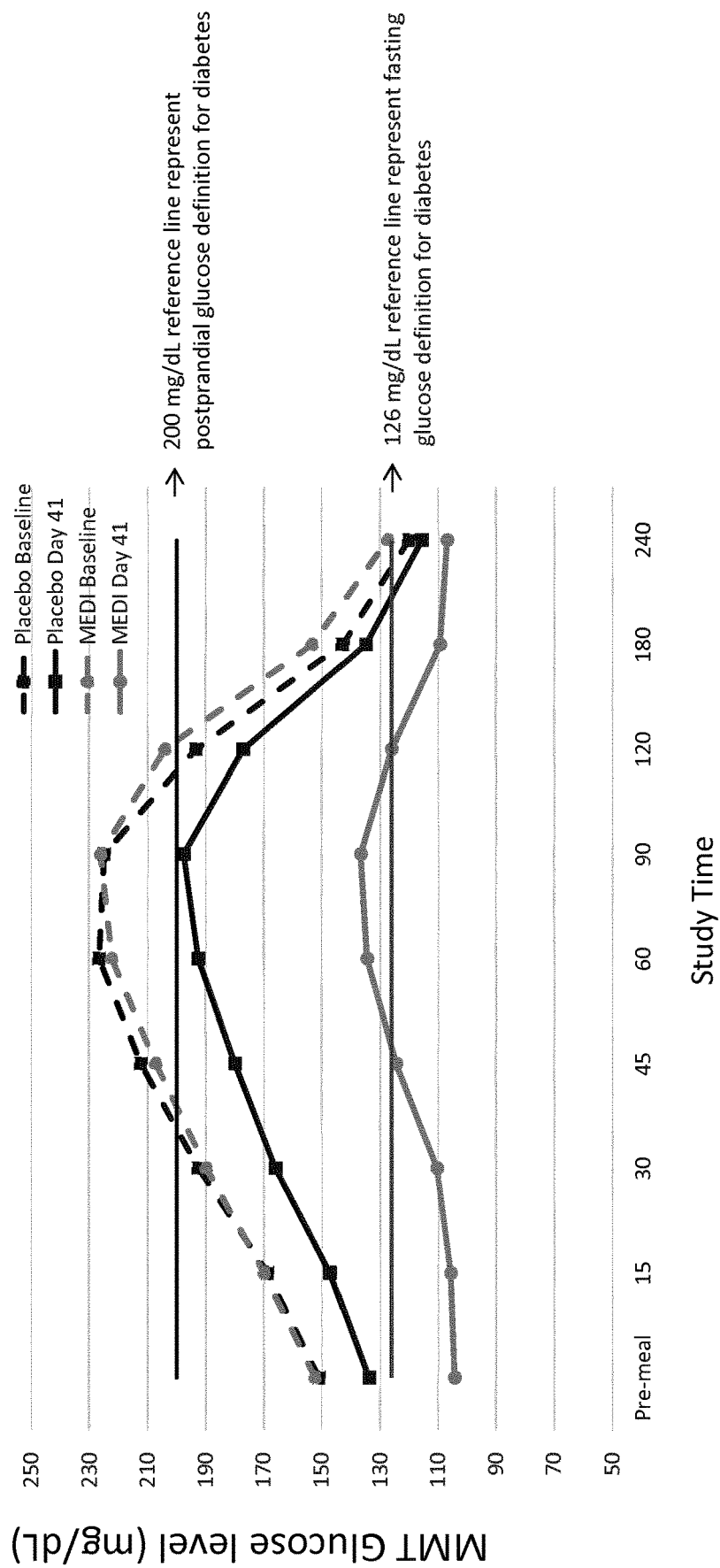

FIG. 18 shows an improvement in glucose control as measured by glucose levels in patients treated with G933. The dashed lines represent glucose levels observed at baseline (Day 1), and the solid lines represent glucose levels observed on day 41.

Figure 19:
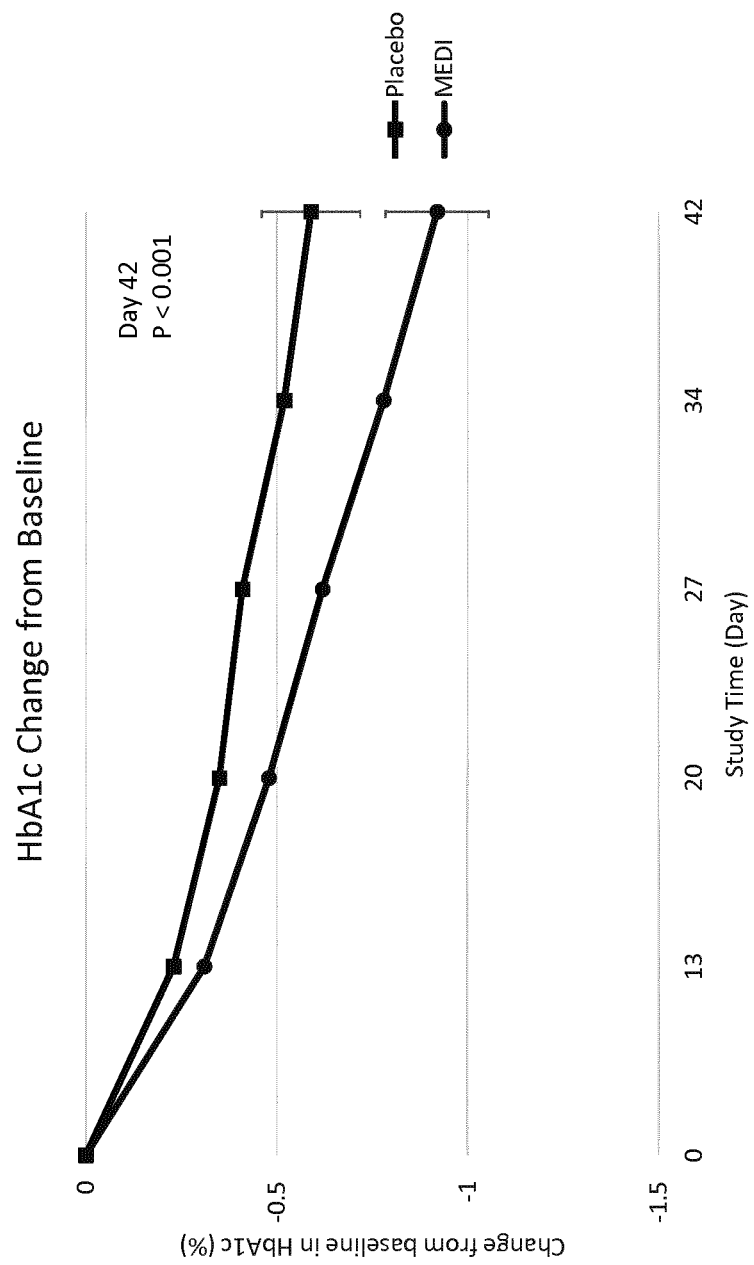

FIG. 19 shows an improvement in glucose control as measured by HbA1c in patients treated with G933.

Figure 20:
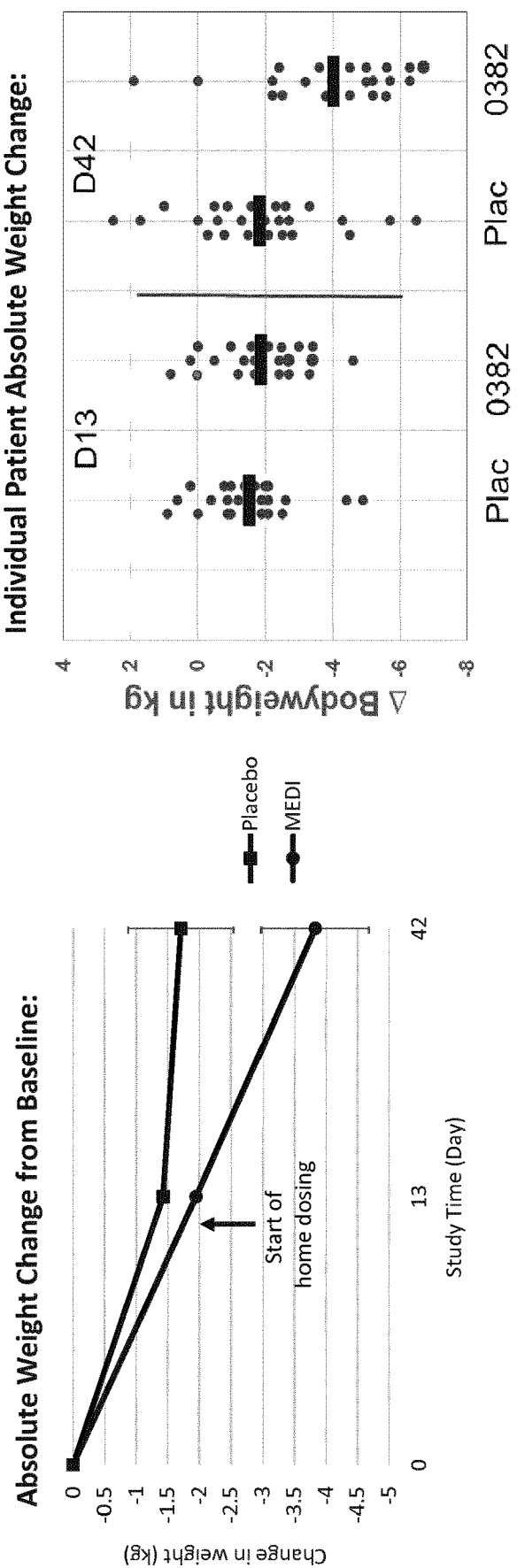

FIG. 20 shows a decrease in absolute weight in patients treated with G933. (G933 is referred to as "MEDI" or "0382" in this figure; "Plac" refers to placebo.)

Figure 21:
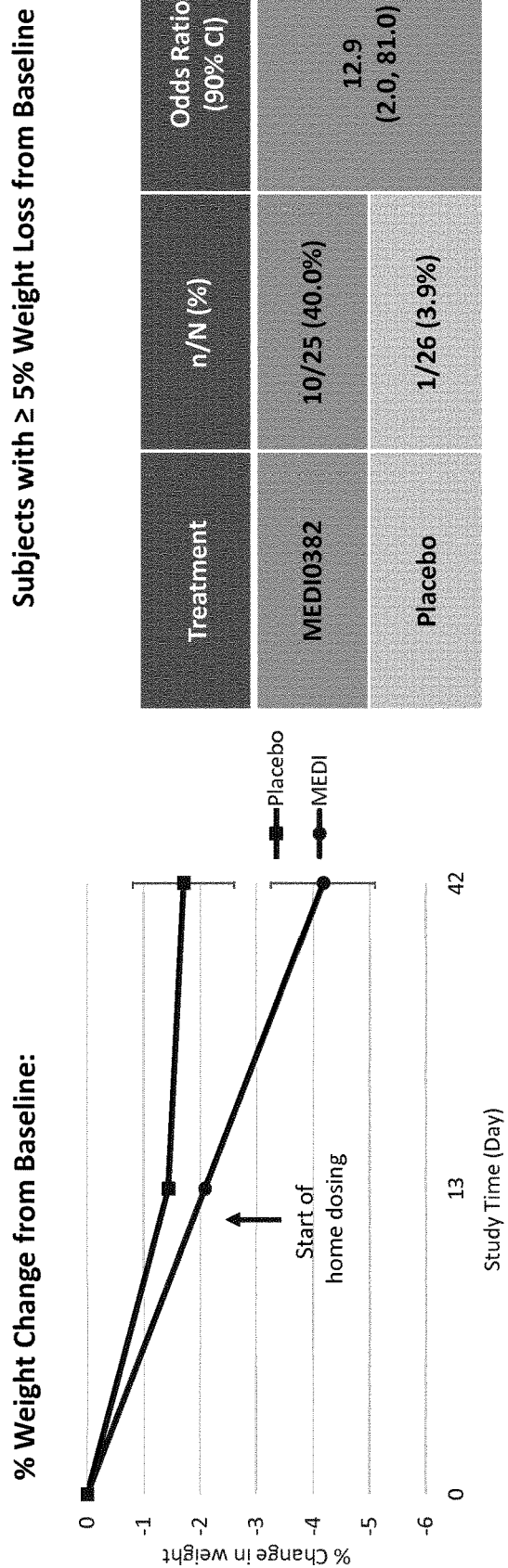

FIG. 21 shows a decrease in percent weight in patients treated with G933. ("MEDI" refers to "MEDI0382" in this figure.)

FIG. 22 shows an assessment of liver fat reduction in patients treated with G933. Representative images from individual subjects are provided.

Figure 23:
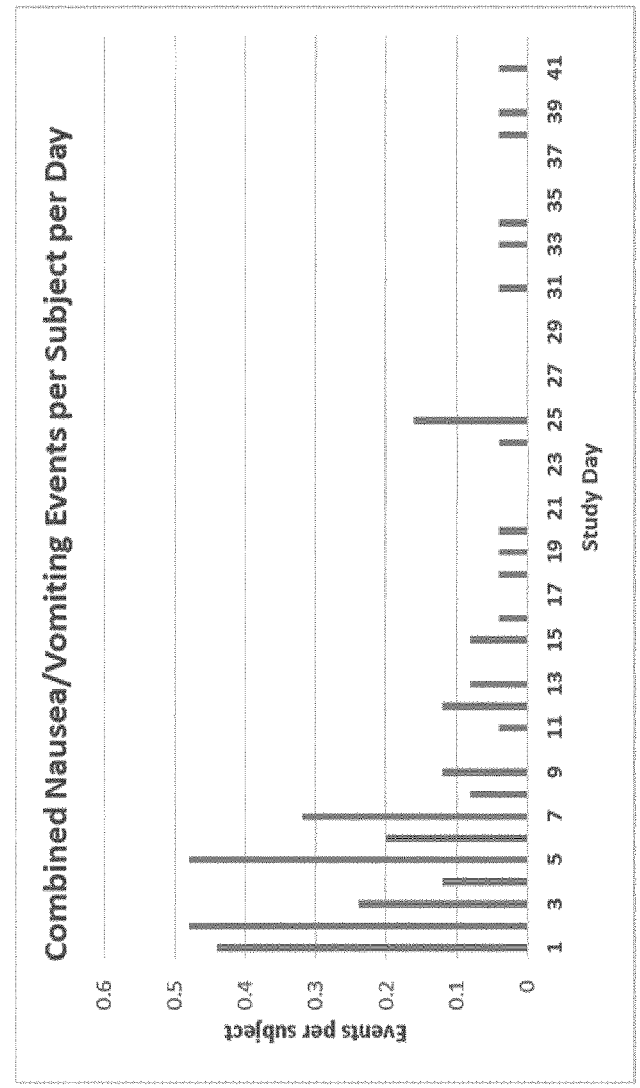

FIG. 23 shows the nausea and vomiting that occurred in patients treated with G933.

FIG. 24 provides a flow diagram of Cohorts 5 and 6 in the G933 multiple ascending dose study.

Figure 25:
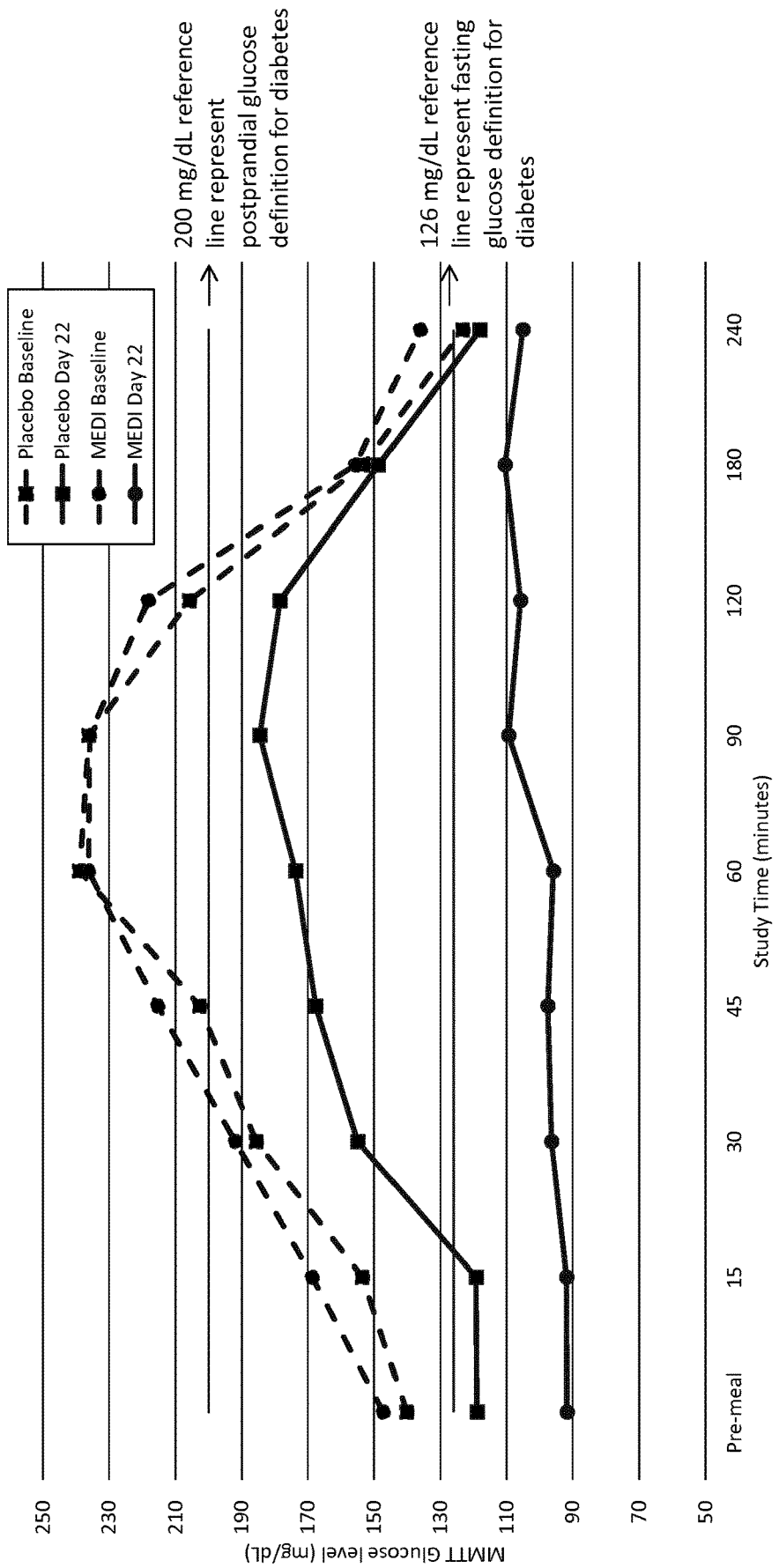

FIG. 25 shows an improvement in glucose control as measured by glucose levels in Cohort 5 patients treated with G933 as compared to placebo. The dashed lines represent glucose levels observed at baseline (Day 1), and the solid lines represent glucose levels observed on day 17. (G933 is referred to as "MEDI" in this figure.)

Figure 26:
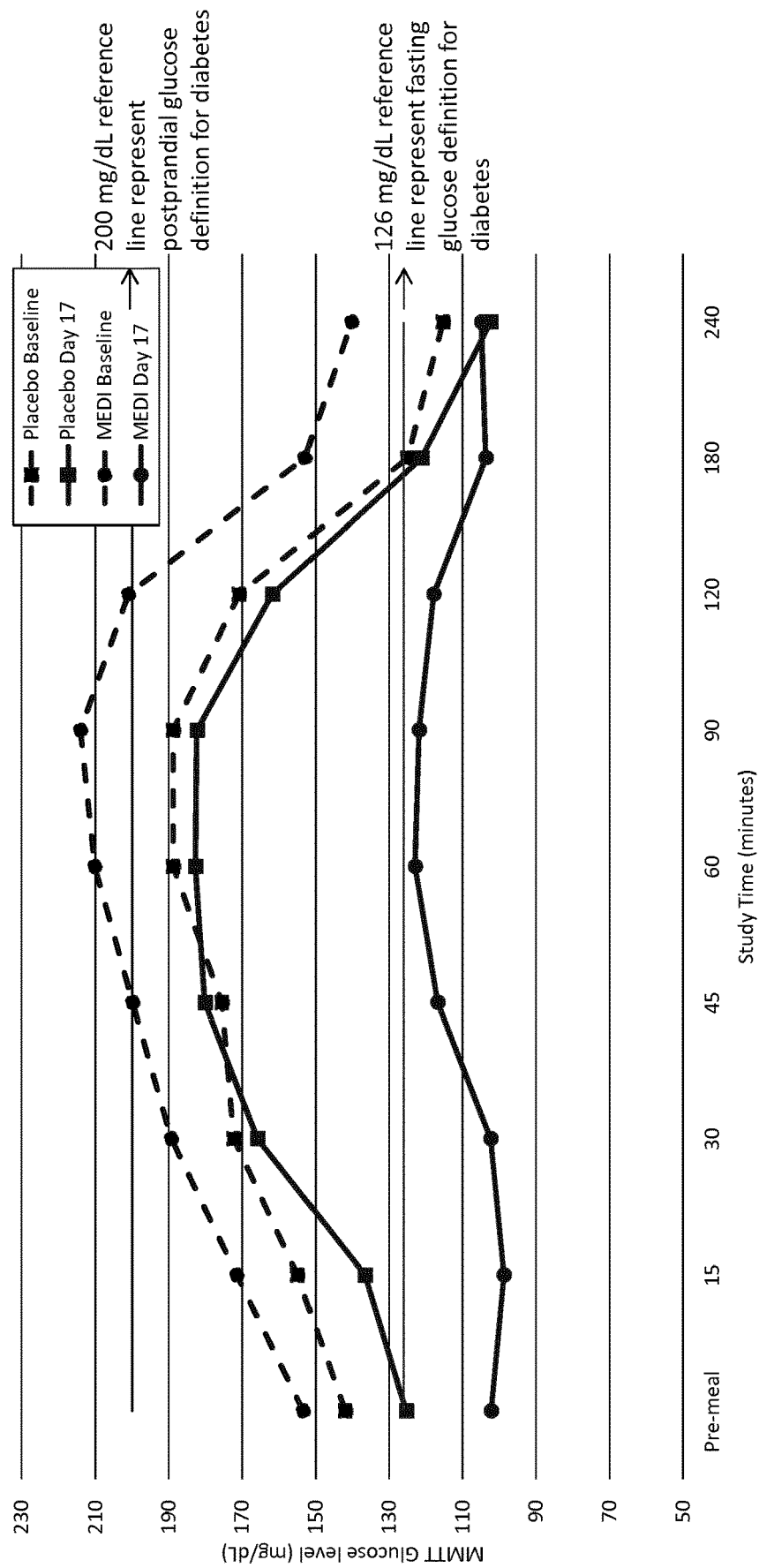

FIG. 26 shows an improvement in glucose control as measured by glucose levels in Cohort 6 patients treated with G933 as compared to placebo. The dashed lines represent glucose levels observed at baseline (Day 1), and the solid lines represent glucose levels observed on day 17. (G933 is referred to as "MEDI" in this figure.)

Figure 27:
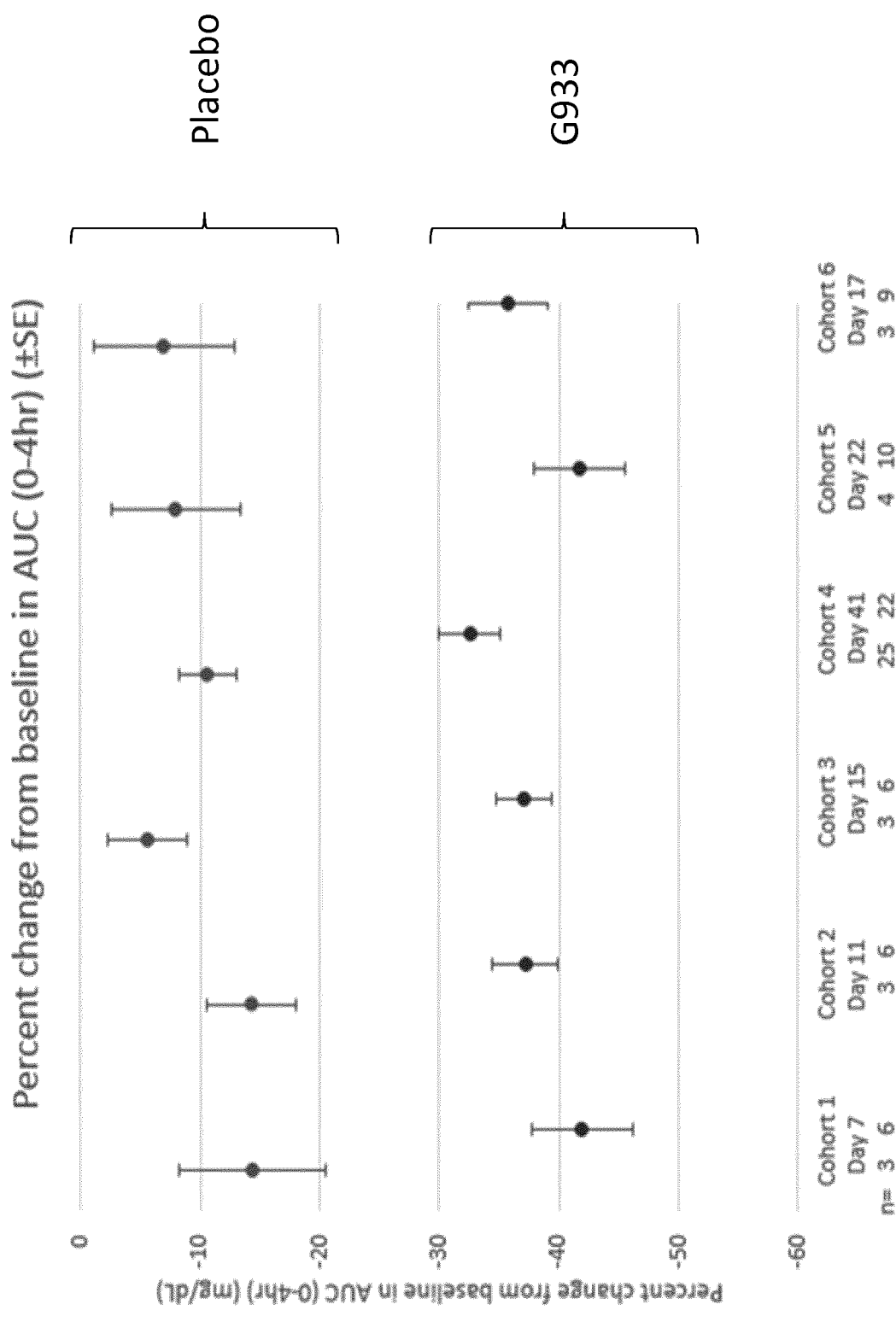

FIG. 27 shows the percent change from baseline glucose AUC in all cohorts.

FIG. 28 shows an improvement in fasting glucose levels in Cohorts 5 and 6.

(G933 is referred to as "MEDI" in this figure.)

FIG. 29 shows the weight change from baseline in Cohorts 5 and 6. (G933 is referred to as "MEDI" in this figure.)

FIG. 30 shows weight loss and change in glucose across all cohorts.

Figure 31:
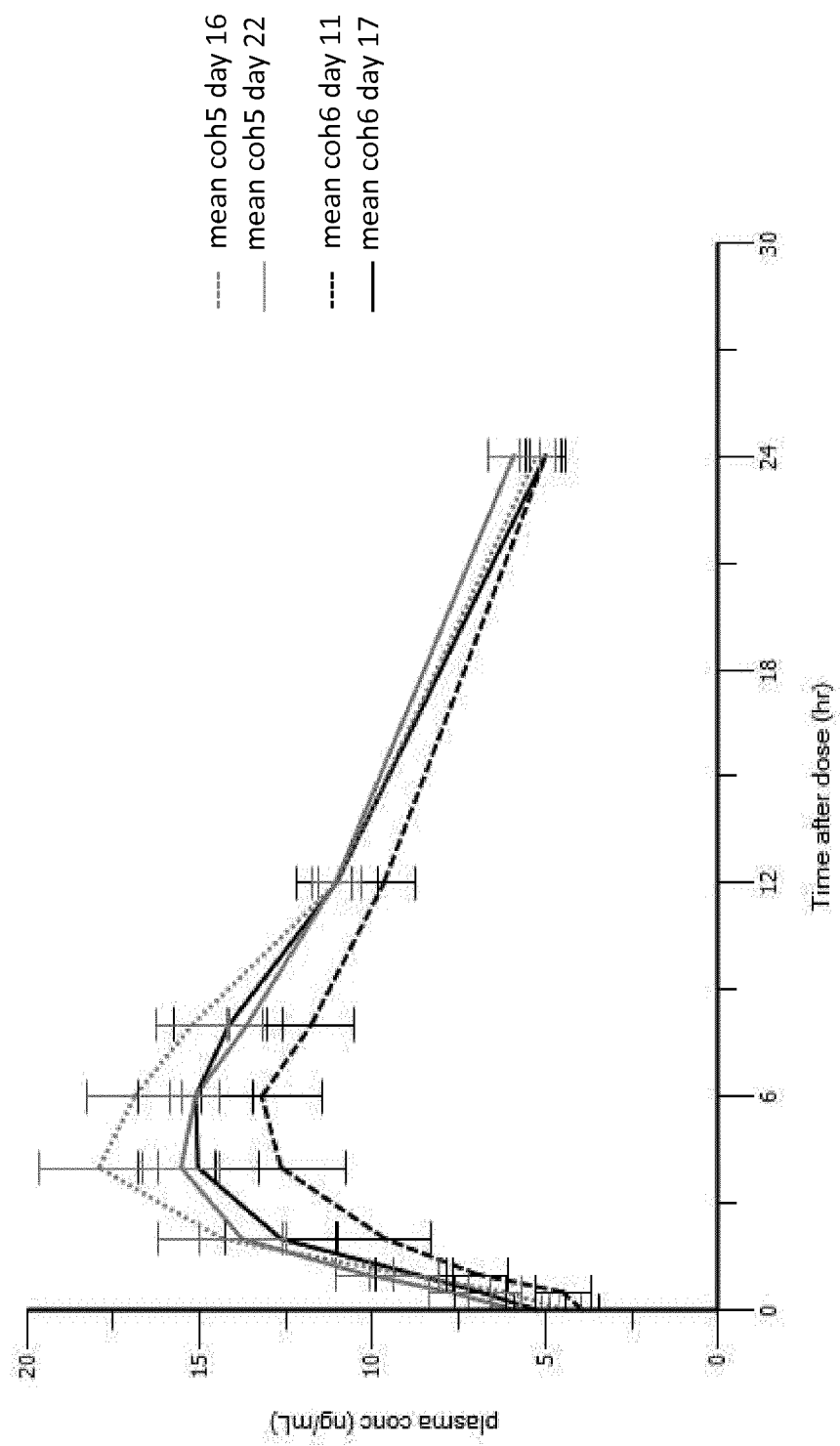

FIG. 31 shows the G933 plasma concentration in Cohort 5 on days 16 and 22 and in Cohort 6 on days 11 and 17.

DETAILED DESCRIPTION

Definitions

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided. A peptide "comprising" a particular amino acid sequence refers to a peptide containing the amino acid sequence, wherein the peptide may or may not contain additional amino acids or other modifications to the amino acid sequence. A peptide "consisting of" a particular amino acid sequence refers to a peptide containing only the amino acid sequence and no additional amino acids or other modifications to the amino acid sequence. A peptide "comprising" an amino acid sequence "consisting of" a particular amino acid sequence refers to a peptide containing the amino acid sequence and no additional amino acids; however, the peptide may comprise other modifications to the amino acid sequence (e.g., an acyl moiety or a palmitoyl moiety).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and comprises any chain or chains of two or more amino acids. Thus, as used herein, a "peptide," a "peptide subunit," a "protein," an "amino acid chain," an "amino acid sequence," or any other term used to refer to a chain or chains of two or more amino acids, are included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, glycosylation, acetylation, phosphorylation, amidation, derivatization by known protecting/blocking groups, proteolytic cleavage, or modification by non-naturally occurring amino acids.

More specifically, the term "peptide" as used herein encompasses full length peptides and fragments, variants or derivatives thereof, e.g., a GLP-1/glucagon agonist peptide (e.g., 29, 30, or 31 amino acids in length). A "peptide" as disclosed herein, e.g., a GLP-1/glucagon agonist peptide, can be part of a fusion polypeptide comprising additional components such as, e.g., an Fc domain or an albumin domain, to increase half-life. A peptide as described herein can also be derivatized in a number of different ways.

The term "isolated" refers to the state in which peptides or nucleic acids, will generally be in accordance with the present disclosure. Isolated peptides and isolated nucleic acids will be free or substantially free of material with which they are naturally associated such as other peptides or nucleic acids with which they are found in their natural environment, or the environment in which they are prepared (e.g. cell culture) when such preparation is by recombinant DNA technology practiced in vitro or in vivo. Peptides and nucleic acid can be formulated with diluents or adjuvants and still for practical purposes be isolated—for example the peptides will normally be mixed with gelatin or other carriers if used to coat microtitre plates for use in immunoassays, or will be mixed with pharmaceutically acceptable carriers or diluents when used in diagnosis or therapy.

A "recombinant" peptide refers to a peptide produced via recombinant DNA technology. Recombinantly produced peptides expressed in host cells are considered isolated for the purpose of the present disclosure, as are native or recombinant polypeptides which have been separated, fractionated, or partially or substantially purified by any suitable technique.

The terms "fragment," "analog," "derivative," or "variant" when referring to a GLP-1/glucagon agonist peptide include any peptide which retains at least some desirable activity, e.g., binding to glucagon and/or GLP-1 receptors. Fragments of GLP-1/glucagon agonist peptides provided herein include proteolytic fragments, deletion fragments which exhibit desirable properties during expression, purification, and or administration to a subject.

The term "variant," as used herein, refers to a peptide that differs from the recited peptide due to amino acid substitutions, deletions, insertions, and/or modifications. Variants can be produced using art-known mutagenesis techniques. Variants can also, or alternatively, contain other modifications—for example a peptide can be conjugated or coupled, e.g., fused to a heterologous amino acid sequence or other moiety, e.g., for increasing half-life, solubility, or stability. Examples of moieties to be conjugated or coupled to a peptide provided herein include, but are not limited to, albumin, an immunoglobulin Fc region, polyethylene glycol (PEG), and the like. The peptide can also be conjugated or produced coupled to a linker or other sequence for ease of synthesis, purification or identification of the peptide (e.g., 6-His), or to enhance binding of the polypeptide to a solid support.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10), and any other required parameter including but not limited to matrix option.

The terms "composition" or "pharmaceutical composition" refer to compositions containing a GLP-1/glucagon agonist peptide provided herein, along with e.g., pharmaceutically acceptable carriers, excipients, or diluents for administration to a subject in need of treatment, e.g., a human subject being treated for obesity.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

An "effective amount" is that amount of a GLP-1/glucagon agonist peptide provided herein, the administration of which to a subject, either in a single dose or as part of a series, is effective for treatment, e.g., treatment of obesity. An amount is effective, for example, when its administration results in one or more of weight loss or weight maintenance (e.g., prevention of weight gain), loss of body fat, prevention or modulation hypoglycemia, prevention or modulation hyperglycemia, promotion of insulin synthesis, or reduction in food intake. This amount can be a fixed dose for all subjects being treated, or can vary depending upon the weight, health, and physical condition of the subject to be treated, the extent of weight loss or weight maintenance desired, the formulation of peptide, a professional assessment of the medical situation, and other relevant factors.

The term "subject" is meant any subject, particularly a mammalian subject, in need of treatment with a GLP-1/glucagon agonist peptide provided herein. Mammalian subjects include, but are not limited to, humans, dogs, cats, guinea pigs, rabbits, rats, mice, horses, cattle, bears, cows, apes, monkeys, orangutans, and chimpanzees, and so on. In one embodiment, the subject is a human subject.

As used herein, a "subject in need thereof" refers to an individual for whom it is desirable to treat, e.g., to an obese subject or a subject prone to obesity for whom it is desirable to facilitate weight or body fat loss, weight or body fat maintenance, or to prevent or minimize weight gain over a specified period of time.

Terms such as "treating" or "treatment" or "to treat" refer to therapeutic measures that cure and/or halt progression of a diagnosed pathologic condition or disorder. Terms such as "preventing" refer to prophylactic or preventative measures that prevent and/or slow the development of a targeted pathologic condition or disorder. Thus, those in need of treatment include those already with the disease or condition. Those in need of prevention include those prone to have the disease or condition and those in whom the disease or condition is to be prevented. For example, the phrase "treating a patient" having a disease or condition caused or characterized by excess body weight refers to reducing the severity of the disease or condition to an extent that the subject no longer suffers discomfort and/or altered function due to it. The phrase "preventing" a disease or condition caused or characterized by excess body weight refers to reducing the potential for the disease or condition and/or reducing the occurrence of the disease or condition (for example a relative reduction in occurrence as compared to untreated patients).

Terms such as "decreasing the severity" refer to therapeutic measures that slow down or lessen the symptoms of a diagnosed pathologic condition or disorder. For example, the phrase "decreasing the severity" of a disease or condition caused or characterized by excess body weight refers to reducing the severity of the disease or condition (for example, a reduction in weight when compared to untreated patients or an increase in glucose control).

As used herein a "GLP-1/glucagon agonist peptide" is a chimeric peptide that exhibits activity at the glucagon receptor of at least about 1%, 5%, 10%, 20%, 30%, 40%, 50%, 60%, 70%, 80%, 90%, 95%, or more relative to native glucagon and also exhibits activity at the GLP-1 receptor of about at least about 1%, 5%, 10%, 20%, 30%, 40%, 50%, 60%, 70%, 80%, 90%, 95%, or more relative to native GLP-1, under the conditions of assay 1.

As used herein the term "native glucagon" refers to naturally-occurring glucagon, e.g., human glucagon, comprising the sequence of SEQ ID NO: 1. The term "native GLP-1" refers to naturally-occurring GLP-1, e.g., human GLP-1, and is a generic term that encompasses, e.g., GLP-1(7-36) amide (SEQ ID NO: 2), GLP-1(7-37) acid (SEQ ID NO: 3), or a mixture of those two compounds. As used herein, a general reference to "glucagon" or "GLP-1" in the absence of any further designation is intended to mean native human glucagon or native human GLP-1, respectively. Unless otherwise indicated, "glucagon" refers to human glucagon, and "GLP-1" refers to human GLP-1.

GLP-1/Glucagon Agonist Peptides

Provided herein are peptides which bind both to a glucagon receptor and to a GLP-1 receptor. Exemplary peptides are provided in WO 2014/091316, which is herein incorporated by reference in its entirety. In certain embodiments, the peptide is MEDI0382, i.e., a 30 amino acid linear peptide with the sequence of SEQ ID NO:19 that contains a gamma glutamate linker and palmitoyl group derivatization at residue 10. In certain embodiments, the peptides provided herein are co-agonists of glucagon and GLP-1 activity. Such peptides are referred to herein as GLP-1/glucagon agonist peptides. GLP-1/glucagon agonist peptides as provided herein possess GLP-1 and glucagon activities with favorable ratios to promote weight loss, prevent weight gain, or to maintain a desirable body weight, and possess optimized solubility, formulatability, and stability. In certain embodiments, GLP-1/glucagon agonist peptides as provided herein are active at the human GLP1 and human glucagon receptors, in certain embodiment relative activity compared to the natural ligand at the GLP-1 receptor is at least about 1-fold, 2-fold 5-fold, 8-fold, 10-fold, 15-fold, 20-fold, or 25-fold higher than at the glucagon receptor.

In certain embodiments, GLP-1/glucagon agonist peptides as disclosed have desirable potencies at the glucagon and GLP-1 receptors, and have desirable relative potencies for promoting weight loss. In certain embodiments, GLP-1/glucagon agonist peptides as disclosed exhibit in vitro potencies at the GLP-1 receptor as shown by an EC50 in the cAMP assay 1 (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the GLP-1 receptor as shown by EC50 in the cAMP assay in 4.4% human serum albumin (assay 2, see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the glucagon receptor as shown by an EC50 in the cAMP assay 1 (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the glucagon receptor as shown by an EC50 in the cAMP assay in 4.4% human serum albumin (assay 2, see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed have relative GLP1-R/glucR potency ratios, when compared to the native ligands, in the range of about 0.01 to 0.50, e.g., from about 0.02 to 0.30, e.g., about 0.02, 0.03, 0.04, 0.05, 0.06, 0.07, 0.08, 0.09, 0.10, 0.11. 0.12, 0.13, 0.14, 0.15, 0.16, 0.17, 0.18, 0.19, 0.20, 0.21, 0.22, 0.23, 0.24, 0.25, 0.26, 0.27, 0.28, or 0.30 when using assay 2.

In certain embodiments, GLP-1/glucagon agonist peptides as disclosed exhibit in vitro potencies at the glucose-dependent insulinotropic peptide (gastric inhibitory peptide) (GIPR) as shown by an EC50 in the cAMP assay 1 (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the GIPR as shown by EC50 in the cAMP assay in 4.4% human serum albumin (assay 2, see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain embodiments, GLP-1/glucagon agonist peptides provided herein possess one or more criteria of acceptable solubility, ease in formulatability, plasma stability, and improved pharmacokinetic properties. In certain embodiments, GLP-1/glucagon agonist peptides as disclosed are soluble in standard buffers over a broad pH range.

In certain embodiments, GLP-1/glucagon agonist peptides are soluble in common buffer solutions at a concentration up to 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, or more, in buffer systems and a range of ionic strengths, e.g., from 0.25 to 150 mM, including, but not limited to phosphate buffer, Tris buffer, glutamate buffer, acetate buffer, succinate buffer, or histidine buffer. Exemplary buffers include 100 mM glutamate pH 4.5 buffer, 100 mM acetate pH 5 buffer, 100 mM succinate pH 5 buffer, 100 mM phosphate pH 6 buffer, 100 mM histidine pH 6 buffer, 100 mM phosphate pH 6.5 buffer, 100 mM phosphate pH 7.0 buffer, 100 mM histidine pH 7.0 buffer, 100 mM phosphate pH 7.5 buffer, 100 mM Tris pH 7.5 buffer, and 100 mM Tris pH 8.0 buffer. In certain embodiments, GLP-1/glucagon agonist peptides as disclosed are soluble in standard buffers at 0.8 mg/ml over a range of pH, e.g., from pH 4.0 to pH 8.0, e.g., at pH 4.0, 4.5, 5.0, 5.5, 6.0, 6.5, 7.0, 7.5, 8.0, or 8.5. In certain embodiments, GLP-1/glucagon agonist peptides as disclosed are soluble in standard buffers from pH 4.5 to 8.0, 5.0 to 8.0, 5.5 to 8.0, 6.0 to 8.0, 6.5 to 8.0, 7.0 to 8.0, 4.5 to 8.5, 5.5 to 8.5, 5.5 to 8.5, 6.0 to 8.5, 6.5 to 8.5, or 7.0 to 8.5.

In certain embodiments, GLP-1/glucagon agonist peptides as disclosed are formulatable in standard pharmaceutical formulations. Exemplary formulations include, but are not limited to: 0.1M Tris pH 7.5, 150 mM Mannitol, final formulation pH=7.2; 0.05M Tris, 50 mM Arginine/Proline, final formulation pH=8.0; or sodium phosphate buffer (pH8)/1.85% W/V propylene glycol, final formulation pH=7.0. In certain embodiments GLP-1/glucagon agonist peptides as disclosed are soluble is these or other formulations at a concentration up to 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, or more.

In certain embodiments, GLP-1/glucagon agonist peptides as disclosed are acceptably stable against proteases in serum or plasma. Common degradation products of glucagon or GLP-1 include +1 products (acid) and the DPP IV-cleavage products. Products with +1 mass may arise from deamidation at amide groups of glutamine or at the C-terminus. Cleavage products arise from the action of the protease DPP IV in plasma. In certain embodiments, GLP-1/glucagon agonist peptides as disclosed remain stable in plasma at levels up to 30%, 40%, 50%, 60%, 70%, 80%, 90%, or 100% after 24 hours in plasma at 37° C.

Provided herein is a GLP-1/glucagon agonist peptide comprising the amino acid sequence:

HX2QGTFTSDX10SX12X13LX15X16X17X18AX20X21FX23 X24WLX27X28GX30;

wherein X2 is G or S, X10 is Y or K, X12 is K, E, R, or S, X13 is K or Y, X15 is D or E, X16 is S or G, X17 is E, R, Q, or K, X18 is R, S, or A, X20 is R, K, or Q, X21 is D or E, X23 is V or I, X24 is A or Q, X27 is E or V, X28 is A or K, and X30 is G or R (SEQ ID NO:4). In certain embodiments, the isolated peptide shown above (SEQ ID NO:4) is provided, wherein X2 is G, X10 is K, X12 is E, R, or S, X13 is K, X17 is E or K, X18 is S, X20 is R, X27 is E, and/or X28 is A. In certain embodiments, the isolated peptide shown above (SEQ ID NO:4) is provided, wherein X10 is K, X12 is E, X17 is E, X20 is R, X27 is E, and/or X28 is A.

In certain embodiments the isolated peptide shown above is provided, where X2 is S, X10 is Y or K, X12 is K, E, R, or S, X13 is K or Y, X15 is D, X16 is S, X17 is E, R, Q, or K, X18 is R, S, or A, X20 is R, X21 is D, X23 is V, X24 is A, X27 is E or V, X28 is A, and X30 is G (SEQ ID NO:5). In certain embodiments the isolated peptide shown above is provided, where X2 is S, X10 is Y or K, X12 is K, E, R, or S, X13 is K or Y, X15 is D, X16 is S, if X17 is E and X18 is R, or if X17 is R and X18 is S, then X20 is R, X21 is D, X23 is V, X24 is A, X27 is E or V, X28 is A, and X30 is G (SEQ ID NO: 6 and SEQ ID NO. 7, respectively). In certain embodiments the isolated peptide shown above is provided, where X2 is S, X10 is Y, X12 is K, X13 is K, X15 is D, X16 is S, if X17 is E and X18 is R, or if X17 is R and X18 is S, X20 is R, X21 is D, X23 is V, X24 is A, X27 is V, X28 is A, and X30 is G (SEQ ID NO: 8 and SEQ ID NO: 9, respectively). In certain embodiments the isolated peptide shown above is provided, where X2 is S, X10 is K, X12 is K, E, R, or S, X13 is Y, X15 is D, X16 is S, if X17 is E and X18 is R, and if X17 is R and X18 is S, X20 is R, X21 is D, X23 is V, X24 is A, X27 is E, X28 is A, and X30 is G (SEQ ID NO: 10 and SEQ ID NO: 11, respectively). In certain embodiments the isolated peptide shown above is provided, where X2 is S, X10 is K, X12 is E, X13 is Y, X15 is D, X16 is S, if X17 is E and X18 is R, or if X17 is R and X18 is S, X20 is R, X21 is D, X23 is V, X24 is A, X27 is E, X28 is A, and X30 is G (SEQ ID NO: 12 and SEQ ID NO: 13, respectively). In certain embodiments the isolated peptide shown above is provided, where X2 is S, X10 is K, X12 is R, X13 is Y, X15 is D, X16 is 5, if X17 is E and X18 is R, or if X17 is R and X18 is S, X20 is R, X21 is D, X23 is V, X24 is A, X27 is E, X28 is A, and X30 is G (SEQ ID NO: 14 and SEQ ID NO: 15, respectively).

GLP-1/glucagon agonist peptides provided herein include, but are not limited to G730 (SEQ ID NO: 16), G797 (SEQ ID NO: 17), G849 (SEQ ID NO: 18), G933 (SEQ ID NO: 19), G865 (SEQ ID NO: 20), G796 (SEQ ID NO: 21), G812 (SEQ ID NO: 22) and G380 (SEQ ID NO: 23). These GLP-1/glucagon agonist peptides are listed in Table 1:

TABLE 1

GLP-1/Glucagon Peptide Sequences

| Peptide | Sequence | SEQ ID NO: |
|---|---|---|
| G730 | HSQGT FTSDY SKXLD SERAR DFVAW LVAGG-amide<br>X13 = K(gE-palm) | 16 |
| G797 | HSQGT FTSDX SEYLD SERAR DFVAW LEAGG-amide<br>X10 = K(gE-palm) | 17 |
| G849 | HSQGT FTSDX SRYLD SRSAR DFVAW LEAGG-amide<br>X10 = K(gE-palm) | 18 |
| G933 | HSQGT FTSDX SEYLD SERAR DFVAW LEAGG-acid<br>X10 = K(gE-palm) | 19 |
| G865 | HSQGT FTSDX SSYLD SRSAR DFVAW LEAGG-amide<br>X10 = K(gE-palm) | 20 |

TABLE 1-continued

GLP-1/Glucagon Peptide Sequences

| Peptide | Sequence | SEQ ID NO: |
|---|---|---|
| G796 | HSQGT FTSDX SSYLD SRRAR DFVAW LEAGG-amide X10 = K(gE-palm) | 21 |
| G812 | HSQGT FTSDX SKYLE GQAAK EFIAW LEKGR-amide X10 = K(gE-palm) | 22 |
| G380 | HGQGT FTSDY SKYLD SXRAQ DFVQW LVAGG-amide X17 = K(gE-palm) | 23 |
| G931 | HSQGT FTSDY SKXLD SERAR DFVAW LVAGG-acid X13 = K(gE-palm) | 24 |
| G934 | HSQGT FTSDX SKYLE GQAAK EFIAW LEKGR-acid X10 = K(gE-palm) | 25 |
| G973 | HSQGT FTSDX SSYLD SRSAR DFVAW LEAGG-acid X10 = K(gE-palm) | 26 |
| GLP1 | HAEGT FTSDV SSYLE GQAAK EFIAW LVKGR | SEQ ID NO: 2 (7-36 amide)/ SEQ ID NO: 3 (7-37 acid) |
| Glucagon | HSQGT FTSDY SKYLD SRRAQ DFVQW LMNT | SEQ ID NO: 1 |

K(gE-Palm) = Lysine with a palmitoyl group conjugated to the epsilon nitrogen, through a gamma glutamic acid linker.

In certain embodiments the isolated peptide is G933 (SEQ ID NO: 19).

The peptides G797 and G933 both have a glutamate residue at position 12, and maintain robust activity at both the glucagon and GLP-1 receptors, as shown in Example 2. The corresponding residue is lysine in exendin-4 and glucagon and is serine in GLP-1. Although this residue is not thought to contact the receptor, changes in charge from positive to negative may modify the adjacent environment. Furthermore, G797, G849 and G933 have a glutamate residue at position 27. Residue 27 is Lysine in exendin 4 and is an uncharged hydrophobic residue in GLP1 (valine) and glucagon (methionine). The lysine of exenatide makes electrostatic interactions with the GLP1 receptor at residues Glu127 and Glu24 (C. R. Underwood et al *J Biol Chem* 285 723-730 (2010); S. Runge et al *J Biol Chem* 283 11340-11347 (2008)). While a loss of GLP1R potency might be expected when the charge at position 27 is changed to negative, the change is compatible with GLP1R activity in G797, G849, and G933.

MEDI0382 is a synthetic peptide dual agonist of glucagon-like peptide-1 (GLP-1) and glucagon receptors. MEDI0382 is G933 (SEQ ID NO: 19), which contains a gamma glutamate linker and palmitoyl group derivatization at residue 10.

MEDI0382 is chemically synthesized. Peptide chain elongation on a resin is performed with the aid of a solid phase peptide synthesizer using manufacturer-supplied protocols for coupling of Fmoc-amino acids. Glutamine residues 20 and 24 are substituted with amino acids that are not susceptible to deamidation, and arginine residue 17 is replaced with glutamate to reduce susceptibility to proteolysis.

The sequence for MEDI0382 is shown below:

L-Histidyl-L-seryl-L-glutaminylglycyl-L-threonyl-L-phenylalanyl-L-threonyl-L-seryl-L-alpha-aspartyl-(N6-[N-(1-oxohexadecyl)-L-gamma-glutamyl])L-lysyl-L-seryl-L-alpha-glutamyl-L-tyrosyl-L-leucyl-L-alpha-aspartyl-L-seryl-L-alpha-glutamyl-L-arginyl-L-alanyl-L-arginyl-L-alpha-aspartyl-L-phenylalanyl-L-valyl-L-alanyl-L-tryptophyl-L-leucyl-L-alpha-glutamyl-L-alanylglycylglycine

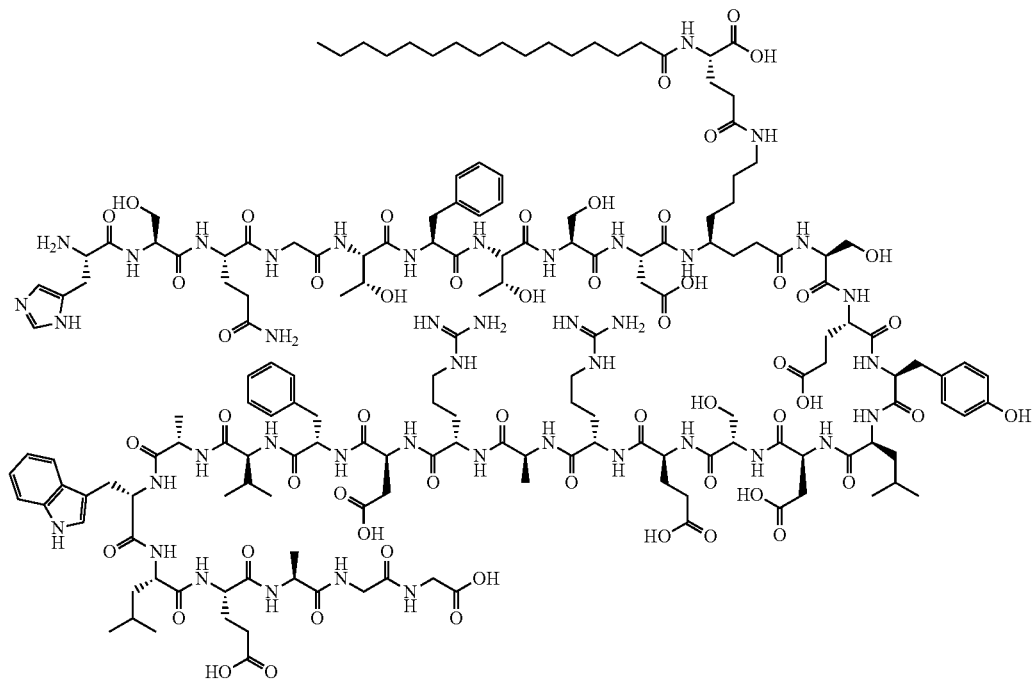

Methods of Making GLP-1/Glucagon Agonist Peptides

This disclosure provides a method of making a GLP-1/glucagon agonist peptide. GLP-1/glucagon agonist peptides provided herein can be made by any suitable method. For example, in certain embodiments the GLP-1/glucagon agonist peptides provided herein are chemically synthesized by methods well known to those of ordinary skill in the art, e.g., by solid phase synthesis as described by Merrifield (1963, *J. Am. Chem. Soc.* 85:2149-2154). Solid phase peptide synthesis can be accomplished, e.g., by using automated synthesizers, using standard reagents, e.g., as explained in Example 1.

Alternatively, GLP-1/glucagon agonist peptides provided herein can be produced recombinantly using a convenient vector/host cell combination as would be well known to the person of ordinary skill in the art. A variety of methods are available for recombinantly producing GLP-1/glucagon agonist peptides. Generally, a polynucleotide sequence encoding the GLP-1/glucagon agonist peptide is inserted into an appropriate expression vehicle, e.g., a vector which contains the necessary elements for the transcription and translation of the inserted coding sequence. The nucleic acid encoding the GLP-1/glucagon agonist peptide is inserted into the vector in proper reading frame. The expression vector is then transfected into a suitable host cell which will express the GLP-1/glucagon agonist peptide. Suitable host cells include without limitation bacteria, yeast, or mammalian cells. A variety of commercially-available host-expression vector systems can be utilized to express the GLP-1/glucagon agonist peptides described herein.

Modifications, Conjugates, Fusions, and Derivations

In certain embodiments, GLP-1/glucagon agonist peptides provided herein are stabilized via amino acid modifications. In certain embodiments, the carboxyl group of the C-terminal amino acid is amidated. In certain embodiments, the C-terminal amino acid is amidated glycine, e.g., G730, G797, G849, G865, G796, G812, and G380. In certain embodiments, e.g., G933, the C-terminal glycine is the unmodified acid. In certain embodiments, GLP-1/glucagon agonist peptides are provided in which one or more amino acid residues are acylated. For example, in certain embodiments GLP-1/glucagon agonist peptides provided herein contain one or more lysine residues, in which a palmitoyl moiety is attached to the N(epsilon) group. In certain embodiments a linker is incorporated between lysine and the palmitoyl group. This linker can be a gamma glutamic acid group, or an alternative linker such as, but not limited to, beta alanine and aminohexanoic acid. Different acylation methods may be used such as addition of cholesterol or myristoyl groups. In certain embodiments, the palmitoyl moiety is added at position 13 (e.g., G730). In certain embodiments, the palmitoyl moiety is added at position 10 (e.g., G797, G849, G933, G865, G796, and G812). In certain embodiments, the palmitoyl moiety is added at position 17 (e.g., G380).

The GLP-1/glucagon agonist peptides provided herein, e.g., G730, G797, G849 and G933 can be palmitoylated to extend their half-life by association with serum albumin, thus reducing their propensity for renal clearance, as described in Example 1.

Alternatively or in addition, a GLP-1/glucagon agonist peptide as disclosed herein can be associated with a heterologous moiety, e.g., to extend half-life. The heterologous moiety can be a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of such moieties.

For example, GLP-1/glucagon agonist peptides can be fused with a heterologous polypeptide. The peptides can be fused to proteins, either through recombinant gene fusion and expression or by chemical conjugation. Proteins that are suitable as partners for fusion include, without limitation, human serum albumin, antibodies and antibody fragments including fusion to the Fc portion of the antibodies. GLP-1 has been fused to these proteins with retention of potency (L. Baggio et al, *Diabetes* 53 2492-2500 (2004); P. Barrington et al *Diabetes, Obesity and Metabolism* 13 426-433 (2011); P. Paulik et al American Diabetes Association 2012, Poster 1946). Extended recombinant peptide sequences have also been described to give the peptide high molecular mass (V. Schellenberger et al *Nature Biotechnol* 27 1186-1190 (2009); PASylation (EP2173890)). In certain embodiments GLP-1/glucagon agonist peptides are incorporated as the N-terminal part of a fusion protein, with the fusion partner, e.g., the albumin or Fc portion, at the C-terminal end. GLP-1/glucagon agonist peptides as described herein can also be fused to peptides or protein domains, such as 'Albudabs' that have affinity for human serum albumin (M. S. Dennis et al *J Biol Chem* 277 35035-35043 (2002); A. Walker et al Protein Eng Design Selection 23 271-278 (2010)). Methods for fusing a GLP-1/glucagon agonist peptides as disclosed herein with a heterologous polypeptide, e.g., albumin or an Fc region, are well known to those of ordinary skill in the art.

Other heterologous moieties can be conjugated to GLP-1/glucagon agonist peptides to further stabilize or increase half-life. For chemical fusion, certain embodiments feature maintenance of a free N-terminus, but alternative points for derivatization can be made. A further alternative method is to derivatize the peptide with a large chemical moiety such as high molecular weight polyethylene glycol (PEG). A "pegylated GLP-1/glucagon agonist peptide" has a PEG chain covalently bound thereto. Derivatization of GLP-1/glucagon agonist peptides, e.g., pegylation, can be done at the lysine that is palmitoylated, or alternatively at a residue such as cysteine, that is substituted or incorporated by extension to allow derivatization. GLP-1/glucagon agonist peptide formats above can be characterized in vitro and/or in vivo for relative potency and the balance between GLP-1 and glucagon receptor activation.

The general term "polyethylene glycol chain" or "PEG chain", refers to mixtures of condensation polymers of ethylene oxide and water, in a branched or straight chain, represented by the general formula $H(OCH_2CH_2)_nOH$, where n is an integer of 3, 4, 5, 6, 7, 8, 9, or more. PEG chains include polymers of ethylene glycol with an average total molecular weight selected from the range of about 500 to about 40,000 Daltons. The average molecular weight of a PEG chain is indicated by a number, e.g., PEG-5,000 refers to polyethylene glycol chain having a total molecular weight average of about 5,000.

PEGylation can be carried out by any of the PEGylation reactions known in the art. See, e.g., *Focus on Growth Factors*, 3: 4-10, 1992 and European patent applications EP 0 154 316 and EP 0 401 384. PEGylation may be carried out using an acylation reaction or an alkylation reaction with a reactive polyethylene glycol molecule (or an analogous reactive water-soluble polymer).

Methods for preparing a PEGylated GLP-1/glucagon agonist peptides generally include the steps of (a) reacting a GLP-1/glucagon agonist peptide or with polyethylene glycol (such as a reactive ester or aldehyde derivative of PEG) under conditions whereby the molecule becomes attached to one or more PEG groups, and (b) obtaining the reaction product(s).

Pharmaceutical Compositions

Further provided are compositions, e.g., pharmaceutical compositions, that contain an effective amount of a GLP-1/glucagon agonist peptide as provided herein, formulated for the treatment of metabolic diseases, e.g., obesity.

Compositions of the disclosure can be formulated according to known methods. Suitable preparation methods are described, for example, in *Remington's Pharmaceutical Sciences,* 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the invention can be administered directly to the subject.

Carriers that can be used with compositions of the invention are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Methods of Treating

Substantial non-surgical weight loss with effective glucose control has remained a key unmet need for patients with type 2 diabetes mellitus. The methods of treatment provided herein can meet this need.

GLP-1/glucagon agonist peptides (e.g., MEDI0382) can combine the effect of glucagon e.g., inhibition of food intake or regulation of glucose levels with the effect of GLP-1 e.g., inhibition of gastric motility, or promotion of insulin release. They can therefore act to accelerate elimination of excessive adipose tissue, induce sustainable weight loss, and improve glycemic control. GLP-1/glucagon agonist peptides (e.g., MEDI0382) can also act to reduce cardiovascular risk factors such as high cholesterol, and high LDL-cholesterol or abnormal HDL/LDL ratios. GLP-1/glucagon agonist peptides (e.g., MEDI0382) can also act to reduce triglycerides.

This disclosure provides a method of treating obesity or an obesity-related disease or disorder, comprising administering to a subject in need of treatment 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide as disclosed herein (e.g., MEDI0382). In certain instances, the administration is an adjunct to diet and exercise. Further provided is 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide (e.g., MEDI0382) for treatment of obesity or an obesity-related disease or disorder. Further provided is use of 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide as provided herein (e.g., MEDI0382) in the manufacture of a medicament for the treatment of obesity or an obesity-related disease or disorder. The 50-600 µg or 100-600 µg of the GLP-1/glucagon agonist peptide as disclosed herein (e.g., MEDI0382) can be administered in single or divided doses. In addition, the 50-600 µg or 100-600 µg of the GLP-1/glucagon agonist peptide as disclosed herein (e.g., MEDI0382) can be administered in increasing doses (e.g., a dose titration such as an initial dose of 100 µg, a second dose of 150 or 200 µg, and optionally a third dose of 200, 300 or 400 µg, e.g., wherein the initial dose and/or the second dose are administered for 3-10 days or 3-7 days.) In certain instances, the subject has type 2 diabetes mellitus. In certain instances, the subject has a body mass index (BMI) of 30 to 39.9 kg/m$^2$. In certain instances, the subject has a BMI of at least 40.

This disclosure also provides a method of reducing body weight, comprising administering to a subject in need of treatment 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide as disclosed herein (e.g., MEDI0382). The 50-600 µg or 100-600 µg of the GLP-1/glucagon agonist peptide as disclosed herein (e.g., MEDI0382) can be administered in single or divided doses. In addition, the 50-600 µg or 100-600 µg of the GLP-1/glucagon agonist peptide as disclosed herein (e.g., MEDI0382) can be administered in increasing doses (e.g., a dose titration such as an initial dose of 100 µg, a second dose of 150 or 200 µg, and optionally a third dose of 200, 300 or 400 µg, e.g., wherein the initial dose and/or the second dose are administered for 3-10 days or 3-7 days.) In certain instances, the administration is an adjunct to diet and exercise. In certain instances, the subject has type 2 diabetes mellitus. In certain instances, the subject has a BMI of 27 to 40 kg/m$^2$. In certain instances, the subject has a BMI of 30 to 39.9 kg/m$^2$. In certain instances, the subject has a BMI of at least 40. In certain instances, the subject is overweight. In certain instances, the subject is obese.

This disclosure also provides a method of reducing body fat, comprising administering to a subject in need of treatment 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide as disclosed herein (e.g., MEDI0382). The 50-600 µg or 100-600 µg of the GLP-1/glucagon agonist peptide as disclosed herein (e.g., MEDI0382) can be administered in single or divided doses. In addition, the 50-600 µg or 100-600 µg of the GLP-1/glucagon agonist peptide as disclosed herein (e.g., MEDI0382) can be administered in increasing doses (e.g., a dose titration such as an initial dose of 100 µg, a second dose of 150 or 200 µg, and optionally a third dose of 200, 300 or 400 µg, e.g., wherein the initial dose and/or the second dose are administered for 3-10 days or 3-7 days.) In certain instances, the administration is an adjunct to diet and exercise. In certain instances, the subject has type 2 diabetes mellitus. In certain instances, the subject has a BMI of 27 to 40 kg/m$^2$. In certain instances, the subject has a BMI of 30 to 39.9 kg/m². In certain instances, the subject has a BMI of at least 40. In certain instances, the subject is overweight. In certain instances, the subject is obese. In certain instances, the fat is liver fat. The reduction of liver fat can lead to enhanced insulin sensitivity and/or improved liver function. In certain instances, liver fat in the subject is reduced by at least 20%. In certain instances, liver fat in the subject is reduced by about 20% to about 40%. In certain instances, the administration results in about a one third reduction in liver fat. In certain instances, liver volume is reduced in the subject. In certain instances, the administration reduces hemoglobin A1c (HbA1c) levels (e.g., by at least 0.6%, by at least 0.9%, by about 0.5% to about 1.5%, by about 0.5% to about 2%, by about 0.5% to about 3%, or to 6.3% or lower.

This disclosure also provides a method of managing weight, comprising administering to a subject in need thereof 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) of a GLP-1/glucagon agonist peptide as disclosed herein (e.g., MEDI0382). The 50-600 μg or 100-600 μg of the GLP-1/glucagon agonist peptide as disclosed herein (e.g., MEDI0382) can be administered in single or divided doses. In addition, the 50-600 μg or 100-600 μg of the GLP-1/glucagon agonist peptide as disclosed herein (e.g., MEDI0382) can be administered in increasing doses (e.g., a dose titration such as an initial dose of 100 μg, a second dose of 150 or 200 μg, and optionally a third dose of 200, 300 or 400 μg, e.g., wherein the initial dose and/or the second dose are administered for 3-10 days or 3-7 days). In certain instances, the administration is an adjunct to diet and exercise. In certain instances, the subject has type 2 diabetes mellitus. In certain instances, the subject has a BMI of 27 to 40 kg/m². In certain instances, the subject has a BMI of 30 to 39.9 kg/m². In certain instances, the subject has a BMI of at least 40. In certain instances, the subject is overweight. In certain instances, the subject is obese.

This disclosure also provides a method of treating Non-alcoholic Steatohepatitis (NASH), comprising administering to a subject in need of treatment 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) of a GLP-1/glucagon agonist peptide as disclosed herein (e.g., MEDI0382). The 50-600 μg or 100-600 μg of the GLP-1/glucagon agonist peptide as disclosed herein (e.g., MEDI0382) can be administered in single or divided doses. In addition, the 50-600 μg or 100-600 μg of the GLP-1/glucagon agonist peptide as disclosed herein (e.g., MEDI0382) can be administered in increasing doses (e.g., a dose titration such as an initial dose of 100 μg, a second dose of 150 or 200 μg, and optionally a third dose of 200, 300 or 400 μg, e.g., wherein the initial dose and/or the second dose are administered for 3-10 days or 3-7 days). In certain instances, the administration is an adjunct to diet and exercise. The administration can also reduce body weight or treat obesity. In certain instances, the subject has a BMI of 27 to 40 kg/m². In certain instances, the subject has a BMI of 30 to 39.9 kg/m². In certain instances, the subject has a BMI of at least 40. In certain instances, the subject is overweight. In certain instances, the subject is obese.

As provided herein, 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) of GLP-1/glucagon agonist peptides provided herein (e.g., MEDI0382) can be administered for preventing weight gain, preventing fat gain (e.g., liver fat), promoting weight loss, promoting fat loss (e.g., liver fat), reducing excess body weight, reducing fat (e.g., liver fat), or treating obesity (e.g. by control of appetite, feeding, food intake, calorie intake, and/or energy expenditure), including morbid obesity. Increased energy expenditure can result, for example, from increased oxidation of fatty acids and/or glucose in the liver. This disclosure also provides a method of treating or preventing a disease or condition caused or characterized by excess body weight or excess body fat, comprising administering to a subject in need of treatment 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) of a GLP-1/glucagon agonist peptide as disclosed herein (e.g., MEDI0382). In certain instances, the administration is an adjunct to diet and exercise. In addition, 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) GLP-1/glucagon agonist peptides provided herein (e.g., MEDI0382) can be used for treatment of other obesity-related metabolic disorders. The 50-600 μg or 100-600 μg of the GLP-1/glucagon agonist peptide as disclosed herein (e.g., MEDI0382) can be administered in single or divided doses. In addition, the 50-600 μg or 100-600 μg of the GLP-1/glucagon agonist peptide as disclosed herein (e.g., MEDI0382) can be administered in increasing doses (e.g., a dose titration such as an initial dose of 100 μg, a second dose of 150 or 200 μg, and optionally a third dose of 200, 300 or 400 μg, e.g., wherein the initial dose and/or the second dose are administered for 3-10 days or 3-7 days.) Examples of other obesity-related (excess body weight-related) disorders include without limitation: insulin resistance, glucose intolerance, pre-diabetes, increased fasting glucose, type 2 diabetes, hypertension, dyslipidemia (or a combination of these metabolic risk factors), glucagonomas, cardiovascular diseases such as congestive heart failure, atherosclerosis, arteriosclerosis, coronary heart disease, or peripheral artery disease, stroke, respiratory dysfunction, or renal disease.

This disclosure also provides a method of treating type 2 diabetes mellitus, comprising administering to a subject in need of treatment 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) of a GLP-1/glucagon agonist peptide as disclosed herein (e.g., MEDI0382). The 50-600 μg or 100-600 μg of the GLP-1/glucagon agonist peptide as disclosed herein (e.g., MEDI0382) can be administered in single or divided doses. In addition, the 50-600 μg or 100-600 μg of the GLP-1/glucagon agonist peptide as disclosed herein (e.g., MEDI0382) can be administered in increasing doses (e.g., a dose titration such as an initial dose of 100 μg, a second dose of 150 or 200 μg, and optionally a third dose of 200, 300 or 400 μg, e.g., wherein the initial dose and/or the second dose are administered for 3-10 days or 3-7 days.) In certain instances, the administration is an adjunct to diet and exercise. The administration can also reduce body weight or treat obesity. In certain instances, the subject has a BMI of 27 to 40 kg/m². In certain instances, the subject has a BMI of 30 to 39.9 kg/m². In certain instances, the subject has a BMI of at least 40. In certain instances, the subject is overweight. In certain instances, the subject is obese.

This disclosure also provides a method of improving glycemic control or achieving glycemic control, comprising administering to a subject in need of treatment 50-600 μg or 100-600 μg (e.g., 50, 100, 125, 150, 175, 200, 225, 250, 275, 300, 325, 350, 375, 400, 425, 450, 475, 500, 525, 550, 575, or 600 μg) of a GLP-1/glucagon agonist peptide as disclosed herein (e.g., MEDI0382). The 50-600 µg or 100-600 µg of the GLP-1/glucagon agonist peptide as disclosed herein (e.g., MEDI0382) can be administered in single or divided doses. In addition, the 50-600 µg or 100-600 µg of the GLP-1/glucagon agonist peptide as disclosed herein (e.g., MEDI0382) can be administered in increasing doses (e.g., a dose titration such as an initial dose of 100 µg, a second dose of 150 or 200 µg, and optionally a third dose of 200, 300 or 400 µg, e.g., wherein the initial dose and/or the second dose are administered for 3-10 days or 3-7 days.) In certain instances, the administration is an adjunct to diet and exercise. The administration can also reduce body weight or treat obesity. In certain instances, the subject has type 2 diabetes mellitus. In certain instances, the subject has a BMI of 27 to 40 kg/m$^2$. In certain instances, the subject has a BMI of 30 to 39.9 kg/m$^2$. In certain instances, the subject has a BMI of at least 40. In certain instances, the subject is overweight. In certain instances, the subject is obese. An improvement in glycemic control can be assessed using a mixed-meal test. In certain instances, the improvement in glycemic control results in at least a 10% reduction in glucose area under the concentration-time-curve (AUC) after a mixed-meal test (e.g., as compared to the AUC prior to treatment). In certain instances, the improvement in glycemic control results in at least a 15% reduction in AUC after a mixed-meal test (e.g., as compared to the AUC prior to treatment). In certain instances, the improvement in glycemic control results in at least a 20% reduction in glucose AUC after a mixed-meal test (e.g., as compared to the AUC prior to treatment). In certain instances, the improvement in glycemic control results in at least a 25% reduction in glucose AUC after a mixed-meal test (e.g., as compared to the AUC prior to treatment). In certain instances, the improvement in glycemic control results in at least a 30% reduction in glucose AUC after a mixed-meal test (e.g., as compared to the AUC prior to treatment). An improvement in glycemic control can also be assessed based on hemoglobin A1c and fructosamine.

This disclosure also provides a method of decreasing weight and controlling glucose, comprising administering to a subject in need of treatment 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide as disclosed herein (e.g., MEDI0382). The 50-600 µg or 100-600 µg of the GLP-1/glucagon agonist peptide as disclosed herein (e.g., MEDI0382) can be administered in single or divided doses. In addition, the 50-600 µg or 100-600 µg of the GLP-1/glucagon agonist peptide as disclosed herein (e.g., MEDI0382) can be administered in increasing doses (e.g., a dose titration such as an initial dose of 100 µg, a second dose of 150 or 200 µg, and optionally a third dose of 200, 300 or 400 µg, e.g., wherein the initial dose and/or the second dose are administered for 3-10 days or 3-7 days.) In certain instances, the administration is an adjunct to diet and exercise. The administration can also reduce body weight or treat obesity. In certain instances, the subject has type 2 diabetes mellitus. In certain instances, the subject has a BMI of 27 to 40 kg/m$^2$. In certain instances, the subject has a BMI of 30 to 39.9 kg/m$^2$. In certain instances, the subject has a BMI of at least 40. In certain instances, the subject is overweight. In certain instances, the subject is obese. In certain instances, the administration results in weight loss of at least 1.0 kg, at least 1.3 kg, or about 1.3 to about 2.0 kg. In certain instances, the subject's weight is reduced by at least 3.5 kg or at least 5 kg. In certain instances, the subject's weight is reduced by about 2 to about 30 kg. In certain instances, the subject's weight is reduced by at least 2%, at least 4%, at least 5%, or at least 10%. In certain instances, the subject's weight is reduced by about 2% to about 20%, about 2% to about 25%, or about 2% to about 30%.

In certain instances, administration of the GLP-1/glucagon agonist peptides provided herein (e.g., MEDI0382) results in weight loss of at least 1 kg. In certain instances, administration of the GLP-1/glucagon agonist peptides provided herein (e.g., MEDI0382) results in weight loss of at least 1.3 kg. In certain instances, administration of the GLP-1/glucagon agonist peptides provided herein results in weight loss of at least 1.5 kg. In certain instances, administration of the GLP-1/glucagon agonist peptides provided herein (e.g., MEDI0382) results in weight loss of 1 to 3 kg following four weeks of repeat once-daily dosing. In certain instances, administration of the GLP-1/glucagon agonist peptides provided herein (e.g., MEDI0382) results in weight loss of 1.3 to 2 kg following four weeks of repeat once-daily dosing.

The route of administration of GLP-1/glucagon agonist peptides provided herein (e.g., MEDI0382) can be, for example, oral, parenteral, by inhalation or topical. The term parenteral as used herein includes, e.g., intravenous, intraarterial, intraperitoneal, intramuscular, subcutaneous, rectal, or vaginal administration. Another example of a form for administration is a solution for injection, in particular for intravenous or intraarterial injection or drip. GLP-1/glucagon agonist peptides provided herein (e.g., MEDI0382) can be administered as a single dose or as multiple doses. In certain embodiments, 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of a GLP-1/glucagon agonist peptide is administered by subcutaneous injection.

Parenteral formulations can be a single bolus dose, an infusion or a loading bolus dose followed with a maintenance dose. These compositions can be administered at specific fixed or variable intervals, e.g., once a day, or on an "as needed" basis. Dosage regimens also can be adjusted to provide the optimum desired response (e.g., a therapeutic or prophylactic response).

In certain instances, 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of GLP-1/glucagon agonist peptides provided herein (e.g., MEDI0382) can be administered once per day. In certain instances, 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of GLP-1/glucagon agonist peptides provided herein (e.g., MEDI0382) can be administered once per day via injection (e.g., subcutaneous administration). In certain instances, 50-600 µg or 100-600 µg (e.g., 50, 100, 125, 150, 175, 200, 225, 250, 275, 300, 325, 350, 375, 400, 425, 450, 475, 500, 525, 550, 575, or 600 µg) of GLP-1/glucagon agonist peptides provided herein (e.g., MEDI0382) can be administered once per day via injection (e.g., subcutaneous administration) over a period of at least one week, over a period of at least two weeks, over a period of at least three weeks, or over a period of at least four weeks. In certain instances, 50-600 µg or 100-600 µg (e.g., 100, 125, 150, 175, 200, 225, 250, 275, 300, 325, 350, 375, 400, 425, 450, 475, 500, 525, 550, 575, or 600 µg) of GLP-1/glucagon agonist peptides provided herein (e.g., MEDI0382) can be administered in single or divided doses. In certain instances, 50-600 µg or 100-600 µg (e.g., 100, 125, 150, 175, 200, 225, 250, 275, 300, 325, 350, 375, 400, 425, 450, 475, 500, 525, 550, 575, or 600 µg) of GLP-1/glucagon agonist peptides provided herein (e.g., MEDI0382) can administered in increasing doses (e.g., a dose titration such as an initial dose of 100 µg, a second dose of 150 or 200 µg, and optionally a third dose of 200, 300 or 400 µg, e.g., wherein the initial dose and/or the second dose are administered for 3-10 days or 3-7 days.) In certain instances, GLP-1/glucagon agonist peptides provided herein (e.g., MEDI0382) can be administered as an initial dose of 100 µg for four days, a second dose of 150 µg for four days, and a third dose of 200 µg subsequently administered daily. In certain instances, GLP-1/glucagon agonist peptides provided herein (e.g., MEDI0382) can be administered as an initial dose of 100 µg for five days, a second dose of 150 µg for five days, a third dose of 200 µg for five days, and a fourth dose of 300 µg subsequently administered daily. In certain instances, GLP-1/glucagon agonist peptides provided herein (e.g., MEDI0382) can be administered as an initial dose of 100 µg for five days, a second dose of 200 µg for five days, and a third dose of 300 µg subsequently administered daily.

In certain instances, the half-life of the GLP-1/glucagon agonist peptides provided herein (e.g., MEDI0382) is about 7 to 13 hours. In certain instances, the half-life of the GLP-1/glucagon agonist peptides provided herein (e.g., MEDI0382) is about 9 to 13 hours. In certain instances, the half-life of the GLP-1/glucagon agonist peptides provided herein (e.g., MEDI0382) is about 7 to 12 hours. In certain instances, the half-life of the GLP-1/glucagon agonist peptides provided herein (e.g., MEDI0382) is about 10 to 12 hours. In certain instances, the half-life of the GLP-1/glucagon agonist peptides provided herein (e.g., MEDI0382) is about 8 to 11 hours.

Kits

In yet other embodiments, the present disclosure provides kits comprising GLP-1/glucagon agonist peptides, that can be used to perform the methods described herein. In certain embodiments, a kit comprises a GLP-1/glucagon agonist peptide disclosed herein in one or more containers. One skilled in the art will readily recognize that the disclosed GLP-1/glucagon agonist peptides can be readily incorporated into one of the established kit formats which are well known in the art.

EXAMPLES

Example 1: Synthesis, Modifications, and Characterization of GLP-1/Glucagon Agonist Peptides List of Abbreviations Boc: tert-butyloxycarbonyl
tert-Bu; tert-butyl
DCM: dichloromethane
DIC: diisopropylcarbodiimide
Fmoc: 9-fluorenylmethoxycarbonyl
HOBt: 1-hydroxybenzotriazole
HPLC: High Performance Liquid Chromatography
Mtt: 4-methyltrityl
NMP: N-methylpyrrolidone
Pbf: 2,2,4,6,7-pentamethyldihydrobenzofuran-5-sulfonyl
TFA: trifluoroacetic acid
TIS: triisopropylsilane
Trt: triphenylmethyl, trityl GLP-1/glucagon agonist peptides were synthesized as follows. Elongation of peptide chains on NovaSyn TGR or preloaded Fmoc-Wang resin (NovaBiochem) was performed with a PRELUDE™ solid phase peptide synthesizer (Protein Technologies, Tucson, Ariz., USA). Manufacturer-supplied protocols were applied for coupling of the hydroxybenzotriazole esters of amino acids in N-methylpyrolidone (NMP). The fluorenylmethoxycarbonyl (Fmoc) group was used for the semipermanent protection of alpha-amino groups of amino acids, whereas the side chains were protected with tert-butyl (tert-Bu) for serine, threonine, aspartic acid, glutamic acid, tyrosine, and 2,2,4,6,7-pentamethyldihydrobenzofuran-5-sulfonyl (Pbf) for arginine, and trityl (Trt) for histidine. The N-terminal amino group of histidine in position 1 was protected with tert-butyloxycarbonyl group (Boc). Lys(Mtt) was incorporated into the peptide chain when a subsequent chemical modification of the side chain was required.

Upon completion of the peptide chain elongation, the Mtt group was removed by washing the peptide-resin with DCM containing 2% TFA and 5% TIS (10×7 ml, each 0.5 min). Coupling of a lipid moiety to the side chain of Lys was performed on the PRELUDE™ peptide synthesizer using DIC as a coupling reagent in the presence of HOBt.

Peptides were cleaved from the resin using mixture of TFA:TIS:water (95:2.5:2.5). After 2 h at room temperature, the peptidyl resin was filtered, washed with TFA and combined filtrates were evaporated to dryness in vacuo. The residue was triturated with ether, and the precipitate which formed was filtered, washed with ether, and dried. The crude peptides were dissolved in 5% acetic acid in water and analyzed by reverse-phase high-pressure liquid chromatography on a Polaris 3 C8-A column attached to Varian 920-LC system. A standard gradient system of 10 to 90% buffer B over the course of 15 min was used for analysis. Buffer A was 0.1% TFA in water and buffer B was 0.1% TFA in acetonitrile. HPLC profiles were recorded at 210 nm. Preparative separations were performed on Varian ProStar system with a semipreparative C18 RP XBridge Waters column. The above-described solvent system of water and acetonitrile, in a gradient of 30 to 70% buffer B over the course of 30 min, was used for separation. The chromatographically homogenous products (>97% pure) were analyzed by electrospray mass spectrometry (MassLynx, Waters).

Example 2: In Vitro Studies

Glucagon and GLP-1 Receptor Mediated cAMP Production

Biological Activity of Peptides in Cell-Based cAMP Activity Assay (Assay 1):

The biological activity of GLP-1/glucagon agonist peptides synthesized by the method of Example 1 were tested for biological activity, e.g., stimulation of one or more cellular receptor responses, by the following methods. Stable cell lines expressing human, mouse, rat, or dog GLP-1 receptor (GLP-1R), glucagon receptor (GCGR) or glucose-dependent insulinotropic peptide (gastric inhibitory polypeptide) receptor (GIPR) were generated in HEK293s or CHO cells by standard methods. Peptide activation of these various receptors results in downstream production of cAMP second messenger which can be measured in a functional activity assay.

cAMP Assays were Performed Using "Assay Medium":
Assay Medium: 10% FBS in DMEM (Gibco #41966), containing 0.5 mM IBMX (Sigma #17018).
Low protein binding 384-well plates (Greiner #781280) were used to perform eleven 1 in 5 serial dilutions of test samples which were made in assay medium. All sample dilutions were made in duplicate.

A frozen cryo-vial of cells expressing the receptor of interest was thawed rapidly in a water-bath, transferred to pre-warmed assay media and spun at 240×g for 5 minutes. Cells were re-suspended in assay media at an optimized concentration (e.g. hGCGR cells at $1 \times 10^5$ cells/ml, hGLP-1R and hGIPR cells at $0.5 \times 10^5$ cells/ml).

From the dilution plate, a 5 μL replica was stamped onto a black shallow-well u-bottom 384-well plate (Corning #3676). To this, 5 μL cell suspension was added and the plates incubated at room temperature for 30 minutes.

cAMP levels were measured using a commercially available cAMP dynamic 2 HTRF kit (Cisbio, Cat #62AM4PEJ), following the two step protocol as per manufacturer's recommendations. In brief; anti-cAMP cryptate (donor fluorophore) and cAMP-d2 (acceptor fluorophore) were made up separately by diluting each 1/20 in conjugate & lysis buffer provided in the kit. 5 μL anti-cAMP cryptate was added to all wells of the assay plate, and 5 μL cAMP-d2 added to all wells except non-specific binding (NSB) wells, to which conjugate and lysis buffer was added. Plates were incubated at room temperature for one hour and then read on an Envision (Perkin Elmer) using excitation wavelength of 320 nm and emission wavelengths of 620 nm & 665 nm.

Sequences of synthesized GLP-1/glucagon agonist peptides and their EC50 values determined in cAMP assays, performed in "assay medium," are shown in Table 2. All peptides in Table 2 were synthesized with a C-terminal amide. Additional GLP-1/glucagon agonist peptides were synthesized with a C-terminal acid and EC50 values determined in cAMP assays, performed in "assay medium," are shown in Table 3. EC50 for additional GLP-1/glucagon agonist peptides, performed in "assay medium," are shown in Table 4. All peptides in Table 4 have a C-terminal amide, unless they are denoted as 'acid' in which case they have a C-terminal acid.

TABLE 2 cAMP activity of GLP-1/glucagon agonist peptides with C-terminal amide (assay 1)

| | Assay in Assay Medium | | |
|---|---|---|---|
| Peptide | Human GlucR EC50 M | Human GLP1R EC50 M | Human GIPr EC50 M |
| G730 | 6.23E−12 | 1.8E−11 | 4.5E−08 |
| G797 | 6.14E−12 | 1.4E−11 | 3.4E−09 |
| G849 | 2.26E−12 | 9.0E−12 | 1.7E−08 |
| G865 | 1.26E−11 | 8.3E−12 | 2.2E−08 |
| G796 | 1.76E−12 | 1.3E−11 | 1.4E−08 |
| G812 | 8.17E−12 | 1.1E−11 | 2.7E−09 |
| G380 | 2.17E−10 | 7.7E−11 | 1.3E−07 |
| GLP1 | | 8.1E−11 | |
| Glucagon | 3.3E−12 | | |

TABLE 3 cAMP activity of GLP-1/glucagon agonist peptides with C-terminal acid (assay 1)

| Peptide | Human GlucR EC50 M | Human GLP1R EC50 M | Human GIPr EC50 M |
|---|---|---|---|
| G931 | 1.78E−11 | 1.30E−10 | 0.00E+00 |
| G933 | 5.92E−12 | 3.20E−11 | 9.70E−09 |
| G934 | 6.30E−12 | 1.80E−11 | 3.60E−09 |
| G973 | 8.90E−12 | 1.20E−11 | 4.70E−08 |

TABLE 4 cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| Parent sequence HSQGT FTSDY SKYLD SRRAQ DFVQW LVAGG Peptides in this section all contain LVAGG at residues 26 to 30 | | | | |
| Glucagon | 3.3E−12 | 4.2E−09 | 1.99E−07 | |
| GLP1 | 1.53E−07 | 8.1E−11 | 1.53E−07 | |
| g715 | 2.53E−12 | 2.04E−11 | 9.98E−10 | K(gE-palm)10 |
| g716 | 2.46E−09 | 1.29E−08 | 1.18E−08 | K(gEpalm)11 |
| g702 | 1.49E−09 | 3.35E−09 | 0.00E+00 | K(gEpalm)12, E17 |
| g728 | 2.44E−09 | 1.69E−10 | 3.95E−07 | K(gEpalm)12, E17 R20 A24 |
| g729 | 3.19E−11 | 7.29E−11 | 2.09E−07 | K(gEpalm)13 E17 |
| g730 | 1.50E−11 | 3.95E−11 | 5.66E−08 | K(gEpalm)13 E17 R20 A24 |
| g875 | 1.29E−10 | 2.98E−11 | 2.90E−08 | K(gEpalm)13 R20 A24, E17 Aib2 |
| g841 | no data | | | K(gEpalm)13 R20 A24, S18 R12 acid |
| g802 | 1.81E−09 | 9.64E−11 | 9.12E−08 | K(gEpalm)13, R20 A24, E17, E12 |
| g820 | 1.17E−11 | 3.39E−11 | 7.11E−08 | K(gEpalm)13, R20 A24, E17, R12 |
| g842 | 8.31E−12 | 5.12E−11 | 8.83E−08 | K(gEpalm)13, R20 A24, E17, R12 acid |
| g733 | 6.20E−08 | 2.31E−11 | 8.17E−07 | K(gEpalm)14, G2 E3 |
| g803 | 1.08E−11 | 2.96E−11 | 3.29E−08 | K(gEpalm)14, R20 E24, S18 |

TABLE 4-continued cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| g843 | no data | | | K(gEpalm)14, R20 E24, S18 R12 acid |
| g732 | 3.96E−11 | 2.32E−11 | 2.94E−08 | K(gEpalm)14, R20 A24, E17 G2 |
| g777 | 1.24E−12 | 2.74E−11 | 4.53E−09 | K(gEpalm)14, R20 A24, E17 |
| g844 | no data | | | K(gEpalm)14, R20 A24, E17 R12 Aib2 acid |
| g845 | no data | | | K(gEpalm)14, R20 A24, E17 R12 acid |
| g821 | 4.63E−12 | 5.58E−11 | 1.40E−08 | K(gEpalm)14, R20 A24, E17, R12 |
| g846 | 3.41E−11 | 4.38E−11 | 1.18E−08 | K(gEpalm)14, R20 A24, E17, E12 |
| g731 | 2.77E−11 | 4.22E−11 | 4.07E−08 | K(gEpalm)14, E12 |
| g670 | 8.00E−12 | 2.03E−11 | 1.49E−08 | K(gEpalm)14, S18 |
| g335 | 1.05E−11 | 7.33E−11 | 5.82E−07 | K(gE-palm)17 |
| g336 | 1.77E−12 | 3.66E−11 | 1.96E−08 | K(gE-gE-palm)17 |
| g384 | 4.29E−11 | 2.72E−11 | 1.70E−08 | K(gEpalm)17, Aib2 |
| g380 | 3.62E−10 | 1.00E−10 | 6.09E−07 | K(gEpalm)17, G2 |
| g736 | 9.19E−10 | 8.54E−11 | 0.00E+00 | K(gEpalm)17, G2, A20 A24 |
| g381 | 1.93E−09 | 9.08E−11 | 5.45E−07 | K(gEpalm)17, E3 |
| g678 | 4.52E−09 | 1.06E−10 | 1.23E−07 | K(gEpalm)17, G2 E20 |
| g599, g688 | 6.98E−11 | 1.20E−10 | 1.12E−07 | K(gEpalm)17, E20 |
| g679 | 1.89E−10 | 1.35E−10 | 1.17E−07 | K(gEpalm)17, G2 E24 |
| g600, g689 | 5.47E−12 | 6.66E−11 | 8.28E−08 | K(gEpalm)17, E24 |
| g680 | 3.68E−09 | 1.95E−10 | 9.67E−08 | K(gEpalm)17, G2 E20 E24 |
| g639 | 8.21E−08 | 2.44E−10 | 8.21E−08 | K(gEpalm)17, S2 E3 E20 E24 |
| g681 | 3.99E−08 | 2.83E−10 | 1.24E−07 | K(gEpalm)17, G2, E3 E20 E24 |
| g720 | 3.52E−10 | 5.34E−11 | 0.00E+00 | K(gEpalm)17, G2 R20 E24 R12 |
| g660 | 1.52E−09 | 1.06E−09 | 3.32E−07 | K(gEpalm)17, G2 R20 E24 |
| g835 | 4.24E−10 | 1.91E−10 | 9.72E−08 | K(gEpalm)17, R20 E24, E12 |
| g776 | 4.65E−12 | 7.02E−11 | 4.79E−08 | K(gEpalm)17, R20 E24 |
| g823 | 9.48E−12 | 9.73E−11 | 8.42E−08 | K(gEpalm)17, R20 E24, R12 |
| g867 | 7.04E−12 | 4.48E−11 | 4.17E−08 | K(gEpalm)17, R20 A24 |
| g736 | 9.20E−10 | 8.54E−11 | 0.00E+00 | K(gEpalm)17, A20 A24, G2 |
| g737 | 7.34E−07 | 8.14E−11 | 0.00E+00 | K(gEpalm)17, A20 A24, G2 E3 |
| g675 | 3.84E−08 | 1.51E−10 | 1.61E−06 | K (gEpalm)17, E12 R20 A24 G2 |

Parent sequence HSQGT FTSDY SKYLD SRRAQ DFVQW LEAGG Peptides in this section all have the sequence LEAGG from residue 26 onwards unless otherwise stated, e.g. LERGG

| | | | | |
|---|---|---|---|---|
| g717 | 4.55E−13 | 5.77E−12 | 1.48E−09 | K(gEpalm)10, LEAGG |
| g796 | 1.81E−12 | 1.40E−11 | 1.74E−08 | K(gEpalm)10, LEAGG, R20 A24 S12 |
| g847 | no data | | | K(gEpalm)10, LEAGG, R20 A24 S18 E12 Aib2 acid |
| g797 | 9.64E−12 | 2.26E−11 | 4.64E−09 | K(gEpalm)10, LEAGG, R20 A24 E17 E12 |
| g798 | 5.10E−13 | 9.07E−12 | 1.51E−09 | K(gEpalm)10, LEAGG, R20 A24 E17 |
| g848 | 9.66E−13 | 9.42E−12 | 2.77E−09 | K(gEpalm)10, LEAGG, R20 A24 E17 R12 |
| g849 | 2.28E−12 | 9.07E−12 | 1.81E−08 | K(gEpalm)10, LEAGG, R20 A24 S18 R12 |
| g701 | 3.83E−09 | 7.40E−09 | 0.00E+00 | K(gEpalm)12, LERGG, G2 E17 |
| g840 | 5.30E−12 | 1.45E−10 | 1.02E−07 | LEAGG, R20 A24, E17 |
| g824 | 1.05E−12 | 4.71E−11 | 5.74E−08 | K(gEpalm)14, LEAGG, R20, E24 |
| g780 | 7.92E−13 | 1.20E−11 | 6.40E−08 | K(gEpalm)14, LEAGG, R20 A24 |
| g601 | 4.93E−13 | 3.98E−11 | 7.41E−08 | K(gEpalm)14, LEAGG |
| g816 | 1.10E−12 | 3.16E−11 | 2.00E−08 | K(gEpalm)14, LEAGG, E17 |
| g817 | 1.68E−12 | 2.51E−11 | 1.52E−08 | K(gEpalm)14, LEAGG, A18 |

TABLE 4-continued cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| g876 | 1.04E−11 | 8.63E−11 | 7.90E−08 | K(gEpalm)14, LEAGG, R20 , E24, E12 |
| g805 | 1.44E−12 | 2.28E−11 | 9.97E−08 | K(gEpalm)14, LEAGG, R20 E24 |
| g850 | 2.19E−12 | 2.12E−11 | 8.96E−08 | K(gEpalm)14, LEA, R20, A24, S18 R12 |
| g836 | 1.55E−11 | 1.24E−10 | 1.00E−07 | K(gEpalm)14, LEAGG, R20 E24, E17 |
| g804 | 1.95E−12 | 7.15E−11 | 9.97E−08 | K(gEpalm)14, LEA, R20, A24 |
| g618 | no data | | | K(Ahx-palm)20, LEKGR |
| g781 | 2.86E−12 | 1.04E−10 | 4.02E−07 | K(gEpalm)16, LEAGG, R20 A24 |
| g782 | 1.56E−10 | 2.54E−11 | 1.43E−06 | K(gEpalm)18, LEAGG, R20 A24 |
| g744 | 3.92E−11 | 2.45E−09 | 0.00E+00 | K(gE-palm)20, LEAGG |
| g746 | 3.54E−11 | 1.15E−08 | 0.00E+00 | K(gE-palm)24, LEAGG |
| g747 | 9.42E−11 | 3.16E−09 | 1.04E−06 | K(gE-palm)31, LEAGG |
| g512 | 6.06E−11 | 9.80E−11 | 4.07E−07 | K(gEpalm)17, LEAGG, G2, |
| g513 | 7.23E−10 | 1.75E−10 | 2.98E−07 | K(gEpalm)17, LEAGG, E3, |
| g734 | 8.28E−08 | 6.95E−11 | 1.17E−06 | K(bA-palm)17, LEAGG, R20 A24, E3 E12 |
| g837 | 2.13E−10 | 4.67E−10 | 1.14E−07 | K(gE-palm)17, LEAGG, R20 A24 E12 |
| g838 | 5.68E−12 | 2.37E−11 | 8.43E−08 | K(Ahx-palm)17, LEAGG, R20 A24 E12 |
| g783 | 9.11E−11 | 4.24E−11 | 8.46E−07 | K(bA-palm)17, LEAGG, R20 A24 E12 |
| g851 | no data | | | K(bA-palm)17, LEAGG, R20 A24, R12 acid |
| g852 | no data | | | K(bA-palm)17, LEAGG, R20 A24, R12 Aib2 acid |
| g819 | 2.34E−12 | 1.80E−11 | 1.03E−07 | K(bA-palm)17, LEAGG, R20 A24 |
| g536 | 4.78E−12 | 7.45E−11 | 0.00E+00 | |
| g600 | 5.47E−12 | 6.66E−11 | 1.24E−07 | K(gE-palm)17, LVAGG, E24 |
| g599 | 9.62E−11 | 8.76E−11 | 1.13E−07 | K(gE-palm)17, LVAGG, E20 |

Parent sequence HSQGT5 PTSDY10 SKYLD15 SRRAQ20 DFVQW25 LERGG-amide
Peptides in this section all have the sequence LERGG from residue 26 onwards unless otherwise stated, e.g. LENT

| | hGlucR EC50 M | hGLP1R EC50 M | hGIPR EC50 M | Site and nature of palmitoylation, Substitutions into parent sequence |
|---|---|---|---|---|
| g825 | 3.67E−12 | 1.91E−11 | 8.67E−08 | K(Ahx-palm)17, LENT, R20 E24, E12 |
| g588 | 7.23E−11 | 1.10E−10 | 9.80E−08 | K(gEpalm)17, LERGG, G2, |
| g614 | 3.65E−12 | 9.31E−12 | 9.93E−08 | K(Ahx-palm)17, LERGG, E12 |
| g684 | 1.64E−10 | 1.51E−11 | 1.46E−07 | K(Ahx-palm)17, LERGG, R20 A24 E12 G2 |
| g721 | 3.23E−09 | 4.11E−10 | 9.79E−07 | K(gE-palm)17, LERGG, R20 A24 E12 G2 |
| g724 | 3.09E−08 | 1.90E−11 | 9.33E−07 | K(Ahx-palm)17, LERGG, R20 A24 E12 G2 E3 |
| g772 | 1.84E−10 | 2.92E−10 | 1.54E−06 | K(gE-palm)17, LERGG, R20 A24 E12 |
| g795 | 1.10E−10 | 7.34E−11 | 5.79E−07 | K(bA-palm)17, LERGG, R20 A24 E12 |
| g794 | 4.69E−12 | 1.57E−11 | 3.22E−08 | K(Ahx-palm)17, LERGG, R20 A24 E12 |
| g826 | 4.23E−12 | 2.93E−11 | 5.80E−08 | K(Ahx-palm)17, LERGG, R20 A24 E12 acid |
| g727 | 2.18E−10 | 2.63E−11 | 1.77E−07 | K(Ahx-palm)17, LERGG, R20 A24 E12 G2 acid |
| g683 | 3.72E−10 | 1.59E−11 | 1.26E−07 | K(Ahx-palm)17, LERGG, A20 A24 E12 G2 |
| g722 | 1.11E−08 | 4.26E−10 | 1.67E−06 | K(gE-palm)17, LERGG, A20 A24 E12 G2 |
| g725 | 5.99E−08 | 2.52E−11 | 1.48E−06 | K(Ahx-palm)17, LERGG, A20 A24 E12 G2 E3 |
| g818 | 8.90E−12 | 2.10E−11 | 9.40E−08 | K(Ahx-palm)17, LERGG, A20 A24 E12 |
| g682 | 1.95E−10 | 1.43E−11 | 1.22E−07 | K(Ahx-palm)17, LERGG, R20 E24 E12 G2 |
| g723 | 8.95E−09 | 3.30E−10 | 7.61E−07 | K(gE-palm)17, LERGG, R20 E24 E12 G2 |
| g726 | 1.31E−08 | 7.91E−12 | 2.15E−07 | K(Ahx-palm)17, LERGG, R20 E24 E12 G2 E3 |
| g771 | 5.51E−12 | 1.75E−11 | 3.71E−08 | K(Ahx-palm)17, LERGG, R20 E24 E12 |

TABLE 4-continued cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| g617 | no data | | | K(Ahx-palm)20, LERGG, G2, E12, |
| g787 | 4.36E−11 | 6.65E−09 | 0.00E+00 | K(Ahx-palm)20, LERGG, A24 E17 |
| g806 | 9.9E−12 | 1.71E−10 | 1.05E−07 | K(Ahx-palm)21, LERGG, A18 |
| g616 | no data | | | K(Ahx-palm)24, LERGG, G2, E12 |
| g701 | 3.83E−09 | 7.4E−09 | 0.00E+00 | K(gEpalm)12, LERGG, G2 E17 |
| Parent sequence HSQGT5 FTSDY10 SKYLD15 SRRAQ20 DFVQW25 LVAGG extension Peptides in this section have the residues noted C-terminal to residue 30 and a C-terminal amide | | | | |
| g316 | 1.06E−11 | 3.14E−11 | 3.65E−09 | SSGGSS |
| g317 | 0.00E+00 | 2.63E−09 | 0.00E+00 | SSGGSS K |
| g318 | 9.04E−09 | 1.14E−09 | 0.00E+00 | SSGGSSK(palm) |
| g402 | 5.96E−11 | 8.57E−11 | 0.00E+00 | SGSGSG |
| g319 | 1.04E−11 | 3.61E−11 | 0.00E+00 | PSSGA PPPSK |
| g320 | 3.20E−12 | 9.38E−12 | 1.01E−09 | PSSGA PPPSK(palm) |
| g315 | 5.04E−12 | 2.73E−11 | 1.97E−08 | GGGG |
| g325 | 1.03E−11 | 2.61E−11 | 0.00E+00 | GGGGK |
| g326 | 2.82E−12 | 2.47E−11 | 1.26E−08 | GGGGK(palm) |
| g327 | 2.32E−12 | 1.93E−11 | 1.28E−08 | GGGGK(gEpalm) |
| g321 | 2.79E−11 | 2.72E−11 | 6.41E−09 | KNNRNNIAK |
| g322 | 3.55E−12 | 1.06E−11 | 1.72E−09 | KNNRNNIAK(palm) |

Abbreviations: K(gE-palm) = Lysine with a palmitoyl group conjugated to the epsilon nitrogen, through a gamma glutamic acid linker; K (Ahx-palm) = Lysine with a palmitoyl group conjugated to the epsilon nitrogen, through an aminohexanoic acid linker; K(bA-palm) = Lysine with a palmitoyl group conjugated to the epsilon nitrogen, through a beta alanine acid linker; Aib, aminoisobutyric acid. K(palm) = Lysine with a palmitoyl group directly conjugated to the epsilon nitrogen.

Glucagon and GLP-1 Receptor Mediated cAMP Production Assays in Presence of Plasma Concentrations of Serum Albumin (Assay 2).

Agonist potency determinations for peptides inducing cAMP production were measured in CHO cells expressing human, rat or mouse glucagon receptors (abbreviated to GlucR or GCGR) or GLP-1 receptors in the presence of human, rat or mouse serum albumin at 4.4, 3.2 and 3.2% respectively, as follows.

CHO cells with stable recombinant expression of the human, mouse or rat GlucR or GLP-1 receptor were cultured in DMEM 10% FBS and geneticin (100 µg/ml). Cryopreserved cell stocks were prepared in 1× cell freezing medium-DMSO serum free (Sigma Aldrich) at 2×10$^7$/vial and stored at −80° C. Cells were rapidly thawed at 37° C. and then diluted in to assay buffer (DMEM) containing serum albumin at 4.4, 3.2 and 3.2% for human, rat, and mouse serum albumin respectively. Peptides were serially diluted in DMSO and then diluted 100 fold into DMEM containing serum albumin at stated final concentration. Diluted peptides were then transferred into 384 black shallow well microtitre assay plates. Cells were added to the assay plates and incubated for 30 min at room temperature. Following incubation the assay was stopped and cAMP levels measured using the HTRF® dynamic d2 cAMP assay kit available from CisBio Bioassays, as per the manufacturer's guidelines. Plates were read on Perkin Elmer ENVISION® fluorescence plate readers. Human and rat serum albumin were purchased from Sigma Aldrich and mouse serum albumin from Equitech Bio Ltd.

Data was transformed to % Delta F as described in manufacturer's guidelines and analysed by 4-parameter logistic fit to determine $EC_{50}$ values. Assay 2 EC50 values for selected peptides are shown the Table 5. The assay 2 EC50 values determined are dependent on both the intrinsic potency of the peptides tested at the GLP1 and glucagon receptors in the recombinant cell lines and on the affinity of the peptide for serum albumin, which determines the amount of free peptide. Association with serum albumin increases the EC50 value obtained. The fraction of free peptide at plasma concentrations of albumin and the EC50 at 0% HSA can be calculated based on the variation in cAMP generation with the HSA concentration. For instance, G730 and G933 gave values of 0.85% and 0.29% for free peptide at 4.4% HSA and 7 pM and 6 pM for the EC50 at the GLP1R at 0% HSA respectively. G797 and G849 give values of 0.82% and 0.48% for free peptide at 4.4% HSA and 7 pM and 2 pM for the EC50 at the GLP1R at 0% HSA respectively. To compare the balance of activities at the GLP1R and GlucR between different peptides and across different conditions, these can be correlated using the calculation below, where the EC50's are related to those of the natural ligands.

TABLE 5

EC50 Potencies for GLP-1/Glucagon Agonist Peptides in the
Presence of Plasma Concentrations of Serum Albumin (Assay 2)

| Peptide | Assay in 4.4% Human Serum Albumin | | | Assay in 3.2% Mouse Serum Albumin | | | Assay in 3.2% Rat Serum Albumin | | |
|---|---|---|---|---|---|---|---|---|---|
| | Human GLP1R EC50 pM | Human GlucR EC50 pM | Human GlucR/ GLP1R Ratio[1] | Mouse GLP1R EC50 pM | Mouse GlucR EC50 pM | Mouse GlucR/ GLP1R Ratio[1] | Rat GLP1R EC50 pM | Rat GlucR EC50 pM | Rat GlucR/ GLP1R Ratio[1] |
| G730 | 455 | 402 | 0.122 | 1100 | 5460 | 0.04 | 81 | 45080 | 0.06 |
| G797 | 739 | 1137 | 0.07 | 290 | 764 | 0.08 | 60 | 23170 | 0.08 |
| G849 | 172 | 79 | 0.235 | 88 | 103 | 0.17 | 44 | 4055 | 0.33 |
| G933 | 943 | 564 | 0.179 | 540 | 377 | 0.29 | 136 | 15500 | 0.27 |
| G865 | 150 | 570 | 0.027 | 96 | 1100 | 0.021 | 18 | 87100 | 0.01 |
| G796 | 140 | 53 | 0.275 | 130 | 34 | 0.78 | 23 | 2000 | 0.36 |
| G812 | 316 | 764 | 0.044 | 130 | 947 | 0.032 | 19 | 14100 | 0.04 |
| G380 | 6543 | 53590 | 0.013 | 15000 | 576000 | 0.006 | | | |
| GLP1 | 25 | | | 21 | | | 1.9 | | |
| Glucagon | | 2.7 | | 9700 | 4.97 | | 557 | 60 | |

[1]GlucR/GLP1R ratios were determined as follows:
Relative Potency GlucR = EC50 Glucagon/EC50 Tested peptide
Relative Potency GLP1R = EC50 GLP1/EC50 Tested peptide
GlucR/GLP1R Ratio = Relative Potency GlucR/Relative Potency GLP1R Stability Testing of Peptides in Plasma.

The stability in plasma of the peptides G730, G797, G849 and G933 was determined as follows.

Stock solutions of the peptides of about 200 µmol/L was prepared by weighing solid peptide into a Eppendorf Low Bind Tube and dissolved in DMSO. 10 µL of stock solutions were added to 990 µL of plasma in an Eppendorf Low Bind Tube, resulting in initial concentrations of the peptides in plasma of about 2 µmol/L. The frozen blank plasma from human, rat and mouse had been thawed and heated to a temperature of 37° C. before addition of the stock solution. The spiked plasma samples were gently mixed and allowed to equilibrate for about 5 minutes before start of experiment. The plasma samples were incubated for 48 hours in a GalaxyR $CO_2$ incubator at 37° C. Sampling (30 µL) was performed at 0, 1, 2, 6.5, 17, 24 and 48 hours. The samples were stored at −70° C. until analysis.

Plasma samples were assayed as follows. The 30 µL plasma samples were protein precipitated with 180 ml of cold ethanol in a 96-well low bind plate (Eppendorf Protein LoBind). After mixing and centrifugation, 100 µl the supernatant was transferred to a new plate and 1 µl was injected onto an analytical column.

The analysis was performed using a µLC-system (LC Exigent µLC) coupled to a medium high resolution mass spectrometer (Perkin Elmer PenTOF) with positive electrospray ionisation. The analytical column was a 5 cm, 1 mm Agilent Poroshell (custom made) C18-column with a particle size of 2.7 µm. Flow: 0.1 ml/min using a slow reversed phase gradient. Mobile phases used were acetonitrile and water containing 0.1% formic acid.

The resulting data were manually evaluated for the following degradation products: +1 product (acid) and the DPP IV-cleavage product. Products with +1 mass may arise from deamidation at amide groups of glutamine or at the C-terminus. Cleavage products arise from the action of the protease DPP IV in plasma. Both the degradation of the peptides and formation of peptide products were reported in percentage of the initial peptide concentration. Peaks were integrated and % remaining peptide was calculated: (peak area/peak area 0H)*100. Data for the 24 h time point is shown in Table 6. Levels of deamidation and DPP IV cleavage were low for G797 and G933.

TABLE 6

Peptide Stability in Plasma

| Peptide | Plasma Stability in Mouse Plasma at 24 h | | | Plasma Stability in Human Plasma at 24 h | | | Plasma Stability in Rat Plasma at 24 h | | |
|---|---|---|---|---|---|---|---|---|---|
| | % stable peptide | % +1 prod | % DPP cleaved product/+1 DPP cleaved product | % stable peptide | % +1 prod | % DPP cleaved product/+1 DPP cleaved product | % stable peptide | % +1 prod | % DPP cleaved product/+1 DPP cleaved product |
| G730 | 65 | 15 | 14/5 | 100 | <1 | <1 | 24 | 58 | 2 |
| G797 | 84 | <1 | 1 | 85 | <1 | <1 | 60 | <1 | 1 |
| G849 | 38 | <1 | 22 | 100 | <1 | <1 | 69 | 16 | 3 |
| G933 | 83 | | 1 | 86 | <1 | <1 | 85 | | <1 |

Solubility

Peptide solubility was assessed in a variety of buffer species within a pH range of 4.5 to 8.0, as follows. Dried powder forms of the GLP-1/Glucagon agonist peptides were reconstituted in various buffers at room temperature. The absorbance was measured at 280 nm using NanoDrop 2000 spectrophotometer and the peptide concentration was calculated using the following equation:

$$c=(A_{280}*M_w)/\varepsilon$$

where: c—concentration ε—extinction coefficient Mw—molecular weight $A_{280}$—Absorbance at 280 nm $$\varepsilon=(1\times Trp=5560)+(1\times Tyr=1200)$$

The Results are shown in Table 7. Each of the peptides was soluble at 0.8 mg/ml over a range of pH (6.5 to 8.5). G730 was soluble in a pH range of 4.5 to 8.0, G797 was soluble in a pH range of 6. to 8.0, and G933 was soluble in a pH range of 6 to 8.0. The solubility of G933 was tested in a number of different buffer systems, also shown in Table 7. G933 was soluble at 1 mg/ml in at least the following buffer systems: histidine (pH 6 and 7; ionic strength: 0.25 to 100 mM), sodium phosphate (pH 6-7.5; ionic strength: 0.25 to 100 mM), and tris/hydroxymethyl aminomethane (pH 7-9; ionic strength: 0.25 to 100 mM).

TABLE 7

Peptide solubility profile (Ionic Strength of all buffers: 100 mM)

| Buffer | Conc. (mg/ml) A280 Target 1 mg/ml | | | |
|---|---|---|---|---|
| | G730 | G797 | G849 | G933 |
| Glutamate pH 4.5 | 0.83 | 0.023 | NA | 0.02 |
| Acetate pH 5 | NA | NA | NA | 0.03 |
| Succinate pH 5 | NA | NA | NA | 1.1 |
| Phosphate, pH = 6 | 0.14 | 0.84 | 0.06 | 1.2 |
| Histidine pH 6 | NA | NA | NA | 1.2 |
| Phosphate pH 6.5 | 0.83 | 0.84 | NA | NA |
| Phosphate, pH 7.0 | NA | NA | NA | 1.1 |
| Histidine, pH 7.0 | NA | NA | NA | 1.1 |
| Phosphate pH 7.5 | 0.85 | 0.86 | NA | 1.2 |
| Tris pH 7.5 | 0.83 | 0.89 | 0.89 | 1.2 |
| Tris pH 8.0 | 1.1 | 0.83 | 0.89 | 1.2 |

Formulations.

Peptide solubility was assessed in three different isotonic formulations:
1. Default Formulation (DF)=0.1M Tris pH 7.5, 150 mM Mannitol. Final formulation pH=7.2
2. Back up formulation 1 (BF1)=0.05M Tris, 50 mM Arginine/Proline. Final formulation pH=8.0
3. Back up formulation 2 (BF2)=Sodium Phosphate buffer (pH8)/1.85% W/V propylene glycol. Final formulation pH=7.0

Solubility was measured as detailed above, and the results are shown in Table 8. G730, G797 and G933 were soluble to at least 5 mg/ml in the DF, the maximum solubility of G849 in DF was 3.7 mg/ml, G797 was soluble to at least 10 mg/ml in BF1, and G933 was soluble to at least 10 mg/ml in BF2.

TABLE 8

Peptide Solubility in Formulation

| Lead Candidate | Formulation Concentration | Formulation | 10 mg/ml solubility (BF2) |
|---|---|---|---|
| G730 | 5 mg/ml | DF | no |
| G797 | 5 mg/ml | DF/BF1 | yes |
| G849 | 3.7 mg/ml | DF | n/a |
| G933 | 5 mg/ml | DF | yes |

Concentration Determined by A280 nm

The stability of the DF was evaluated by measuring purity reversed phase ultra-performance liquid chromatography (RP UPLC), within one month. The storage conditions were 5° C., 25° C., 40° C. and −80° C. The results are shown in Tables 9 and 10.

TABLE 9

Peptide formulation purity after 1 month in stability conditions

| Peptide | 5° C. | 25° C. | 40° C. | minus 80 C. |
|---|---|---|---|---|
| G730_DF | 97.7 | 96.1 | 86.1 | 97.7 |
| G797_BF1 | 98.72 | 98.84 | 77.54 | NA |
| G849_DF | 95.5 | NA | NA | NA |
| G933_DF | 97.8 | 95.9 | 88.9 | 98.9 |

TABLE 10

Peptide formulation purity loss (% compared to T0) after 1 month in stability conditions

| Lead Candidate | 5° C. | 25° C. | 40° C. | minus 80 C. |
|---|---|---|---|---|
| G730_DF | 0.82 | 2.43 | 12.54 | 0.3 |
| G797_BF1 | 0.24 | 0.12 | 21.65 | 0.3 |
| G849_DF | n/a | n/a | n/a | n/a |
| G933_DF | 0.3 | 2.2 | 9.3 | (−)0.8 |

The peptides all showed acceptable properties with respect to solubility, formulatability and stability Example 3: In Vivo Studies G730, G797, and G812 (Study A).

Selected GLP-1/glucagon agonist peptides disclosed herein were tested in a diet induced obesity (DIO) mouse model, as follows. Female C57/Blb6JHsdOla (obtained from Harlan Laboratories, UK) were started on a high fat diet of D12492 (Research Diets, NJ, USA) and a chocolate confection, delicato ball (Delicata Bakverk, Sweden) at 9-11 weeks of age, and were maintained on the diet for 16 weeks prior to arrival to the animal facility, during a three week acclimation period and during drug treatment, caloric content of the two components of the diet is shown in Table 11. The mice were divided into 9 groups (n=5-6), and treatment was started at 29 weeks of age. The treatment groups and dosing are shown in Table 12.

TABLE 11

Content of DIO Diet

| Product | Protein (%) | Carbohydrate (%) | Fat (%) | Kcal fat (%) | Total Kcal/gram |
|---|---|---|---|---|---|
| Delicatoball (Delicata Bakverk AB, Huddinge, Sweden) | 5 | 53 | 31 | 54 | 5.05 |
| D12492 (research Diets, NJ, USA) | 26.2 | 26.3 | 34.9 | 60 | 5.24 |

TABLE 12

Treatment Groups for Study A

| Peptide | Dose | # of Animals |
|---|---|---|
| Vehicle | NA | 6 |
| Liraglutide | 26.6 nmol/kg | 6 |
| G730 | 10 nmol/kg | 6 |
| G730 | 20 nmol/kg | 5 |

TABLE 12-continued

Treatment Groups for Study A

| Peptide | Dose | # of Animals |
|---|---|---|
| G730 | 50 nmol/kg | 6 |
| G797 | 5 nmol/kg | 5 |
| G797 | 20 nmol/kg | 6 |
| G797 | 50 nmol/kg | 6 |
| G812 | 20 nmol/kg | 5 |

GLP-1/glucagon agonist peptides G730, G797, and G812, as well as Liraglutide were formulated in the vehicle, 100 mM Tris/150 mM mannitol, pH 7.4 The treatments were administered subcutaneously twice daily for 14 days, whilst the animals were maintained on a high fat diet. The body weight of the animals was monitored daily throughout the dosing period. At day 14, blood samples for the measurement of plasma glucose and insulin from conscious mice were obtained after a 4-hour fasting period. Mice were then anaesthetized using isoflourane and terminal blood was collected from the capillary bed behind the eye. The following parameters were measured: blood chemistry measurements of triglycerides, total cholesterol, non-esterified fatty acids (NEFA), beta-hydroxybutyrate and fibroblast growth factor 21 (FGF21) (Tables 14 and 15 below).

The effect of treatment with liraglutide and the GLP-1/glucagon agonist peptides G730, G797 and G812 on body weight, in comparison to liraglutide and vehicle, is shown in FIGS. 1-4. Animals treated with either G730 or G797 showed dose dependent and continuous weight loss over the 14 day dosing period. At 50 nmol/kg, animals treated with G730 and G797 experienced an about 24% change in weight at day 14 as compared to the vehicle-treated animals.

Mice treated with G730 or G797 showed a dose-dependent reduction in glucose levels at day 14 (Table 13). Reduced insulin levels were also observed, with these two treatments, especially at the higher doses (Table 13). The insulin sensitivity index Homeostatic model assessment (HOMA) significantly improved at 20 nmol/kg G730 and 20 and 50 nmol/kg G797. HOMA is a modeling method that uses the sum of plasma insulin and glucose levels to assess β-cell function and insulin resistance (Table 14). Total plasma cholesterol was lowered both by liraglutide, G730 and G797 at all doses, with less pronounced changes in plasma non-esterified fatty acids (NEFA) levels and plasma and hepatic triglycerides (TG). Beta-hydroxybutyrate (BeHy) had tendencies towards increased levels, in line with the body weight loss. Fibroblast growth factor 21 (FGF21) generally increased with dual GLP-1/glucagon agonist peptide treatment.

TABLE 13

Effect of GLP-1/glucagon agonist peptide treatment on glucose, insulin, and HOMA

| Peptide | dose (nmol/kg) | start bw (g) | ± SEM | BW day 14 (% change of vehicle mean) | ± SEM | Glucose (mM) | ± SEM | Insulin (nM) | ± SEM | HOMA | ± SEM |
|---|---|---|---|---|---|---|---|---|---|---|---|
| vehicle | 0 | 47.4 | ± 3.7 | 0.0 | ± 0 | 8.8 | ± 0.6 | 0.8 | ± 0.23 | 7.2 | ± 2.0 |
| Liraglutide | 27 | 47.5 | ± 1.8 | −13.3 | ± 1.4 | 8.0 | ± 0.2 | 0.3 | ± 0.12 | 2.8 | ± 1.1 |
| G730 | 10 | 44.5 | ± 2.2 | −7.5 | ± 1.1 | 7.2 | ± 0.3 * | 0.4 | ± 0.14 | 3.3 | ± 1.1 |
| G730 | 20 | 45.9 | ± 3.6 | −15.6 | ± 2.2 | 6.7 | ± 0.6 * | 0.2 | ± 0.06 | 1.7 | ± 0.5 * |
| G730 | 50 | 46.1 | ± 2.4 | −24.0 | ± 5.1 | 5.9 | ± 0.7 * | 0.3 | ± 0.13 | 2.1 | ± 1.0 |
| G797 | 5 | 47.5 | ± 1.2 | −5.7 | ± 3.2 | 7.5 | ± 0.3 | 0.7 | ± 0.25 | 5.3 | ± 2.0 |
| G797 | 20 | 47.4 | ± 2.2 | −16.0 | ± 4.4 | 7.1 | ± 0.6 | 0.3 | ± 0.09 | 2.0 | ± 0.8 * |
| G797 | 50 | 47.2 | ± 1.8 | −25.4 | ± 2.0 | 6.6 | ± 0.5 * | 0.1 | ± 0.01 * | 0.6 | 0.1 * |
| G812 | 20 | 49.2 | ± 3.4 | −8.7 | ± 1.4 | 8.0 | ± 0.4 | 0.7 | ± 0.23 | 6.0 | ± 2.1 |

Results evaluated by a two-tailed distribution, two-sample unequal variance ttest;
* indicates $p < 0.05$ compared to vehicle.

TABLE 14

Effect of GLP-1/glucagon agonist peptide treatment on additional blood chemistry measurements

| Peptide | dose (nmol/kg) | Hepatic TG (g Tg/100 g tissue) | ± SEM | Plasma Tg (mM) | ± SEM | Plasma NEFA mM) | ± SEM |
|---|---|---|---|---|---|---|---|
| vehicle | 0 | 13.6 | ± 0.5 | 0.19 | ± 0.02 | 0.22 | ± 0.0 |
| Liraglutide | 27 | 13.1 | ± 2.1 | 0.24 | ± 0.01 | 0.24 | ± 0.01 |
| G730 | 10 | 9.0 | ± 0.9 * | 0.21 | ± 0.02 | 0.29 | ± 0.02 |
| G730 | 20 | 17.7 | ± 9.4 | 0.26 | ± 0.03 | 0.25 | ± 0.03 |
| G730 | 50 | 28.1 | ± 1.1 | 0.23 | ± 0.03 | 0.32 | ± 0.05 |
| G797 | 5 | 13.0 | ± 1.1 | 0.15 | ± 0.02 | 0.24 | ± 0.03 |
| G797 | 20 | 17.7 | ± 5.7 | 0.14 | ± 0.02 | 0.27 | ± 0.05 |
| G797 | 50 | 15.5 | ± 5.9 | 0.12 | ± 0.02 * | 0.24 | ± 0.02 |
| G812 | 20 | 7.9 | ± 6.5 * | 0.13 | ± 0.01 * | 0.21 | ± 0.01 |

| Peptide | Plasma Cholesterol (mM) | SEM | BeHy (umol/l) | SEM | FGF21 (pg/mL) | SEM |
|---|---|---|---|---|---|---|
| vehicle | 4.65 | ± 0.12 | 389 | ± 46 | 2757 | ± 317 |
| Liraglutide | 3.75 | ± 0.15 * | 345 | ± 21 | 2491 | ± 650 |

TABLE 14-continued

Effect of GLP-1/glucagon agonist peptide treatment on additional blood chemistry measurements

| G730 | * | 3.10 | ± | 0.15 | * | 428  | ± | 54  | 1953 | ± | 219  |   |
|------|---|------|---|------|---|------|---|-----|------|---|------|---|
| G730 |   | 2.45 | ± | 0.03 | * | 756  | ± | 318 | 2235 | ± | 300  |   |
| G730 |   | 2.19 | ± | 0.23 | * | 1477 | ± | 479 | 5294 | ± | 2307 |   |
| G797 |   | 3.32 | ± | 0.38 | * | 392  | ± | 111 | 2352 | ± | 342  |   |
| G797 |   | 2.44 | ± | 0.27 | * | 559  | ± | 240 | 7277 | ± | 2455 |   |
| G797 |   | 1.95 | ± | 0.07 | * | 1257 | ± | 285 | 5373 | ± | 813  | * |
| G812 |   | 2.79 | ± | 0.24 | * | 333  | ± | 63  | 3207 | ± | 388  |   |

Results evaluated by a two-tailed distribution, two-sample unequal variance t test;
* indicates p < 0.05 compared to vehicle.

G865, G933, and G796 (Study B).

A further set of GLP-1/glucagon peptides was tested in a diet induced obesity model using the same protocol above, but with the treatment groups and dosing shown in Table 15:

TABLE 15

Treatment Groups for Study B

| Peptide | Dose | # of Animals |
|---------|------|--------------|
| Vehicle | NA | 6 |
| Liraglutide | 26.6 nmol/kg | 6 |
| G865 | 5 nmol/kg | 6 |
| G865 | 10 nmol/kg | 6 |
| G933 | 5 nmol/kg | 6 |
| G933 | 10 nmol/kg | 6 |
| G796 | 20 nmol/kg | 6 |
| G796 | 50 nmol/kg | 6 |

GLP-1/glucagon agonist peptides G865, G933, and G796, as well as liraglutide were formulated in the vehicle, 100 mM Tris/150 mM mannitol, pH 7.4 The treatments were administered subcutaneously twice daily for 14 days, whilst the animals were maintained on a high fat diet. The body weight of the animals was monitored daily throughout the dosing period. At day 14, blood samples for the measurement of plasma glucose and insulin from conscious mice were obtained after a 4-hour fasting period. Mice were then anaesthetized using isoflourane and terminal blood was collected from the capillary bed behind the eye. The following parameters were measured: blood chemistry measurements of triglycerides, total cholesterol, non-esterified fatty acids (NEFA), beta-hydroxybutyrate and fibroblast growth factor 21 (FGF21) (Table 16 and Table 17 below).

The effect of treatment with liraglutide and the GLP-1/glucagon agonist peptides G933, G865, G796 on body weight, in comparison to liraglutide and vehicle, is shown in FIGS. 5-8. Animals treated with either G933, G865 or G796 showed dose dependent and continuous weight loss over the 14 day dosing period.

Glucose levels, insulin levels and HOMA at day 14 post-treatment are shown in Table 16. Total plasma cholesterol levels, plasma non-esterified fatty acids (NEFA) levels, plasma and hepatic triglyceride (TG) levels, beta-hydroxy butyrate (BeHy) levels, and fibroblast growth factor 21 (FGF21) levels at day 14 post-treatment are shown in Table 17.

TABLE 16

Effect of GLP-1/glucagon agonist peptide treatment on glucose, insulin, and HOMA

| Peptide | dose (nmol/kg) | start bw (g) | | SEM | BW day 14 (% change of vehicle mean) | | SEM | Glucose (mM) | | SEM | Insulin (nM) | | SEM | HOMA | | SEM | |
|---------|---------------|--------------|---|-----|--------------------------------------|---|-----|--------------|---|-----|--------------|---|-----|------|---|-----|---|
| vehicle | 0 | 46.9 | ± | 1 | 0 | ± | 0 | 8.7 | ± | 0.8 | 0.58 | ± | 0.09 | 5.05 | ± | 0.8 | |
| Liraglutide | 27 | 46.3 | ± | 1.7 | −14 | ± | 2.1 | 7.7 | ± | 0.7 | 0.31 | ± | 0.07 | * | 2.51 | ± | 0.7 | * |
| G865 | 5 | 46.9 | ± | 0.8 | −4 | ± | 0.1 | 6.2 | ± | 0.6 | * | 0.33 | ± | 0.08 | 2.14 | ± | 0.6 | * |
| G865 | 10 | 47.0 | ± | 0.9 | −14 | ± | 3.4 | 6.6 | ± | 0.5 | * | 0.36 | ± | 0.06 | 2.43 | ± | 0.5 | * |
| G933 | 5 | 48.1 | ± | 1.6 | −11 | ± | 2.7 | 6.2 | ± | 0.8 | * | 0.53 | ± | 0.13 | 3.31 | ± | 0.8 | |
| G933 | 10 | 48.6 | ± | 0.5 | −19 | ± | 3.5 | 7.2 | ± | 0.6 | * | 0.27 | ± | 0.07 | * | 1.98 | ± | 0.6 | * |
| G796 | 20 | 50.9 | ± | 1.3 | −16 | ± | 0.6 | 6.1 | ± | 0.2 | * | 0.38 | ± | 0.05 | 2.24 | ± | 0.2 | * |
| G796 | 50 | 49.7 | ± | 0.8 | −23 | ± | 1.6 | 6.4 | ± | 1.1 | * | 0.43 | ± | 0.14 | 2.87 | ± | 1.1 | |

Results evaluated by a two-tailed distribution, two-sample unequal variance t test;
* indicates p < 0.05 compared to vehicle.

TABLE 17

Effect of GLP-1/glucagon agonist peptide treatment on additional blood chemistry measurements

| Peptide | dose (nmol/kg) | Hepatic TG (g TG/100 g tissue) | | SEM | Plasma TG (mM) | | SEM | Plasma NEFA (mM) | | SEM | |
|---------|----------------|--------------------------------|---|-----|----------------|---|-----|-------------------|---|-----|---|
| vehicle | 0 | 17.53 | ± | 1.30 | 0.25 | ± | 0.01 | 0.28 | ± | 0.03 | |
| Liraglutide | 27 | 18.4 | ± | 2.5 | 0.28 | ± | 0.03 | * | 0.29 | ± | 0.02 |
| G865 | 5 | 20.7 | ± | 5.6 | 0.26 | ± | 0.03 | 0.29 | ± | 0.05 | |

TABLE 17-continued

Effect of GLP-1/glucagon agonist peptide treatment on additional blood chemistry measurements

| | | | | | | | | | | |
|---|---|---|---|---|---|---|---|---|---|---|
| G865 | 10 | 22.3 | ± | 5.1 | 0.23 | ± | 0.02 | 0.27 | ± | 0.03 |
| G933 | 5 | 11.3 | ± | 0.8 * | 0.19 | ± | 0.01 * | 0.28 | ± | 0.03 |
| G933 | 10 | 14.7 | ± | 4.1 | 0.16 | ± | 0.01 * | 0.27 | ± | 0.03 |
| G796 | 20 | 9.6 | ± | 0.9 * | 0.26 | ± | 0.05 | 0.24 | ± | 0.02 |
| G796 | 50 | 9.9 | ± | 0.6 * | 0.16 | ± | 0.01 * | 0.21 | ± | 0.02 |

| Peptide | Plasma Cholesterol (mM) | | SEM | BeHy (umol/l) | | SEM | FGF21 (pg/mL) | | SEM |
|---|---|---|---|---|---|---|---|---|---|
| vehicle | 4.56 | ± | 0.33 | 387.52 | ± | 87.4 | 2002 | ± | 174 |
| Liraglutide | 3.26 | ± | 0.23 * | 572.25 | ± | 82.4 * | 2990 | ± | 729 |
| G865 | 3.06 | ± | 0.14 * | 775.06 | ± | 295.5 * | 8151 | ± | 4788 |
| G865 | 2.89 | ± | 0.24 * | 567.46 | ± | 169.3 * | 5953 | ± | 3409 |
| G933 | 2.88 | ± | 0.28 * | 673.08 | ± | 117.2 | 2682 | ± | 248 |
| G933 | 2.32 | ± | 0.20 * | 693.56 | ± | 158.3 * | 4459 | ± | 1249 |
| G796 * | 2.11 | ± | 0.07 * | 360.49 | ± | 51.1 | 6441 | ± | 1784 |
| G796 | 1.91 | ± | 0.05 * | 451.80 | ± | 63.4 | 9830 | ± | 3278 |

Results evaluated by a two-tailed distribution, two-sample unequal variance t test;
* indicates p < 0.05 compared to vehicle.

Example 4: Single-Ascending-Dose Study (A) Subjects

A total of 362 subjects consented to participate in the study in Germany. The subjects were screened for the following inclusion and exclusion criteria.

Inclusion Criteria:
Healthy volunteers, ages 18 through 45 years at the time of screening;
Body mass index ≥22 and ≤30 kg/m² and body weight ≥70 kg; and
Venous access suitable for multiple cannulations.

Exclusion Criteria:
Any condition that would interfere with evaluation of the G933 or interpretation of subject safety or study results. Specific examples included (a) past history of acute or chronic pancreatitis, or pancreatic amylase or lipase greater than the upper limit of normal (ULN) at screening, (b) past history of gastroparesis requiring treatment, (c) past history of surgery affecting the upper gastrointestinal tract likely to affect the interpretation of safety and tolerability data, (d) history of cholelithiasis leading to episodes of acute cholecystitis not treated by cholecystectomy, or known biliary disease, (e) history of or family history of multiple endocrine neoplasia type 2 (MEN-2), serum calcitonin suggestive of thyroid C-cell hyperplasia (calcitonin level >50 μg/L), or medullary thyroid carcinoma at screening, (f) past history of clinically significant cardiac rhythm disturbance, e.g., permanent or paroxysmal atrial fibrillation/flutter, paroxysmal supraventricular tachycardia, paroxysmal ventricular tachycardia, presence of an implantable pacemaker device or cardioverter/defibrillator, (g) history of treated or symptomatic cardiac failure, and (h) history of previous myocardial infarction or cerebrovascular accident (e.g., stroke);

History or presence of gastrointestinal, renal, or hepatic disease (with the exception of Gilbert's syndrome) or any other condition known to interfere with absorption, distribution, metabolism, or excretion of drugs;

History of cancer, with the exception of non-melanoma skin cancer;

Any clinically important illness, medical/surgical procedure, or trauma within 4 weeks prior to Day 1 dosing;

Positive hepatitis B surface antigen or hepatitis C virus antibody serology at screening;

Positive human immunodeficiency virus (HIV) test at screening or use of antiretroviral medications as determined by medical history or subject's verbal report;

Serum potassium or calcium outside the normal range at screening;

Serum creatinine, aspartate aminotransferase (AST), alanine aminotransferase (ALT), or total bilirubin greater than the ULN at screening;

Any other clinically important abnormalities in clinical chemistry, hematology, or urinalysis results, as judged by the investigator, should also result in exclusion from the study;

Use of any of the following medicinal products: (a) concurrent or previous use of a GLP-1 receptor agonist, (b) current or previous use of systemic corticosteroids within the past 28 days prior to screening, or (c) use of any medicinal products or herbal preparations licensed for control of body weight or appetite is prohibited from 1 week prior to Day −1 through Day 7;

Abnormal vital signs after 10 minutes of supine rest, defined as any of the following: (a) Systolic blood pressure <90 mmHg or ≥140 mmHg, (b) Diastolic blood pressure <50 mmHg or ≥90 mmHg, or (c) Heart rate <50 or >90 beats per minute;

Any clinically important abnormalities in rhythm, conduction (e.g., Wolff-Parkinson-White syndrome, sick-sinus syndrome), or morphology of the resting 12-lead ECG, or any abnormalities in the ECG that, in the opinion of the investigator, may interfere with the interpretation of changes in the QT interval corrected for heart rate (QTc), including abnormal T-wave morphology, or left ventricular hypertrophy;

Prolonged QTc using the Fridericia formula (QTcF)>450 milliseconds, or shortened QTcF<340 milliseconds based on 12-lead ECG, or family history of long QT syndrome;

PR (PQ) interval shortening to <120 milliseconds or prolongation >200 milliseconds (first degree atrioventricular block);

Intermittent second degree block (Wenckebach block while asleep is not exclusive) or third degree block, or atrioventricular dissociation;

QRS interval outside the range of 50-110 milliseconds;
Known or suspected history of drug abuse within the past 3 years;
History of alcohol abuse or excessive intake of alcohol within the past 3 years;
Current smoker (>0 cigarettes per day); subjects are also excluded if they test positive for cotinine at screening;
Positive screen for drugs of abuse at screening or admission to the study unit, or positive breath test for alcohol on admission to the study unit prior to the administration of investigational product. Subjects who utilize benzodiazepines for chronic anxiety or sleep disorders may be permitted to enter the study;
History of severe allergy/hypersensitivity or ongoing clinically important allergy/hypersensitivity;
Whole blood or red blood cell donation, or any blood loss >500 mL within 2 months prior to screening;
Receipt of another new chemical entity (defined as a compound that has not been approved for marketing), or participation in any other clinical study that included drug treatment within at least 30 days or 5 half-lives of the administration of investigational product in this study (whichever is longer). The period of exclusion to begin 30 days or 5 half-lives of investigational product after the final dose, or after the last visit, whichever is longest. Subjects consented and screened, but not randomized into this study or a previous study, are not excluded; or
Psychiatric illness such that subjects have been committed to an institution by way of official or judicial order After screening, 313 subjects were determined not to meet the inclusion/exclusion criteria. The remaining 48 subjects were randomized and received G933. The demographics of the 48 treated patients are shown in the table below.

TABLE 18

Demographics, As-treated Population

| Parameter | Placebo N = 12 | G933 5 µg N = 6 | G933 10 µg N = 6 | G933 30 µg N = 6 | G933 100 µg N = 6 | G933 150 µg N = 6 | G933 300 µg N = 6 | Total N = 36 | Total N = 48 |
|---|---|---|---|---|---|---|---|---|---|
| Age (years) | | | | | | | | | |
| Mean | 32.8 | 37.3 | 31.8 | 33.2 | 27.8 | 34.5 | 28.3 | 36 | 32.3 |
| SD | 9.1 | 6.4 | 6.8 | 10.4 | 4.3 | 6.5 | 5.9 | 26.12 | 7.7 |
| Median | 29.0 | 37.0 | 34.0 | 32.5 | 28.5 | 33.0 | 26.5 | 2.29 | 31.0 |
| Min, Max | 22, 45 | 28, 45 | 22, 39 | 20, 45 | 20, 32 | 27, 44 | 21, 38 | 25.79 | 20, 45 |
| Gender | | | | | | | | | |
| Male | 12 (100%) | 6 (100%) | 6 (100%) | 6 (100%) | 6 (100%) | 6 (100%) | 6 (100%) | 36 (100%) | 48 (100%) |
| Race[a] | | | | | | | | | |
| American Indian or Alaskan Native | 0 | 0 | 0 | 0 | 0 | 1 (16.7%) | 0 | 1 (2.8%) | 1 (2.1%) |
| Asian | 1 (8.3%) | 0 | 0 | 0 | 0 | 0 | 0 | 0 | 1 (2.1%) |
| White | 11 (91.7%) | 6 (100%) | 5 (83.3%) | 6 (100%) | 6 (100%) | 5 (83.3%) | 6 (100%) | 34 (94.4%) | 45 (93.8%) |
| Other | 0 | 0 | 1 (16.7%) | 0 | 0 | 0 | 0 | 1 (2.8%) | 1 (2.1%) |
| Ethnicity | | | | | | | | | |
| Hispanic or Latino | 0 | 0 | 0 | 0 | 0 | 1 (16.7%) | 1 (16.7%) | 2 (5.6%) | 2 (4.2%) |
| Not Hispanic or Latino | 12 (100%) | 6 (100%) | 6 (100%) | 6 (100%) | 6 (100%) | 5 (83.3%) | 5 (83.3%) | 34 (94.4%) | 46 (95.8%) |
| Weight (kg) | | | | | | | | | |
| Mean | 84.71 | 88.82 | 81.82 | 81.22 | 84.93 | 83.68 | 91.03 | 85.25 | 85.11 |
| SD | 12.10 | 10.48 | 7.66 | 7.28 | 8.23 | 12.90 | 11.07 | 9.79 | 10.28 |
| Median | 78.30 | 88.15 | 80.80 | 78.95 | 83.80 | 77.85 | 94.65 | 83.60 | 81.90 |
| Min, Max | 73.8, 108.1 | 77.2, 107.5 | 72.8, 90.5 | 74.2, 90.6 | 75.9, 95.9 | 71.2, 101.0 | 74.3, 101.0 | 71.2, 107.5 | 71.2, 108.1 |
| Height (cm) | | | | | | | | | |
| Mean | 181.28 | 179.17 | 182.83 | 181.17 | 180.30 | 177.67 | 182.00 | 180.52 | 180.71 |
| SD | 5.33 | 5.31 | 8.57 | 4.45 | 6.71 | 6.38 | 3.41 | 5.86 | 5.69 |
| Median | 180.00 | 177.00 | 179.00 | 181.50 | 180.00 | 175.00 | 182.00 | 179.50 | 180.00 |
| Min, Max | 174.0, 191.0 | 174.0, 188.0 | 176.0, 198.0 | 174.0, 186.0 | 171.0, 190.0 | 170.0, 186.0 | 177.0, 187.0 | 170.0, 198.0 | 170.0, 198.0 |
| BMI (kg/m$^2$) | | | | | | | | | |
| Mean | 25.67 | 27.61 | 24.47 | 24.74 | 26.09 | 26.36 | 27.44 | 26.12 | 26.01 |
| SD | 2.41 | 2.25 | 1.64 | 1.91 | 1.55 | 2.16 | 2.82 | 2.29 | 2.30 |
| Median | 25.27 | 27.39 | 24.24 | 24.51 | 26.19 | 25.42 | 28.64 | 25.79 | 25.79 |
| Min, Max | 22.3, 29.9 | 24.4, 30.4 | 22.7, 27.1 | 22.2, 27.5 | 23.7, 28.0 | 24.6, 29.5 | 22.4, 29.8 | 22.2, 30.4 | 22.2, 30.4 |

BMI = Body mass index;
Max = maximum;
Min = minimum;
N = number of subjects;
SD = standard deviation
[a]Each race category counts subjects who selected only one category (B) Study Design A Phase 1, randomized, blinded, single-ascending dose study was performed. A flow diagram of the proposed study is provided in FIG. 9. Eight subjects per cohort were planned. Within each cohort, the subjects were randomized 3:1 to G933 (MEDI0382) or placebo.

Based on PK/PD modeling conducted using clinical literature data on GPL-1 and glucagon modulators, the clinically efficacious dose of G933 was predicted to be in the range of 300 to 2000 μg/day. Thus, the dose increments of 5, 10, 30, 100, 300, 600, 1200, and 2000 μg G933 were selected. Safety data for each cohort was evaluated before dose escalation was allowed to proceed. To further enhance safety, the fold increases were greatest at the lower end of the proposed dose range and were reduced in a step-wise fashion so that the last dose increase was less than 2-fold. The maximum proposed dose level in this study was 2000 μg. The safety margin at the maximum proposed human dose of 2000 μg based on monkey AUC data was 0.8.

Subjects received 1 dose of G933 during the study. For all subjects, a screening visit was performed within 28 days prior to randomization (Day −29 to Day −2). Subjects were admitted to the unit on the evening prior to receiving investigational product (Day −1) to allow for repeat assessment of eligibility criteria, to perform cardiac telemetry monitoring over a 4-hour period, and to standardize the level of physical activity before dosing the following morning. On Day 1, following an overnight fast for a minimum of 8 hours, baseline safety assessments and blood samples were obtained, and the subject was administered a single subcutaneous (SC) dose of either G933 or placebo. Subjects remained in the study facility for timed assessments and safety monitoring (including cardiac monitoring by continuous telemetry and intermittent digital electrocardiograms [ECG]) throughout Day 1 and Day 2, and remained housed until discharge. Subjects were discharged from the unit on the morning of Day 3 after safety assessments were performed and blood samples collected. Subjects returned to the unit for outpatient visits on Days 4, 7, and 28.

Following screening, the study duration for each subject was approximately 29 days, which included an inpatient evaluation period and an outpatient follow-up period.

For pharmacodynamics evaluations, on Day 1, blood samples for measurement of glucose and insulin levels were drawn before each meal (breakfast, lunch, and evening meal) and 1 and 2 hours (±15 minutes) after the start of each meal. The start of each meal on Day 1 was recorded and each meal was to be consumed within 30 minutes.

For immunological evaluations, anti-drug antibody (ADA) sampling occurred on Day 1, approximately 1 week post-dose, and approximately 1 month post-dose. \

For pharmacokinetic (PK) evaluations, sampling times were pre-dose, and 1, 2, 4, 6, 8, 10, 12, 16, 24, 36, 48, and 72 hours post-dose (±15 minutes for the first 2 hours and ±30 minutes for the remaining time points through 48 hours post-dose). On Day 1, PK samples were also to be drawn before each meal (breakfast, lunch, and evening meal), 1 and 2 hours (±15 minutes) after the start of each meal.

(C) Results

Dose escalation proceeded from 5 to 300 μg as planned per the protocol; however, 300 μg was not tolerated as evidenced by events of significant vomiting, and the dose was de-escalated to 150 μg for the final cohort. A flow diagram of the actual study is provided in FIG. 9, and the subject disposition is shown in FIG. 10.

No PK parameters could be derived for 5 μg G933 as only 3 subjects showed at least one quantifiable level in plasma. Plasma concentrations of G933 were measurable from 2-4.5 hours until 16-24 hours in all subjects in the 5 and 10 μg G933 groups. Plasma concentrations of G933 were measurable until 48 hours in all subjects in the 100 and 300 μg G933 groups. No subject had quantifiable plasma concentrations of G933 at 72 hours post-dose.

The mean concentration-time profiles for all G933 doses displayed an apparent mono-exponential decline following the peak, with a moderately rapid drop of concentration between the peak and 48 hours after dosing.

Single dose plasma G933 PK parameter estimates were listed by subject and treatment and are summarized by treatment in Table 19.

TABLE 19

Summary of Single Dose G933 median Pharmacokinetic Parameter Estimate (Geometric Mean [95% CI])

| Parameters | Dose (μg) | | | | | |
| --- | --- | --- | --- | --- | --- | --- |
| | 5 | 10 | 30 | 100 | 150 | 300 |
| Cmax (ng/mL)$^a$ | 0.47 [0.44-0.50] N = 3 | 0.80 [0.62-1.03] N = 6 | 3.00 [2.59-3.47] N = 6 | 6.19 [4.29-8.92] N = 6 | 8.97 [6.20-12.97] N = 6 | 20.98 [16.21-27.14] N = 6 |
| Tmax (hr)$^b$ | 7.00 [5.88-10.00] N = 3 | 6.94 [4.00-13.50] N = 6 | 9.00 [4.50-10.02] N = 6 | 7.53 [4.50-10.00] N = 6 | 9.00 [4.00-12.00] N = 6 | 4.50 [4.00-5.88] N = 6 |
| t1/2 (hr)$^a$ | nc | nc | 11.43 [8.42-15.50] N = 4 | 12.07 [9.58-15.20] N = 6 | 10.97 [8.60-13.99] N = 6 | 9.54 [8.63-10.56] N = 6 |
| AUC(0-last) (ng · hr/mL)$^a$ | 1.96 [0.58-6.64] N = 3 | 9.97 [7.01-14.17] N = 6 | 51.99 [44.55-60.67] N = 6 | 137.33 [106.15-177.67] N = 6 | 194.60 [162.84-232.56] N = 6 | 364.47 [298.50-445.02] N = 6 |
| AUC(0-∞) (ng · hr/mL)$^a$ | nc | nc | 63.10 [51.49-77.33] N = 4 | 150.03 [118.44-190.04] N = 6 | 209.03 [178.45-244.86] N = 6 | 379.12 [310.26-463.25] N = 6 |
| % extrap AUC(0-∞) (ng · hr/mL)$^c$ | nc | nc | 13.97 [7.22-20.73] N = 4 | 8.35 [3.21-13.48] N = 6 | 6.80 [1.92-11.69] N = 6 | 3.86 [2.64-5.07] N = 6 |
| CL/f | nc | nc | 0.48 | 0.67 | 0.72 | 0.79 |

TABLE 19-continued

Summary of Single Dose G933 median Pharmacokinetic
Parameter Estimate (Geometric Mean [95% CI])

| Parameters | Dose (μg) | | | | | |
|---|---|---|---|---|---|---|
| | 5 | 10 | 30 | 100 | 150 | 300 |
| (L/hr)$^a$ | | | [0.39-0.58]<br>N = 4 | [0.53-0.84]<br>N = 6 | [0.61-0.84]<br>N = 6 | [0.65-0.97]<br>N = 6 |

% extrap AUC(0-∞) = The percentage of AUC(0-∞) obtained by extrapolation;
AUC = area under the concentration-time curve;
AUC(0-last) = AUC from time zero to the last quantifiable concentration;
AUC(0-∞) = AUC from time zero to infinity;
CL/f = apparent clearance;
Cmax = maximum observed concentration;
CI = confidence interval;
t1/2 = half-life;
Tmax = time to Cmax;
n = number of values included in the statistical analysis;
nc = not calculated
$^b$geometric mean (95% CI)
$^c$median (range)
$^d$arithmetic mean (95% CI)

G933 was absorbed with a median time to maximum concentration ($t_{max}$) of 7.0-9.0 hours after single administration of G933 at doses ranging from 5 to 150 μg, and with a median $t_{max}$ of 4.5 hours at the highest dose level of 300 μg.

The apparent terminal elimination half-life ($t_{1/2}$) of G933 was determined using at least 3 data points based on visual inspection over the 72-hour sampling period. $T_{1/2}$ was not assessable in the subjects of dose group 5 μg because of too low plasma concentrations. In the other doses group when % AUCex was higher than 20%, $t_{1/2}$ and consequently AUC$_{0-\infty}$ were also not reported. The geometric mean $t_{1/2}$ value was about 10-12 hr.

Inter-subject variability for maximum plasma concentration ($C_{max}$) and AUC$_{0-\infty}$, as expressed by coefficient of variation (CV), was moderate (3-37%) for both parameters.

No subjects were ADA positive at baseline or post-baseline.

Blood pressure, pulse, food intake, and adverse events were monitored over the course of the study and are summarized in Table 20.

All treatment-emergent adverse events (TEAE) were Grade 1 (mild) or Grade 2 (moderate) in severity. They are summarized in Table 21 below.

TABLE 20

| Dose (μg) | Median pulse peak (bpm) (a) | Median pulse maximum post dose change (bpm) (b) | Median diastolic BP peak (mm Hg) | Median diastolic BP maximum post dose change (mm Hg) | Median systolic BP peak (mm Hg) | Median systolic BP maximum post dose change (mm Hg) | Number of subjects with vomiting (vomiting episodes) | Overall daily food intake compared with placebo (%)(c) | Median glucose peak (mmol/L) after breakfast (d) | Median glucose peak (mmol/L) after lunch(e) | Median glucose peak (mmol/L) after dinner (f) |
|---|---|---|---|---|---|---|---|---|---|---|---|
| 0 | 72.2 | 11.8 | 77 | 8.5 | 134 | 12 | 0 (0) | 100 | 7.5 | 5.2 | 7.1 |
| 5 | 79.7 | 11.3 | 79.5 | 13 | 122 | 10.5 | 0 (0) | 100 | 6.2 | 4.9 | 7.0 |
| 10 | 72.8 | 12.7 | 71.5 | 8 | 124.5 | 9.5 | 0 (0) | 100 | 5.8 | 5.1 | 6.0 |
| 30 | 70 | 9.8 | 76.5 | 10.5 | 124 | 13.5 | 0 (0) | 96 | 5.4 | 4.4 | 5.2 |
| 100 | 72 | 16.8 | 86.5 | 16 | 129.5 | 8.5 | 1 (1) | 82 | 5.5 | 4.7 | 5.2 |
| 150 | 81 | 15.7 | 75 | 15 | 128.5 | 7.5 | 4 (9) | 60 | 5.1 | 5.1 | 5.2 |
| 300 | 102 | 35.5 | 80 | 19 | 138.5 | 26 | 5 (30) | 23 | 4.7 | 5.1 | 4.9 |

BP = blood pressure (a) Median pulse peak is defined as the median of the maximum pulse from pre-dose to Day 28

(b) Median pulse maximum post dose change is defined as the median of maximum change in pulse from pre-dose to Day 28

(c) Overall daily food intake across breakfast, lunch and dinner (d) Median glucose levels collected approximately 1 hour post breakfast corresponding to 3.5 hours post dose (e) Median glucose levels collected approximately 1 hour post lunch corresponding to 7 hours post dose (f) Median glucose levels collected approximately 1 hour post dinner corresponding to 13.5 hours post dose

TABLE 21

Treatment-Emergent Adverse Events by System Organ Class and Preferred Term-As Treated Population

| System Organ Class[a] Preferred Term (MedDRA Version 18.0) | Placebo N = 12 | G933 | | | | | | |
|---|---|---|---|---|---|---|---|---|
| | | 5 µg N = 6 | 10 µg N = 6 | 30 µg N = 6 | 100 µg N = 6 | 150 µg N = 6 | 300 µg N = 6 | Total N = 36 |
| Subjects with at least one event | 2 (16.7%) | 2 (33.3%) | 3 (50.0%) | 4 (66.7%) | 2 (33.3%) | 5 (83.3%) | 5 (83.3%) | 21 (58.3%) |
| Cardiac Disorders | 0 | 0 | 1 (16.7%) | 0 | 1 (16.7%) | 0 | 1 (16.7%) | 3 (8.3%) |
| Arrhythmia | 0 | 0 | 0 | 0 | 1 (16.7%) | 0 | 0 | 1 (2.8%) |
| Atrioventricular block second degree | 0 | 0 | 1 (16.7%) | 0 | 0 | 0 | 0 | 1 (2.8%) |
| Ventricular extrasystoles | 0 | 0 | 0 | 0 | 0 | 0 | 1 (16.7%) | 1 (2.8%) |
| Gastrointestinal Disorders | 1 (8.3%) | 0 | 1 (16.7%) | 0 | 1 (16.7%) | 5 (83.3%) | 5 (83.3%) | 12 (33.3%) |
| Abdominal distension | 0 | 0 | 0 | 0 | 0 | 2 (33.3%) | 0 | 2 (5.6%) |
| Abdominal pain | 0 | 0 | 1 (16.7%) | 0 | 0 | 0 | 0 | 1 (2.8%) |
| Diarrhoea | 0 | 0 | 1 (16.7%) | 0 | 0 | 0 | 0 | 1 (2.8%) |
| Nausea | 1 (8.3%) | 0 | 0 | 0 | 1 (16.7%) | 4 (66.7%) | 3 (50.0%) | 8 (22.2%) |
| Vomiting | 0 | 0 | 0 | 0 | 1 (16.7%) | 4 (66.7%) | 5 (83.3%) | 10 (27.8%) |
| General Disorders and Administration Site Conditions | 0 | 0 | 0 | 1 (16.7%) | 0 | 0 | 1 (16.7%) | 2 (5.6%) |
| Application site erosion | 0 | 0 | 0 | 1 (16.7%) | 0 | 0 | 0 | 1 (2.8%) |
| Injury associated with device | 0 | 0 | 0 | 0 | 0 | 0 | 1 (16.7%) | 1 (2.8%) |
| Immune System Disorders | 0 | 0 | 0 | 1 (16.7%) | 0 | 0 | 0 | 1 (2.8%) |
| Seasonal allergy | 0 | 0 | 0 | 1 (16.7%) | 0 | 0 | 0 | 1 (2.8%) |
| Infections and infestations | 1 (8.3%) | 1 (16.7%) | 0 | 0 | 0 | 0 | 0 | 1 (2.8%) |
| Nasopharyngitis | 1 (8.3%) | 1 (16.7%) | 0 | 0 | 0 | 0 | 0 | 1 (2.8%) |
| Injury, poisoning and procedural complications | 0 | 0 | 0 | 1 (16.7%) | 0 | 0 | 0 | 1 (2.8%) |
| Procedural dizziness | 0 | 0 | 0 | 1 (16.7%) | 0 | 0 | 0 | 1 (2.8%) |
| Metabolism and nutrition disorders | 0 | 0 | 0 | 0 | 0 | 2 (33.3%) | 0 | 2 (5.6%) |
| Decreased appetite | 0 | 0 | 0 | 0 | 0 | 2 (33.3%) | 0 | 2 (5.6%) |
| Musculoskeletal and connective tissue disorders | 0 | 0 | 0 | 1 (16.7%) | 0 | 0 | 0 | 1 (2.8%) |
| Musculoskeletal chest pain | 0 | 0 | 0 | 1 (16.7%) | 0 | 0 | 0 | 1 (2.8%) |
| Nervous system disorders | 0 | 1 (16.7%) | 1 (16.7%) | 1 (16.7%) | 1 (16.7%) | 2 (33.3%) | 1 (16.7%) | 7 (19.4%) |
| Dizziness | 0 | 0 | 1 (16.7%) | 1 (16.7%) | 0 | 2 (33.3%) | 1 (16.7%) | 5 (13.9%) |
| Headache | 0 | 1 (16.7%) | 0 | 1 (16.7%) | 1 (16.7%) | 1 (16.7%) | 0 | 4 (11.1%) |
| Respiratory, thoracic and mediastinal disorders | 0 | 0 | 0 | 0 | 0 | 1 (16.7%) | 0 | 1 (2.8%) |
| Oropharyngeal pain | 0 | 0 | 0 | 0 | 0 | 1 (16.7%) | 0 | 1 (2.8%) |

[a] Subjects are counted once for each System Organ Class and Preferred Term regardless of the number of events Overall, G933 was well tolerated with vomiting and increase in pulse rate and blood pressure observed at the higher doses. Pre-specified exploratory endpoints suggest a reduction in overall daily food intake in subjects treated with GP933 at all doses compared with placebo.

Individual blood glucose and insulin measurements around meal times and the median plasma glucose and insulin plasma levels by dose are shown in FIGS. 11 and 12, respectively, in the time interval 2.5-14 hours post-dose. A glucose lowering effect was seen in plasma glucose levels of subjects treated with G933 at all doses. This effect was more visible around the first meal time. Similarly, insulin plasma levels showed a dose response especially at doses of 100 µg or higher, in correspondence to the first meal time.

The most frequent TEAEs (incidence >10% of subjects) were vomiting, nausea, dizziness, and headache. TEAEs of vomiting occurred only at the highest G933 doses (100, 150, and 300 µg). There were a total of 40 vomiting episodes for the 10 subjects who experienced vomiting. Thirty episodes were from 5 subjects at the 300 µg dose, 9 episodes were from 4 subjects at the 150 µg dose, and 1 episode was from 1 subject at the 100 µg dose.

Significant vomiting defined as 3 or more episodes of vomiting on a single day or across 2 consecutive days despite adjustment to diet, was reported for 2 of 6 subjects (33.3%) in the 150 µg G933 group and 5 of 6 subjects (83.3%) in the 300 µg G933 group. Due to the events of significant vomiting observed at the 300 µg dose, the dose of G933 was de-escalated to 150 µg for the final cohort.

At doses up to 150 µg the tolerability of G933 was acceptable with respect to nausea, vomiting, tachycardia and blood pressure. At a dose of 300 µg of G933, unacceptable levels of vomiting were seen, as was a significant rise in systolic blood pressure and pulse rate. Significant rises in pulse have been seen across the range of marketed GLP-1 agonists after single dose, particularly in healthy volunteers, as has nausea and vomiting. Given that the gastrointestinal effects of G933 (vomiting) were seen at a single dose of 150 µg without any cardiovascular effects, a window exists were G933 can be safely administered to subjects with type 2 diabetes mellitus at a dose expected to improve glycemic control and drive weight reduction, without a negative impact on the cardiovascular risk profile. G933 met safety and tolerability endpoints in this single dose healthy volunteer study.

Example 5: Multiple-Ascending-Dose Study Part I (A) Subjects

Approximately 75 overweight or obese subjects with relatively well controlled type 2 diabetes mellitus (T2DM) are enrolled to participate in the study. The enrolled subjects meet the following inclusion and exclusion criteria.

Inclusion Criteria:

Male or female age 18 through 65 years at the time of screening;

Body mass index 27 to 40 kg/m$^2$ (inclusive);

Diagnosis of T2DM and glucose control managed with metformin monotherapy where no significant dose change (increase or decrease ≥500 mg/day) has occurred in the 3 months prior to screening: (a) The screening hemoglobin A1C (glycated hemoglogin;

HbA1c) value should be within the target range of 6.5% to 8.5%, or optionally 7.0% to 8.5%; (b) subjects prescribed a dipeptidyl peptidase-4 (DPPIV) inhibitor in addition to metformin monotherapy may be eligible to enter the study following a 4-week DPPIV inhibitor washout period prior to screening; (c) subjects prescribed less than 50% of the licensed dose of sulphonylurea in addition to metformin monotherapy may be eligible to enter the study following a 4-week sulphonylurea washout period; and (d) subjects prescribed a sodium-glucose co-transporter 2 (SGLT2) inhibitor in addition to metformin monotherapy may be eligible to enter the study following a 4-week SGLT2 inhibitor washout period;

Venous access suitable for multiple cannulations;

Cohort 4 subjects must be taking ≥10 mg daily dose of a statin for a period of at least 4 weeks prior to screening; and Cohort 4 subjects must be willing and able to self-administer daily subcutaneous (SC) injections following an initial self-injection of placebo during the screening period.

Exclusion Criteria:

Any condition that would interfere with evaluations of the investigational product or interpretation of subject safety or study results. Specific examples are: (a) past history of acute or chronic pancreatitis, or pancreatic amylase or lipase greater than twice the upper limit of normal (ULN) of the laboratory reference range at screening, (b) past history of gastroparesis requiring treatment, (c) past history of surgery affecting the upper GI tract likely to affect the interpretation of safety and tolerability data (d) history of cholelithiasis leading to episodes of acute cholecystitis not treated by cholecystectomy, or known biliary disease, and (e) Serum calcitonin suggestive of thyroid C-cell hyperplasia (calcitonin level >50 μg/L), medullary thyroid carcinoma, or history or family history of multiple endocrine neoplasia at screening;

History or presence of GI, renal, or hepatic disease (with the exception of Gilbert's syndrome), or any other condition known to interfere with absorption, distribution, metabolism, or excretion of drugs;

History of cancer (optionally within the last 10 years), with the exception of non-melanoma skin cancer;

History or presence of diabetic foot ulcers;

Any clinically important illness (apart from T2DM for subjects with known diabetes), medical/surgical procedure, or trauma within 4 weeks prior to Day 1 dosing;

Symptoms of insulinopenia or poor blood glucose control (eg, significant thirst, nocturia, polyuria, polydipsia, or weight loss);

Fasting blood glucose ≥200 mg/dL (11.11 mmol/L);

Positive hepatitis B surface antigen or hepatitis C virus antibody serology at screening;

Positive human immunodeficiency virus (HIV) test at screening or subject taking antiretroviral medications as determined by medical history or subject's verbal report;

Aspartate transaminase (AST)≥2.5×ULN at screening;

Alanine transaminase (ALT)≥2.5×ULN at screening;

Total bilirubin ≥2×ULN at screening;

Hemoglobin below the lower limit of the normal range at screening;

Neutrophils <1.5×10$^9$/L at screening;

Thyroid-stimulating hormone (TSH) level above the normal range at screening;

Impaired renal function defined as glomerular filtration rate (GFR)≤60 mL/minute/1.73 m$^2$ (GFR estimated according to Modification in Renal Disease);

Persistent (defined as documented on ≥2 prior occasions by the subject's usual physician) macroalbuminuria (>300 mg/L);

Significant late diabetic complications (macroangiopathy with symptoms of congestive heart disease or peripheral arterial disease, microangiopathy with symptoms of neuropathy, gastroparesis, retinopathy, nephropathy);

Cardiac conduction defect (e.g., Wolff-Parkinson-White syndrome, sick sinus syndrome) during the screening period.

Abnormal vital signs, after 10 minutes of supine rest, defined as any of the following: (a) If <60 years old, systolic BP<90 mm Hg or ≥140 mm Hg; if ≥60 years old, systolic BP<90 mm Hg or ≥150 mm Hg, (b) Diastolic BP <50 mm Hg or ≥90 mm Hg, or (c) HR<45 or >85 beats per minute;

Any clinically important abnormalities in rhythm, conduction or morphology of the resting ECG and any abnormalities in the 12-lead ECG that may interfere with the interpretation of QTc interval changes, including abnormal ST-T-wave morphology or left ventricular hypertrophy;

Prolonged QTcF >450 msec (for both genders) or shortened QTcF <340 msec, or family history of long QT syndrome;

PR (PQ) interval shortening <120 msec (PR<120 msec but >110 msec is acceptable if there is no evidence of ventricular pre-excitation);

PR (PQ) interval prolongation (>240 msec), intermittent second or third degree AV block, or AV dissociation;

QRS duration >120 msec including persistent or intermittent bundle branch block

Implantable cardiac defibrillator or a permanent pacemaker, and symptomatic ventricular and/or atrial tachyarrhythmias;

Unstable angina pectoris or stable angina pectoris classified higher than Canadian Cardiovascular Society class II or a myocardial infarction or stroke;

History of hospitalization caused by heart failure or a diagnosis of heart failure;

Known or suspected history of drug abuse within the past 3 years;

History of alcohol abuse or excessive intake of alcohol within the past 3 years;

Positive screen for drugs of abuse at screening or admission to the study unit, or positive screen for alcohol on admission to the unit prior to the administration of investigational product. Patients who utilize benzodiazepines for chronic anxiety or sleep disorders may be permitted to enter the study;

History of severe allergy/hypersensitivity or ongoing clinically important allergy/hypersensitivity;

Whole blood or red blood cell donation, or any blood loss >500 mL during the 2 months prior to screening;

Received another new chemical entity (defined as a compound that has not been approved for marketing), or has participated in any other clinical study that included drug treatment within at least 30 days or 5 half-lives prior to the first administration of investigational product in this study (whichever is longer). The period of exclusion to begin 30 days or 5 half-lives of investigational product after the final dose, or after the last visit, whichever is longest. Subjects consented and screened, but not randomized into this study or a previous Phase 1 study, are not excluded;

Concurrent participation in another study of any kind;

Use of any of the following medicinal products: (a) concurrent or previous use of a GLP-1 agonist (b) use of systemic corticosteroids within 28 days prior to screening; (c) use of compounds known to prolong the QTc interval, or (d) use of any herbal preparations or medicinal products licensed for control of body weight or appetite within 1 week prior to Day 1;

Psychiatric illness such that subjects have been committed to an institution by way of official or judicial order; and History of lactic acidosis or ketoacidosis.

(B) Study Design

A Phase ½, randomized, double-blind, multiple-ascending dose study is performed in two parts (A and B). A flow diagram of the study is provided in FIG. 13. Part A establishes a dose titration regimen for G933 (MEDI0382) and a maximal effective dose after titration, in T2DM subjects maintained on metformin therapy, over a period of approximately 12 days that is then be utilized over an extended dosing period (Part B) to establish the efficacy of G933 on weight and glycemic control.

Part A consists of 3 cohorts. Cohort 1 consists of a stable dose (e.g., 100 µg) of investigational product administered daily for 7 days (9 subjects; 6 G933, 3 placebo). Cohort 2 consists of an initial dose (e.g., 100 µg) of investigational product for 4 days and an up-titration step (titration dose 1; e.g., 150 µg) for 7 days (9 subjects; 6 G933, 3 placebo), and Cohort 3 consists of an initial dose (e.g., 100 µg) of investigational product for 4 days, an up-titration step (titration dose 1; e.g., 150 µg) for 4 days, and a second up-titration step (titration dose 2; e.g., 200 µg) for 7 days (9 subjects; 6 G933, 3 placebo).

Part B consists of 1 cohort. Subjects in this cohort (Cohort 4) are dosed at an initial dose (e.g., 100 µg) of investigational product for 4 days, an up-titration step (titration dose 1; e.g., 150 µg) for 4 days, a second up-titration step (titration dose 2; e.g., 200 µg) for 4 days, and then titration dose 2 (e.g., 200 µg) for 28 days thereafter at home (48 subjects; 24 G933, 24 placebo).

The initial dose is 100 µg. Titration doses 1 and 2 do not exceed 300 µg. The study duration for each subject varies by cohort and consists of an inpatient multiple-ascending dose (MAD) or up-titration evaluation period (beginning on Day −2 and ending after Day 8 for Cohort 1, Day 12 for Cohort 2, Day 16 for Cohort 3, and Day 13 for Cohort 4) and an outpatient follow-up period. Additionally, only for Cohort 4, a 28-day period of at-home self-administration of investigational product (with weekly site visits) is included after the second inpatient up-titration step and before the end of study visit.

Subjects are admitted two evenings prior to receiving investigational product to allow for repeat assessment of eligibility criteria and baseline mixed-meal test (MMT) and to standardize the level of physical activity before dosing the following morning. On Day 1, following an overnight fast for a minimum of 8 hours, baseline blood samples are drawn for safety, efficacy, pharmacokinetic (PK), pharmacodynamic (PD), and anti-drug antibody (ADA) laboratory tests. In addition, 12-lead ECGs are recorded, and the subject is administered a single SC dose of either G933 or placebo.

The subject remains in the facility for observation and safety tests including ECGs, telemetry, monitoring of vital signs, and assessments of the injection site for potential reactions throughout the day and during the treatment period. Additionally, for Cohort 4, 24-hour ambulatory blood pressure monitoring (ABPM) are performed.

Mixed-meal test (MMT) procedures are performed on Day −1 and on the last day of the highest dose level achieved for all cohorts. Additional time points include the first day at titration dose 1 (Cohort 2), the first day at titration dose 2 (Cohort 3), the day of discharge from the up-titration inpatient period (the fifth day of titration dose 2; Cohort 4), and the weekly site visits during the 28-day period of at-home self-administration (Cohort 4). For the MMT, the subject consumes a standardized meal (Ensure Plus®) within 5 minutes, and timed serial blood samples are obtained for measurement of glucose and parameters related to glucose metabolism just before and through 240 minutes after consumption of the standardized meal. During the inpatient period, finger prick glucose samples are collected 15 minutes prior to and 2 hours after breakfast, mid-day, and evening meals, and prior to going to bed.

Cohort 4 subjects are re-admitted for an overnight inpatient stay at the end of the at-home self-administration period to collect the final endpoints.

Body weight is measured at multiple time points including (but not limited to) prior to the first dose, during the inpatient dosing period (and during the outpatient period for Cohort 4), at discharge from the unit, and at the 7- to 14-day follow-up visit.

Pharmacokinetics samples for G933 are obtained pre- and post-dose and at various time points by cohort up until 48 hours after the last dose of G933. Samples for metformin concentration are obtained prior to G933 dosing. Antidrug antibodies samples are obtained pre-dose and at various time points up through 28 days post final dose.

Subjects are discharged from the unit the day after the final dose is administered in the study. A follow-up visit is performed for final safety assessments approximately 28 days after the last dose of investigational product.

(C) Efficacy Assessments

For evaluation of the impact on glucose control and weight after multiple doses of G933 compared to placebo, the percent change in MMT glucose AUC (up to 240 minutes post-MMT) and change in weight from baseline (Day −1) to the end of treatment in Cohort 4 are compared between G933 and placebo groups using an analysis of covariance by adjusting for baseline measurement and treatment group. Missing measurements at the end of treatment are replaced with the last available measurement. The comparison is conducted at a two-sided significance level of 0.1. A decrease in weight (e.g., between 1.3 and 2.0 kg over 4 weeks of repeat once-daily dosing) in the G933 treatment group as compared to the placebo group demonstrate that G933, e.g., at a dose of 100-300 µg, is effective to reduce weight.

Change from baseline (Day −2) in hemoglobin A1c (glycated hemoglobin, HbA1c) and fructosamine, and percent change from baseline (Day −1) in 24-hour glucose AUC post-MMT, are analyzed in Cohort 4 similarly to the evaluation of weight. The 24-hour glucose AUC analyses include glucose measures from the pre-/post-MMT glucose metabolism panel as well as serum chemistry glucose levels and PD glucose samples, where those results are from unique time points. An increase in glucose control (e.g., at least 20% reduction in glucose area under the concentration-time curve (AUC) after a mixed-meal test (MMT) and/or as measured by hemoglobin A1c and fructosamine) in the G933 treatment group as compared to the placebo group demonstrates that G933, e.g., at a dose of 100-300 µg, is effective to improve glucose control.

(D) Results (i) Part A: Cohorts 1-3

G933 was successfully administered in doses up to 200 µg once a day (QD) for up to 15 days.

Significant glucose reductions to normal levels with G933 were observed in both fasting plasma glucose and postprandial glucose from a mixed meal test. In the mixed-meal test, glucose area-under-the-curve (AUC) was reduced by >40% across Cohorts 1-3. (FIG. 14.) The change in baseline fasting glucose levels in Cohort 1 (on Day 7) and Cohort 3 (on Days 9 and 15) are shown in FIG. 15.

A dose dependent trend towards substantial weight loss up to 2 kg was observed. The results are shown in FIG. 16 and demonstrate that G933 substantially reduced body weight in overweight/obese patients with type 2 diabetes. In Cohort 3, a differential of more than 2 kg was observed.

G933 was well tolerated up to 200 µg with dose titration. The pharmacokinetics after repeat dosing are shown in FIG. 17. The PK was linear and predictable. The half life was approximately 11 hours. There was minimal or no accumulation after multiple daily dosing, and steady state was achieved between Day 4 and Day 7. The maximal plasma concentrations in the dose range tested were 4.21 µg/mL and 18.90 µg/mL. The average daily exposure ranged between 2.89 µg/mL and 12.45 µg/mL.

Only one sample was confirmed positive for anti-G933 antibody, post baseline.

Adverse events were manageable and in line with those expected of GLP-1 mono-agonists.

The vast majority of nausea and vomiting events reported occurred at the initiation of treatment, i.e., 100 µg dose level. Vomiting occurred in 26% (n=5) of patients receiving G933 and none on placebo. In Cohort 1, no vomiting events were reported. In Cohort 2, three vomiting events were reported in two active patients. Both cases occurred on Day 1 of dosing at the 100 µg level, and both cases resolved without intervention. In Cohort 3, thirteen vomiting events were reported in three active patients. Two subjects vomited on Day 1, and these cases resolved without intervention. One subject vomited six times between Day 1 and Day 5. Intravenous saline was given on Day 3, and the subject was withdrawn on Day 5.

Cardiac adverse events were reported in four (44.4%) of placebo patients and seven (36.8%) of patients treated with G933. Their frequency did not appear to increase with dose across active cohorts. An increase of about 10 bpm in pulse rate was observed in each cohort following treatment with G933. No significant change in systolic or diastolic blood pressure was observed, but a trend to a decline blood pressure was observed in all cohorts receiving either G933 or placebo.

Gastrointestinal (GI) adverse events were reported in four (44.4%) of placebo patients and in thirteen (68.4%) of patients treated with G933. GI adverse events affected 3, 4, and 6 patients in Cohorts 1, 2, and 3, respectively. The most prevalent GI adverse event was nausea, which was reported in 6 (31.6%) of patients treated with G933. Decreased appetite was reported in six (85.7%) of patients treated with G933 in Cohort 3.

One serious adverse event (SAE) was reported: *mycoplasma* pneumonia.

In summary, G933 was well tolerated, led to significant postprandial glucose reductions, and showed clinically significant dose-dependent weight loss.

(ii) Part B: Cohort 4

G933 effectively lowered blood glucose and weight loss over a 41-day dosing period. The mean reduction in glucose area-under-the-curve (AUC) from baseline (day 1) to day 41 is shown in FIG. 18. Over this time, G933 resulted in a 38.5% reduction (90% C.I. −47.1, −29.0), whereas placebo only resulted in a 16.1% reduction (90% C.I. −24.9, −8.0) (p-value: 0.001). G933 also improved glucose control as measured by HbA1c. (See FIG. 19.) After 41 days of treatment, HbA1c was reduced by 0.92 percent, from a baseline mean of 7.2% to a mean of 6.3% on day 42. In comparison, placebo only reduced HbA1c by 0.58 percent, from a baseline mean of 7.3% to a mean of 6.7%.

The effects of G933 on weight are shown in FIGS. 20 and 21. FIG. 20 shows that after 41 days of treatment with G933, patients lost about 3.83 kg, whereas patients receiving placebo lost only about 1.71 kg (a difference of 2.12 kg between G933 and placebo; p<0.001). In addition, 44% of patients treated with G933 lost at least 5 kg, whereas only 8% of patients receiving placebo lost at least 5 kg. FIG. 21 shows that after 41 days of treatment with G933, patients lost about 4.18% of their weight, whereas patients receiving placebo only lost about 1.71% of their weight (a difference of 2.47% between G933 and placebo; p<0.001). In addition, 84% of patients treated with G933 lost at least 2% of their weight, whereas only 42% of patients receiving placebo lost at least 2% of their weight.

Treatment with G933 also resulted in a decrease in liver fat. (See FIG. 22). The mean relative reduction in liver fat percentage from baseline (95% CI) with G933 versus placebo was 20.5% (7.2, 33.9) (p=0.004). A significant reduction in liver volume was also observed in patients treated with G933 as compared to placebo (0.14 L (−0.24, −0.03), p=0.01).

Overall, adverse effects were balanced in patients treated with G933 and placebo. The adverse effects are summarized in the table below. No deaths occurred.

| Subject with | Placebo N = 26 | 200 µg G933 N = 25 |
|---|---|---|
| At least one event | 21 (80.8%) | 22 (88.8%) |
| At lease one G933-related event | 15 (57.7%) | 20 (80.0%) |
| At least one event of ≥ grade 3 severity | 2 (7.7%) | 0 |
| Death (grade 5 severity) | 0 | 0 |
| At least one serious event | 1 (3.8%) | 0 |
| At least one serious and/or ≥ grade 3 severity event | 2 (7.7%) | 0 |
| At least one G933-related serious event | 1 (3.8%) | 0 |
| At least one event leading to discontinuation of G933 | 1 (3.8%) | 3 (12.0%) |

A total of 17 patients reported nausea: 4 receiving placebo (15.4%) and 13 treated with G933 (52.0%). A total of 8 patients vomited: 0 receiving placebo and 8 treated with G933 (32.0%). Nausea and vomiting were more frequent during earlier doses. (See FIG. 23.)

No adverse changes in cardiac and hemodynamic parameters were observed. No increase in systolic or diastolic blood pressure was observed. An increase of 12.8 beats per minute (bpm) in heart rate was seen at Day 13, but this had fallen to 6.9 bpm by Day 41.

Overall, G933 was effective with respect to both blood glucose lowering and weight loss of the 41-day period. Glucose metabolism based on the mixed meal test normalized and was accompanied by a significant reduction in HbA1c. Remarkably, a greater point estimate for weight reduction was observed that what would be expected for treatment with liraglutide (3 mg).

G933 was well tolerated up to 41 days with up-titrating doses from 100 µg to 200 µg, confirming steady state achievement within one week of treatment at 200 µg and minimal accumulation after multiple dosing. The maximal plasma concentrations observed at 200 µg dose levels ranged between 1.98 µg/mL and 34.30 µg/mL.

Example 6: Multiple-Ascending-Dose Study Part II (A) Subjects

Approximately 32 overweight or obese subjects with relatively well controlled type 2 diabetes mellitus (T2DM) are enrolled to participate in the study. The enrolled subjects meet the inclusion and exclusion criteria described in Example 5 with the following exceptions:

Inclusion Criteria:
Cohort 5 and 6 subjects must be willing and able to self-administer daily subcutaneous (SC) injections following an initial self-injection of placebo (or normal saline) during the screening period.

Exclusion Criteria:
Abnormal vital signs, after 10 minutes of supine rest, are defined as any of the following: (a) If systolic BP<90 mm Hg or ≥140 mm Hg; (b) Diastolic BP<50 mm Hg or ≥90 mm Hg; or (c) HR<45 or >85 bpm;
Unstable angina pectoris or stable angina pectoris classified higher than Canadian Cardiovascular Society class II or any previous medical history of myocardial infarction or stroke, or a history of a transient ischemic attack within the prior 12 months.

(B) Study Design

A randomized, double-blind, multiple-ascending dose study is performed. A flow diagram of the study is provided in FIG. 24. This study consists of 2 cohorts: cohort 5 and cohort 6. Cohort 5 consists of 16 subjects (12 active, 4 placebo) who begin dosing G933 (MEDI0382) at 100 µg for 5 days followed by 150 µg for 5 days, 200 µg for 5 days, and 300 µg for 7 days. Cohort 6 consists of a further 16 subjects (12 active, 4 placebo) who begin dosing G933 at 100 µg for 5 days followed by 200 µg for 5 days, and 300 µg for 7 days. Cohorts 5 and 6 have approximately 32 subjects total and are run in parallel.

The study consists of an inpatient up-titration evaluation period beginning on Day 3 for both Cohorts 5 and 6 and an outpatient follow-up period. The first 4 days and the final day of dosing at 300 µg are inpatient.

Subjects are admitted to the clinic as described in Example 5 for Cohorts 1-4. However, they have an initial inpatient period ending on Day 3 followed by at-home self-administration of G933 with a clinic visit at each dose up-titration step until initiation of the 300 µg dose. Subjects have a second inpatient period for the initiation of the 300 µg dose ending on the fourth day at that dose followed by at-home self administration.

Mixed-meal test (MMT) procedures are performed on Day −1, and on the last day of the highest does level achieved. Additional time points include before commencing the 300 µg dose (Day 16 for Cohort 5 and Day 11 for Cohort 6), and at the end of dosing (Day 22 for Cohort 5 and Day 17 for Cohort 6). The MMT are performed as described in Example 5.

Body weight is measured at multiple time points including (but not limited to) prior to the first dose, during the inpatient dosing period, and during the outpatient period, at discharge from the unit, at the 7- to 14-day follow-up visit, and at the 28-day End of Study Visit.

Pharmacokinetics samples for G933 are obtained pre- and post-dose and at various time points by cohort up until 48 hours after the last dose of G933. Samples for metformin concentration are obtained prior to G933 dosing. Antidrug antibodies samples are obtained pre-dose and at various time points up through 28 days post final dose.

Subjects are discharged from the unit the day after the final dose is administered in the study. A follow-up visit is performed for final safety assessments approximately 28 days after the last dose of investigational product.

(C) Results

G933 effectively lowered glucose in Cohorts 5 and 6. The glucose AUC levels observed in Cohorts 5 and 6 are shown in FIGS. 25 and 26 respectively. In Cohort 5, treatment with G933 resulted in a glucose AUC reduction of 41.7% (90% C.I. −49.9, −33.5), whereas treatment with placebo only resulted in a glucose reduction of 8.0% (90% C.I. −19.6, 3.6) (p<0.001). In Cohort 6, treatment with G933 resulted in a glucose AUC reduction of 35.8% (90% C.I. −43.3, −28.3), whereas treatment with placebo only resulted in a glucose reduction of −6.9% (90% C.I. −20.2, 6.3) (p=0.002). The effect on glucose AUC was comparable with previous cohorts, i.e. normalised about 40% reduction. The percent change from baseline glucose AUC in all cohorts in shown in FIG. 27. G933 also effectively lowered fasting glucose levels in Cohorts 5 and 6 as shown in FIG. 28.

G933 was also effective in reducing weight. As shown in FIG. 29, after 22 days of treatment, patients treated with G933 in Cohort 5 lost about 3.09 kg, whereas patients treated with placebo lost only about 0.98 kg (a difference of 2.11 kg). Similarly, after 17 days of treatment, patients treated with G933 in Cohort 6 lost about 2.23 kg, whereas patients treated with placebo lost only about 0.35 kg (a difference of 1.88 kg). Cohorts 5 (2.11 kg) and 6 (1.88 kg) both showed comparable weight loss after 22 and 17 days to that observed during the 41 days of dosing in Cohort 4.

Change in weight and glucose levels are plotted together in FIG. 30 and summarized in Table 22 below.

TABLE 22

| Cohort N = active | Weight (kg) | Glucose AUC | Fasting Glucose (mg/dl) |
|---|---|---|---|
| 1 100 ug n = 6 | −1.1 | −27.3 | −28.00 |
| 2 150 ug n = 6 | −0.5 | −8.9 | −17.90 |
| 3 200 ug n = 6 | −2.4 | −31.6 | −43.20 |
| 4 200 ug n = 25 | −2.11 | −22.5 | −32.62 |
| 5 300 ug n = 12 | −2.11 | −33.7 | −24.40 |
| 6 300 ug n = 12 | −1.88 | −28.9 | −36.94 |

G933 was well tolerated in Cohorts 5 and 6, and the adverse event profile was in line with other marketed GLP-1 analogues such as liraglutide. No deaths or serious adverse events were observed in either cohort.

Both titration schedules demonstrated that G933 up to a dose of 300 µg was well tolerated with respect to nausea and vomiting. In Cohort 5, a total of 4 patients reported 8 episodes of nausea: 1 patient (20%) who received placebo and 3 patients (27.3%) who received G933. A total of 3 patients reported 8 vomiting episodes: no patients who received placebo (0%) and 3 patients who received G933 (27.3%). In Cohort 6, a total of 5 patients reported 6 episodes of nausea: no patients who received placebo (0%) and 5 patients who received G933 (41.7%). One patient vomited twice: no patients who received placebo (0%) and 1 patient who received G933 (8.3%). Lower rates of nausea ($8/24$=33%) and vomiting ($4/24$=16%) were observed as subjects were out-patients 48 hours after the first dose.

Ambulatory blood pressure measurement showed no increase from baseline in systolic blood pressure/diastolic blood pressure (SBP/DBP) in G933-treated patients, and a potential trend towards reduction. In Cohort 5, heart rate was increased by approximately 7.6 beats per minute (BPM) from baseline following 22 days administration of G933, in line with what has been observed previously and other GLP-1 analogues and in Cohort 4. In Cohort 6, heart rate was increased by approximately 5.9 BPM from baseline following 17 days administration of G933.

Plasma concentrations of G933 after 7 days at the highest dose of 300 μg obtained with both titration schemes are presented in FIG. 31. The profiles overlapped especially once steady state was achieved, suggesting that exposure at this dose level is independent of the titration scheme adopted. The maximal plasma concentration observed at 300 μg dose ranged from 7.9 μg/mL to 30.9 μg/mL.

Summary of Multiple-Ascending-Dose Study Results (Parts I and II)

Overall, in the dose range of 100-300 μg, G933 showed a linear PK with half-life of approximately 8-11 hours, minimal accumulation after daily repeat dose, and steady state achievement between day 4 and day 7 at all four dose levels tested. The results confirmed the results from the single dose study (Example 4). Plasma concentrations reached after 7 days at the highest dose of 300 μg were independent of the titration scheme adopted. Between-subject variability in $C_{max}$ was approximately 20-30% in smaller cohorts, and 40-50% in larger Cohort 4. Maximal plasma concentrations in the dose range tested and with the titration scheme adopted, ranged between 1.98 μg/mL and 34.3 μg/mL, with an average daily plasma concentration ranging between 0.87 μg/mL and 16.3 μg/mL.

The safety and tolerability profile was comparable with other GLP-1 mimetics, and significantly, G933 resulted in both weight loss and glucose control.

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method of reducing liver fat by at least 20% comprising administering to a human subject in need thereof 50-600 µg of a peptide comprising the amino acid sequence of SEQ ID NO:19.

2. The method of claim 1, wherein the peptide is administered daily.

3. The method of claim 2, wherein the peptide is administered once daily.

4. The method of claim 3, wherein the peptide is administered for at least one week, for at least two weeks, for at least three weeks, or for at least four weeks.

5. The method of claim 4, wherein the peptide is administered by injection.

6. The method of claim 5, wherein the administration is subcutaneous.

7. The method of claim 1, wherein 100-600 µg of the peptide is administered.

8. A method of treating Nonalcoholic Steatohepatitis (NASH) la reducing liver fat by at least 20% comprising administering to a human subject in need thereof 50-600 µg of a peptide comprising the amino acid sequence of SEQ ID NO: 19.

9. The method of claim 8, wherein disease progression is stopped.

10. The method of claim 8, wherein disease progression is reversed.

11. The method of claim 8, wherein 100-600 µg of the peptide is administered.

12. The method of claim 8, wherein the peptide is administered daily.

13. The method of claim 12, wherein the peptide is administered once daily.

14. The method of claim 13, wherein the peptide is administered for at least one week, for at least two weeks, for at least three weeks, or for at least four weeks.

15. The method of claim 14, wherein the peptide is administered by injection.

* * * * *